United States Patent
Lim et al.

(10) Patent No.: US 9,758,770 B2
(45) Date of Patent: Sep. 12, 2017

(54) GENETICALLY ENGINEERED AND ACID-RESISTANT YEAST CELL WITH ENHANCED ACTIVITY OF RADIATION SENSITIVITY COMPLEMENTING KINASE AND METHOD OF PRODUCING LACTATE BY USING THE YEAST CELL

(71) Applicant: Samsung Electronics Co., Ltd., Suwon-si, Gyeonggi-do (KR)

(72) Inventors: Huisub Lim, Seoul (KR); Sungsoo Kim, Hwaseong-si (KR); Jiyoon Song, Seoul (KR); Soyoung Lee, Daejeon-si (KR); Juyoung Lee, Daegu (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/807,608

(22) Filed: Jul. 23, 2015

(65) Prior Publication Data

US 2016/0024484 A1 Jan. 28, 2016

(30) Foreign Application Priority Data

Jul. 24, 2014 (KR) ........................ 10-2014-0094159

(51) Int. Cl.
| | |
|---|---|
| *C12N 9/12* | (2006.01) |
| *C12N 15/82* | (2006.01) |
| *C12N 1/19* | (2006.01) |
| *C12P 7/56* | (2006.01) |
| *C07K 14/39* | (2006.01) |
| *C07K 14/395* | (2006.01) |
| *C12N 15/81* | (2006.01) |

(52) U.S. Cl.
CPC ............ *C12N 9/1205* (2013.01); *C07K 14/39* (2013.01); *C07K 14/395* (2013.01); *C12N 9/12* (2013.01); *C12N 15/81* (2013.01); *C12P 7/56* (2013.01); *C12Y 207/11001* (2013.01)

(58) Field of Classification Search
None
See application file for complete search history.

(56) References Cited

U.S. PATENT DOCUMENTS

| 6,429,006 B1* | 8/2002 | Porro | ................... | C07K 14/395 |
|---|---|---|---|---|
| | | | | 435/254.2 |
| 7,635,768 B2 | 12/2009 | Kandel et al. | | |
| 2004/0000974 A1 | 1/2004 | Odenaal et al. | | |
| 2007/0161098 A1* | 7/2007 | Yamaguchi | .......... | C12N 9/0006 |
| | | | | 435/139 |
| 2015/0087032 A1* | 3/2015 | Park | ........................ | C12P 7/56 |
| | | | | 435/116 |

FOREIGN PATENT DOCUMENTS

JP     2014-039533 A     3/2014

OTHER PUBLICATIONS

Bilsland et al., Rck1 and Rck2 MAPKAP kinases and the HOG pathway are required for oxidative stress resistance, Mol. Microbiol., 2004, 53, 1743-56.*
Abbott et al., Catalase Overexpression Reduces Lactic Acid-Induced Oxidative Stress in *Saccharomyces cerevisiae*, Appl. Environ. Microbiol., 2009, 75, 2320-25.*
Tokuhiro et al., Double mutation of the PDC1 and ADH1 genes improves lactate production in the yeast *Saccharomyces cerevisiae* expressing the bovine lactate dehydrogenase gene, Appl. Microbiol. Biotechnol., 2009, 82, 883-90.*
Uniprot, Accession No. P38623, 2014, www.uniprot.org.*
Pearson, Gray et al., "Mitogen-Activated Protein (MAP) Kinase Pathways: Regulation and Physiological Functions," *Endocrine Reviews*, 22(2): 153-183 (2001).
Hohmann, Stefan, "Osmotic Stress Signaling and Osmoadaptation in Yeasts," *Microbiology and Molecular Biology Reviews*, 66(2), 300-372 (2002).
Dahlkvist, A. et al., "The RCK1 and RCK2 protein kinase genes from *Saccharomyces cerevisiae* suppress cell cycle checkpoint mutations in *Schizosaccharomyces pombe*," *Mol. Gen Genet*, 246(3): 316-326 (1995).
Dahlén et al., "Regulation of Telomere Length by Checkpoint Genes in *Schizosaccharomyces pombe*", *Mol. Biol Cell*, 9(3): 611-621 (1998).

* cited by examiner

*Primary Examiner* — Robert Mondesi
*Assistant Examiner* — Todd M Epstein
(74) *Attorney, Agent, or Firm* — Leydig, Voit & Mayer, Ltd.

(57) ABSTRACT

Provided is an acid-resistant yeast cell that is genetically engineered to enhance activity of a radiation sensitivity complementing kinase, and a method of producing lactate by using the yeast cell.

17 Claims, 9 Drawing Sheets

GENETICALLY ENGINEERED AND ACID-RESISTANT YEAST CELL WITH ENHANCED ACTIVITY OF RADIATION SENSITIVITY COMPLEMENTING KINASE AND METHOD OF PRODUCING LACTATE BY USING THE YEAST CELL

RELATED APPLICATION

This application claims the benefit of Korean Patent Application No. 10-2014-0094159, filed on Jul. 24, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 164,396 byte ASCII (Text) file named "719887_ST25.TXT" created Jul. 21, 2015.

BACKGROUND

1. Field

The present disclosure relates to a genetically engineered and acid-resistant yeast cell with enhanced activity of radiation sensitivity complementing kinase and a method of producing lactate by using the yeast cell.

2. Description of the Related Art

Organic acids are widely used in a variety of industries. For example, lactate is an organic acid that is used in a variety of industrial fields, including food, pharmaceutical, chemical, and electronic industries. Lactate is a colorless, odorless, water-soluble, low-volatile material. Lactate is also not toxic to the human body, and is used as a flavoring agent, a sour taste agent, a preserving agent, or the like. Lactate is also used as a source of polylactic acid (PLA) that is an environmentally friendly, biodegradable plastic known as an alternate polymeric material.

Organic acids may be dissociated into hydrogen ions and their own negative ions at a higher pH than their own dissociation constant (pka value), for example, under a neutral condition. Meanwhile, organic acids, for example, lactic acid, may be present in the form of free acid without an electromagnetic force at a pH lower than its own pKa value. An organic acid in the form of negative ions may not be permeable with respect to a cell membrane, but may be permeable with respect to the cell membrane when it is present in the form of free acid. Therefore, an organic acid in free acid form may flow into the cells from extracellular environments where the concentration of the organic acid is high, and thus lower an intercellular pH level. Meanwhile, an organic acid present as negative ions requires an additional isolation process involving the addition of a salt. Also, a cell lacking acid-resistance may become inactive and die under acidic conditions, such as in the case of lactic acid.

Therefore, there is a need for a microorganism with acid-resistance.

SUMMARY

Provided is an acid-resistant yeast cell that is genetically engineered to have enhanced activity of radiation sensitivity complementary kinase. In some embodiments, the yeast cell comprises an exogenous polynucleotide encoding a radiation sensitivity complementing kinase; a heterologous promoter operatively linked to a polynucleotide encoding a radiation sensitivity complementing kinase, or both.

Also provided is a method of producing lactate by culturing the yeast cell.

Further provided is a method of increasing the acid resistance or lactate production of a yeast cell by increasing the expression of a radiation sensitivity complementing kinase in the yeast cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
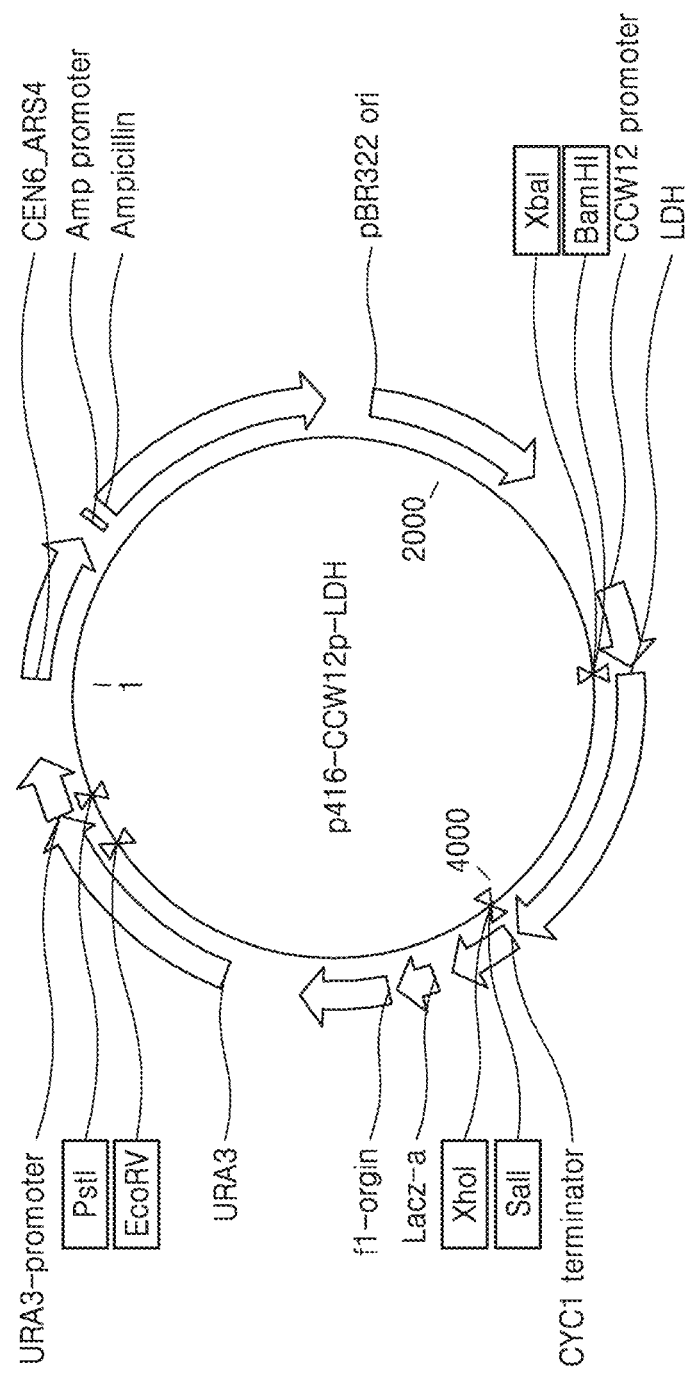
FIG. 1 is a vector map depicting a p416-CCW12p-LDH vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the term "activity increase" or "increased activity" of a cell, enzyme, polypeptide, or protein denotes that the activity level of a genetically modified (i.e., genetically engineered) cell or an enzyme or a polypeptide produced by a genetically modified cell may refer to an increase of activity of an enzyme, a polypeptide, or a protein sufficient enough to show activity and mean that the activity level of a cell or an isolated polypeptide is higher than an activity level measured in the same kind of comparable cell, parent cell, or the original polypeptide. The activity of a subject genetically engineered cell or polypeptide (or enzyme or protein) may be increased by any amount, such as by about 5% or more, about 10% or more, about 15% or more, about 20% or more, about 30% or more, about 50% or more, about 60% or more, about 70% or more, or about 100%, or about 200% or about 300% or more compared to the activity of the original non-engineered cell or polypeptide, such as the parent cell of a genetically engineered cell, or a polypeptide of the parent cell, or the wild-type cell or polypeptide (or enzyme or protein). Enhanced activity may be confirmed by using any method commonly known in the art.

Increased activity of a polypeptide (e.g., protein, or enzyme) may result from an increase in polypeptide expression level or increased specific activity of the polypeptide. The increased specific activity of the polypeptide may be due to enzyme engineering, such as by mutation or random mutagenesis of one or more specific amino acids of an active domain in the enzyme or polypeptide. The expression level increase may be due to the introduction of a polynucleotide encoding a polypeptide into a cell, by the increased number of copies of the polynucleotide in the cell, or by mutation of a regulatory region of the polynucleotide. The mutation of a regulatory region of the polynucleotide may include modification of an expression regulatory sequence of a gene. The (expression) regulatory sequence may be a promoter sequence for expression of the gene or a transcription terminator sequence. Also, the (expression) regulatory sequence may be a sequence encoding a motif that may affect the gene expression. Examples of the motif may include 2D stabilizing motifs, RNA instability motifs, splice-activating motifs, polyadenylation motifs, adenine-rich sequences, and endonuclease recognition sites.

Here, the polynucleotide introduced from the outside of the cell or the polynucleotide having increased copy number may be an endogenous gene or an exogenous gene. The endogenous gene may refer to a gene present in a genetic material contained within the microorganism. The exogenous gene may refer to a gene that is introduced to a host cell, such as a gene integrated into a host cell genome. The exogenous gene introduced into a host cell may be a homologous or heterologous with respect to the host cell. The term "heterologous" denotes that the gene is a foreign gene and is non-native to the cell into which it is inserted.

The expression "increased copy number" may include a case where a copy number increase occurs by an introduction of an exogenous gene or amplification of an endogenous gene. The introduction of the gene may occur by using a vehicle such as a vector. The introduction may be a transient introduction, in which the gene is not integrated into the genome, or integration into the genome. The introduction may, for example, occur by introducing a vector inserted with a polynucleotide encoding a desired polypeptide into the cell and then replicating the vector in the cell or integrating the polynucleotide into the genome of the cell and then replicating the polynucleotide together with the replication of the genome.

As used herein, the term "gene" denotes a polynucleotide that encodes a product and that can be expressed by at least one of transcription and translation, where an example of the product is mRNA or an encoded protein. A gene may include a coding region and, optionally, a regulatory sequence such as a 5'-non coding sequence and a 3'-non coding sequence in addition to the coding region.

The terms "cell", "strain", or "microorganism" as used herein may be interchangeably used and may include bacteria, yeast, or fungi.

As used herein, the term "activity reduction" or "decreased activity" of an enzyme or a polypeptide denotes a cell, an isolated enzyme, or a polypeptide whose activity is lower than activity measured in a comparable cell of the same type, such as a parent cell of an engineered cell, or the original "wild type" non-engineered polypeptide, enzyme or cell. Reduced and decreased activity encompasses no activity. The activity of a subject genetically engineered polypeptide, enzyme, or cell may be decreased by any amount, such as about 10% or more, about 20% or more, about 30% or more, about 40% or more, about 50% or more, about 55% or more, about 60% or more, about 70% or more, about 75% or more, about 80% or more, about 85% or more, about 90% or more, about 95% or more, or about 100% in comparison to the same biochemical activity of a polypeptide, enzyme, or cell that is not genetically engineered, such as a wild-type polypeptide, enzyme, or cell, or the activity of the parent cell of a genetically engineered cell. The decreased enzyme activity may be confirmed by using any commonly known method in the art. The decrease in activity may include the case of an enzyme having no activity or reduced activity even when the enzyme is expressed, a gene encoding the enzyme that is not expressed, or a decrease in an expression amount of the gene compared to that of a gene encoding an originally not engineered polypeptide or a wild-type polypeptide even when the gene encoding the enzyme is expressed.

Activity of the enzyme may be reduced due to deletion or disruption of a gene that encodes the enzyme. As used herein, the "deletion" or "disruption" of the gene includes mutation (insertion, deletion, or substitution) or deletion of all or part of a gene or regulatory region (e.g., promoter or terminator of a gene) such that the gene is not expressed or has a reduced amount of expression, or the activity of the gene product (e.g., enzyme) is removed or reduced even when the gene is expressed. The deletion or disruption of the gene may be caused by genetic engineering such as homologous recombination, mutation induction, or molecular evolution. When a cell includes a plurality of the same genes or at least two different polypeptide paralogs, at least one gene may be deleted or disrupted.

As used herein, the term "sequence identity" of a polypeptide or polynucleotide with respect to another polypeptide or polynucleotide refers to a degree of sameness in an amino acid sequence or a nucleic acid sequence in a specific region of two sequences that are aligned to best match each other for comparison. The sequence identity is a value obtained via optimal alignment and comparison of the two sequences in the specific region for comparison, in which a partial sequence in the specific region for comparison may be added or deleted with respect to a reference sequence. The sequence identity represented in a percentage may be calculated by, for example, comparing two sequences that are aligned to best match each other in the specific region for comparison, determining matched sites with the same amino acid or base in the two sequences to obtain the number of the matched sites, dividing the number of the matched sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTP or BLASTN (NCBI), CLC Main Workbench (CLC bio), or MegAlign™ (DNASTAR Inc).

In identifying a polypeptide or polynucleotide with the same or similar function or activity with respect to various types of species, a suitable levels of sequence identity may be applied. In some embodiments, the sequence identity may be, for example, about 50% or more, 55% or more, 60% or more, 65% or more, 70% or more, 75% or more, 80% or more, 85% or more, 90% or more, 95% or more, 96% or more, 97% or more, 98% or more, 99% or more, or 100% or more.

As used herein, the term "parent cell" may denote a cell without specific genetic modification that produces a genetically engineered cell. Also, the term "wild-type" polypeptide or polynucleotide may denote a polypeptide or a polynucleotide without specific genetic modification, where the specific genetic modification may result in a genetically engineered polypeptide or polynucleotide. For instance, with regard to a cell that is engineered to increase activity of a radiation sensitivity complementing kinase, a parent cell may be a cell of the same type that is not genetically engineered to increase activity of radiation sensitivity complementing kinase. The parent cell may be a parent strain that is genetically modified to increase activity of radiation sensitivity complementing kinase, thereby providing the genetically engineered cell. As used herein, the term "lactate" includes its anion form, a salt thereof, a solvate, a polymorph, or a combination thereof in addition to lactic acid itself. The salt may be, for example, an inorganic acid salt, an organic acid salt, or a metal salt. The inorganic acid salt may be a hydrochloride, bromate, phosphate, sulfate, or disulfate. The inorganic acid salt may be formate, acetate, propionate, lactate, oxalate, tartrate, malate, maleate, citrate, fumarate, besylate, camsylate, edisylate, trifluoroacetate, benzoate, gluconate, methansulfonate, glycolate, succinate, 4-toluenesulfonate, galacturonate, embonate, glutamate, or aspartate. The metal salt may be a calcium salt, a sodium salt, a magnesium salt, a strontium salt, or a potassium salt.

According to an exemplary embodiment, an acid-resistant yeast cell has increased activity of radiation sensitivity complementing kinase.

The radiation sensitivity complementing kinase (RCK) may be serine/threonine-protein kinase, which is an enzyme classified under EC 2.7.11.1. The radiation sensitivity complementing kinase may be RCK1 or RCK2. The radiation sensitivity complementing kinase may include an amino acid sequence having about 60% or more, 70% or more, 80% or more, 90% or more, 95% or more, 96% or more, 97% or more, 98% or more, or 99% or more sequence identity with an amino acid sequence of SEQ ID NO: 1 or SEQ ID NO: 2. In some embodiments, RCK1 and RCK2 may each have an amino acid sequence of SEQ ID NO: 1 and an amino acid sequence of SEQ ID NO: 2. The radiation sensitivity complementing kinase may be a polynucleotide sequence that encodes a protein having at least 95% sequence identity with SEQ ID NO: 1 or 2, or may be a polynucleotide sequence of SEQ ID NO: 3 and SEQ ID NO: 4. In some other embodiments, rck1 and rck2 genes may each have a polynucleotide sequence of SEQ ID NO: 3 and SEQ ID NO: 4.

The yeast cell with an acid-resistant property may have an increased growth rate under an acid condition compared to the growth rate of a parent cell. The acid condition may be an acid condition including an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may have an increased growth rate as compared to a parent cell under a pH condition in a range of about 2.0 to about 7.0, for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which activity of the radiation sensitivity complementing kinase is not increased.

Also, the yeast cell with an acid-resistant property may have a higher survival rate under an acid condition compared to that of a parent cell. The acid condition may be an acid condition including an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may have a higher survival rate under a pH condition in a range of about 2.0 to about 7.0, for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which activity of the radiation sensitivity complementing kinase is not increased.

Also, the yeast cell with an acid-resistant property of may have increased metabolism under an acid condition compared to that of a parent cell. The acid condition may be an acid condition including an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may have increased metabolism under a pH condition in a range of about 2.0 to about 7.0, for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which activity of the radiation sensitivity complementing kinase is not increased. Here, a degree of "metabolism" may be measured by a nutrition uptake rate per cell, for example, a glucose uptake rate per cell. Also, a degree of "metabolism" may be measured by a product secretion rate per cell, for example, a carbon dioxide secretion rate per cell.

The yeast cell may belong to *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus. *Saccharomyces* genus may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoi-*

*deus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus.*

The increase in activity of RCK may be due to the increased copy number of the gene, or due to modification of an expression regulatory sequence (e.g., promoter) of the gene. The increased copy number may be caused by introduction of a gene from outside to inside of the cell or by amplification of an endogenous gene.

The introduction of a gene may be performed by mediation of vehicles, such as a vector. The introduction may be transient introduction that is not integrated to a genome or introduction inserted in a genome. For example, the introduction may be performed by introducing a vector, to which the gene is inserted, to a cell, and copying the vector in the cell or integrating the gene into the genome. The gene may be operably connected to a regulatory sequence involved in regulation of expression of the gene. The regulatory sequence may include a promoter, a 5'-non coding sequence, a 3'-non coding sequence, an transcription terminator sequence, an enhance, or a combination thereof. The gene may be an endogenous gene or an exogenous gene. Also, the regulatory sequence may be a sequence encoding a motif that may affect the gene expression. Examples of the motif may include 2D stabilizing motifs, RNA instability motifs, splice-activating motifs, polyadenylation motifs, adenine-rich sequences, and endonuclease recognition sites.

The increase in activity of RCK may be caused by mutation of the one or more genes encoding the RCK. The mutation may cause substitution, insertion, addition, or conversion of at least one base.

The increase in activity of RCK can be caused by linking an endogenous or exogenous gene to a promoter with increased activity as compared to the native RCK promoter of a given cell (e.g., a heterologous promoter that does not normally drive expression of RCK). Suitable promoters may include a constitutive promoter. The constitutive promoter may be derived from triose phosphate isomerase (TPI1), covalently linked cell wall protein 12 (CCW12), pyruvate decarboxylase 1 (PDC1), phosphoglycerate kinase (PGK1), transcription enhancer factor-1 (TEF-1), glyceraldehyde-3-phosphate dehydrogenase (TDH1, TDH2, TDH3, GPD), purine-cytosine permease (PCPL3), alcohol dehydrogenase (ADH1) genes, or combination thereof.

The yeast cell may have a capability of producing lactate. The yeast cell may have an activity of a polypeptide that converts pyruvate into lactate. The yeast cell may include a gene encoding a polypeptide that converts pyruvate into lactate. In the yeast cell, the activity of a polypeptide that converts pyruvate into lactate may be increased. The polypeptide that converts pyruvate into lactate may be a lactate dehydrogenase (LDH). The LDH may be an NAD(P)-dependent enzyme. Also, the LDH may be stereo-specific and may produce only L-lactate, only D-lactate, or both L-lactate and D-lactate. The NAD(P)-dependent enzyme may be an enzyme classified under EC 1.1.1.27 that converts pyruvate into L-lactate, or an enzyme classified under EC 1.1.1.28 that converts pyruvate into D-lactate.

In the yeast cell having a capability of producing lactate, an activity of LDH may be increased. The yeast cell may include a gene encoding at least one LDH, and the gene may be exogenous. A polynucleotide may be derived from bacteria, yeasts, fungi, mammals or reptiles. The polynucleotide may be a polynucleotide that encodes at least one LDH selected from the group consisting of *Lactobacillus helveticus, L. bulgaricus, L. johnsonii, L. plantarum, Pelodiscus sinensis japonicus, Ornithorhynchus anatinus, Tursiops truncatus, Rattus norvegicus, Xenopus laevis,* and *Bos Taurus.* An LDH derived from *Pelodiscus sinensis japonicus,* an LDH derived from *Ornithorhynchus anatinus,* an LDH derived from *Tursiops truncatus,* and an LDH derived from *Rattus norvegicus* may each include an amino acid sequence having about 60% or more, about 70% or more, about 80% or more, about 90% or more, about 95% or more, about 96% or more, about 97% or more, about 98% or more, or about 99% or more sequence identity with amino acids of SEQ ID NOS: 5, 6, 7, 8, and 9. In some embodiments, a polynucleotide encoding the LDH may be a polynucleotide that encodes an amino acid sequence having about 95% or more sequence identity with an amino acid sequence of SEQ ID NOS: 5, 6, 7, 8, and 9. In some other embodiments, a polynucleotide encoding the LDH may include a polynucleotide sequence that encodes an amino acid sequence having about 95% or more sequence identity with an amino acid sequence of SEQ ID NOS: 5, 6, 7, and 8, a polynucleotide sequence of SEQ ID NO: 10, or a polynucleotide sequence of SEQ ID NO: 11.

A polynucleotide encoding the LDH may be included in a vector. Examples of the vector may include a replication origin, a promoter, a LDH-encoding polynucleotide, and a terminator. The replication origin may include a yeast autonomous replication sequence (ARS). The yeast ARS may be stabilized by a yeast centrometric sequence (CEN). The promoter may be selected from the group consisting of a cytochrome c (CYC) promoter, a transcription elongation factor (TEF) promoter, a glycerol-3-phosphate dehydrogenase (GPD) promoter, an alcohol dehydrogenase (ADH) promoter, a promoter of CCW12 gene, and a promoter of PGK gene. The CYC promoter, the *TEF* promoter, the GPD promoter, the ADH promoter, the promoter of CCW12, and the promoter of PGK gene may each have a nucleotide sequence of SEQ ID NOS: 38, 39, 40, 41, 42, and 43. The terminator may be selected from the group consisting of a terminator of a gene encoding a phosphoglycerate kinase 1 (PGK1), a terminator of a gene encoding a cytochrome c 1 (CYC1), and a terminator of a gene encoding galactokinase 1 (GAL1). The CYC1 terminator may have a nucleotide sequence of SEQ ID NO: 44. The vector may further include a selection marker. The LDH-encoding polynucleotide may be included in a genome at a specific location of a yeast cell. The specific location of the yeast cell may include a locus of a gene to be deleted and disrupted, such as pyruvate decarboxylase (PDC) or cytochrome-c oxidoreductase 2 (CYB2). When the LDH-encoding polynucleotide functions to produce an active protein in a cell, the polynucleotide is considered as "functional" in a cell.

The yeast cell may include a polynucleotide that encodes one LDH or a polynucleotide that encodes multiple LDH copies, e.g., 2 to 10 copies. The yeast cell may include a polynucleotide that encodes multiple LDH copies into, for example, 1 to 8, 1 to 7, 1 to 6, 1 to 5, 1 to 4, or 1 to 3 copies. When the yeast cell includes the polynucleotide encoding multiple LDHs, each polynucleotide may include copies of the same LDH polynucleotide or copies of polynucleotides encoding at least two different LDHs. The multiple copies of the polynucleotide encoding exogenous LDHs may be included in the same locus or multiple loci in a genome of a host cell, and the promoter or terminator of each copy of the polynucleotide may be identical to or different from each other.

Also, the yeast cell may have a capability of producing lactate. Activity of the yeast cell interrupting flow of metabolic products for producing lactate may be inactivated or reduced. In the yeast cell, activity of a pathway catalyzing or assisting the flow of metabolic products for producing lactate may be increased.

In the yeast cell, activity of a polypeptide that converts pyruvate into acetaldehyde, a polypeptide that converts lactate into pyruvate, a polypeptide that converts dihydroxyacetone phosphate (DHAP) into glycerol-3-phosphate, a polynucleotide that encodes an external mitochondrial NADH dehydrogenase, a mitochondrial pyruvate carrier (MPC), a polypeptide that converts pyruvate into oxaloacetate, a polypeptide that converts acetaldehyde into ethanol, Fps1, or a combination thereof may be reduced.

In the yeast cell, a gene encoding the polypeptide that converts pyruvate into acetaldehyde may be deleted or disrupted. The polypeptide that converts pyruvate into acetaldehyde may be an enzyme that is classified under EC 4.1.1.1. The polypeptide that converts pyruvate to acetaldehyde may be a pyruvate decarboxylase, e.g., PDC1, PDC5 or PDC6. The polypeptide that converts pyruvate to acetaldehyde may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 12. The gene encoding the polypeptide that converts pyruvate to acetaldehyde may be a polynucleotide that encodes an amino acid sequence having about 95% or more sequence identity with respect to an amino acid sequence of SEQ ID NO: 12, or may have a polynucleotide sequence of SEQ ID NO: 13. For example, the gene may be pdc1, pdc5 or pdc6.

In the yeast cell, a gene encoding the polypeptide that converts lactate into pyruvate may be deleted or disrupted. The polypeptide that converts lactate into pyruvate may be a CYC-dependent enzyme. The polypeptide that converts lactate into pyruvate may be an enzyme that is classified under EC 1.1.2.4 that acts on D-lactate or EC 1.1.2.3 that acts on L-lactate. The polypeptide that converts lactate into pyruvate may be lactate cytochrome c-oxidoreductase, for example, a CYB2 (CAA86721.1), a CYB2A, a CYB2B, a DLD1, a DLD2, or a DLD3. The polypeptide that converts lactate into pyruvate may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 12. The gene encoding the polypeptide that converts lactate into pyruvate may be a polynucleotide sequence that encodes an amino acid sequence having about 95% or more sequence identity with an amino acid sequence of SEQ ID NO: 14, or may include a polynucleotide sequence of SEQ ID NO: 15.

In the yeast cell, a gene encoding the polypeptide that converts DHAP into glycerol-3-phosphate may be deleted or disrupted. The polypeptide that converts DHAP into glycerol-3-phosphate may be a cytosolic glycerol-3-phosphate dehydrogenase and may be an enzyme that catalyzes reduction of DHAP to glycerol-3-phosphate by using oxidation of NADP to NAD+ or NADP+. The polypeptide may be classified under EC 1.1.1.8. The cytosolic glycerol-3-phosphate dehydrogenase may be GPD1. The cytosolic glycerol-3-phosphate dehydrogenase may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 16. A gene encoding the cytosolic glycerol-3-phosphate dehydrogenase may include a polynucleotide sequence encoding an amino acid sequence having a sequence identity of about 95% or more with an amino acid sequence of SEQ ID NO: 14, or may include a polynucleotide sequence of SEQ ID NO: 15.

In the yeast cell, a polynucleotide that encodes the external mitochondrial NADH dehydrogenase may be deleted or disrupted. The external mitochondrial NADH dehydrogenase may be an enzyme classified under EC. 1.6.5.9 or EC. 1.6.5.3. The external mitochondrial NADH dehydrogenase may be a type II NADH: ubiquinone oxidoreductase. The external mitochondrial NADH dehydrogenase may be located on the outer surface of the inner mitochondrial facing a cytoplasm. The external mitochondrial NADH dehydrogenase may be an enzyme catalyzing oxidation of cytosolic NADH to NAD+. The external mitochondrial NADH dehydrogenase may re-oxidize cytosolic NADH formed by a glycolysis process. The external mitochondrial NADH dehydrogenase may provide cytosolic NADH to a mitochondrial respiratory chain. The external NADH dehydrogenase may be NDE1, NDE2, or a combination thereof. The external mitochondrial NADH dehydrogenase may be distinguished from an internal mitochondrial NADH dehydrogenase NDI1 that is present and functions inside mitochondria. The external mitochondrial NADH dehydrogenase may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 18 or 19. For example, NDE1 and NDE2 may each have an amino acid sequence of SEQ ID NO: 18 and 19. The gene encoding the external mitochondrial NADH dehydrogenase may be a polynucleotide sequence encoding an amino acid sequence having a sequence identity of about 95% or more with an amino acid sequence of SEQ ID NO: 18 or 19, or may have a polynucleotide sequence of SEQ ID NO: 20 or 21. In some embodiments, the nde1 gene may include a polynucleotide sequence of SEQ ID NO: 20, and the nde2 gene may include a polynucleotide sequence of SEQ ID NO: 21.

In the yeast cell, a polynucleotide that encodes the mitochondrial pyruvate carrier (MPC) may be deleted or disrupted. The MPC may be a polypeptide that is present in a mitochondrial inner membrane and functions to move cytoplasmic pyruvate to the mitochondria. The MPC may be MPC 1, MPC2, MPC3, or a combination thereof. In some embodiments, the MPC may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 22, 23, or 24. In detail, the MPC may include an amino acid sequence having a sequence identity of about 95% or more with an amino acid sequence of SEQ ID NO: 22, 23, and 24. The MPC 1, the MPC2, and the MPC3 may each have an amino acid sequence of SEQ ID NOS: 22, 23, and 24. The polynucleotide encoding the MPC may be a polynucleotide encoding a protein having a sequence identity of about 95% or more with an amino acid sequence of SEQ ID NO: 22, 23, or 24. In some other embodiments, the MPC may include a polynucleotide sequence of SEQ ID NO: 25, 26, or 27. The sequences of SEQ ID NOS: 25, 26, and 27 are each a polynucleotide encoding the MPC 1, the MPC2, and the MPC3.

In the yeast cell, the activity of a polypeptide that converts pyruvate into oxaloacetate may be reduced. The polypeptide that converts pyruvate into oxaloacetate may catalyze Mg-ATP dependent carboxylation reaction and biotin-dependent carboxylation reaction of pyruvate to oxaloacetate. The polypeptide may convert pyruvate into oxaloacetate by consuming one molecule of ATP. The polypeptide may be an enzyme classified under EC 6.4.1.1. The polypeptide may be two isoenzymes of pyruvate carboxylase (Pyc), e.g., PYC1 and/or PYC2, in *Saccharomyces* genus. The polypeptide that converts pyruvate into oxaloacetate may have an amino acid sequence having about 50% or more, about 70% or more, about 80% or more, about 90% or more, about 95% or more, about 96% or more, about 97% or more, about 98% or more, about 99% or more, or 100% with an amino acid sequence of SEQ ID NO: 28 (GenBank ID: NP_011453.1) and/or SEQ ID NO: 29 (GenBank ID: NP_009777.1). The two isoenzymes of pyruvate carboxylase may be encoded by separate genes. These genes may each include a nucleotide sequence of SEQ ID NO: 30 (GI Number: 6321376) and/or SEQ ID NO: 31 (GI Number: 63196950). These genes may be pyc1 or pyc2 encoding a pyruvate carboxylase (PYC). In the yeast cell, a gene encoding the polypeptide that converts pyruvate into oxaloacetate may have modification or mutation of an expression regulatory sequence of the gene. For example, the modification or mutation of the expression regulatory sequence in genes that encode PYC1, PYC2, or a combination thereof may be performed by substitution with a promoter having lower expression level than that of a promoter of a parent cell, e.g., $P_{PYC1}$ and $P_{PYC2}$. Examples of the promoter having low expression level include a LEUM promoter ($P_{leum}$), a cyc1 promoter, ($P_{cyc1}$), or a mutant thereof. Meanwhile, examples of the promoter having lower expression level than that of the promoter of the parent cell, e.g., $P_{PYC1}$ and $P_{PYC2}$, may include a TEF1 promoter, a GPC promoter, or a GAL promoter.

In the yeast cell, a gene encoding the polypeptide that converts acetaldehyde into ethanol may be deleted or disrupted. The polypeptide may be an enzyme that catalyzes conversion of acetaldehyde to ethanol. The polypeptide may be classified under EC. 1.1.1.1. The polypeptide may be an enzyme that catalyzes conversion of acetaldehyde to ethanol. The polypeptide may be an alcohol dehydrogenase (Adh), for example, Adh 4. The polypeptide may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 32. The gene encoding the polypeptide may include a polynucleotide sequence encoding an amino acid sequence having about 95% or more of sequence identity with an amino acid sequence of SEQ ID NO: 32, or it may include a polynucleotide sequence of SEQ ID NO: 33. For example, the gene may be adh4.

In the yeast cell, a polynucleotide that encodes Fps1 may be deleted or disrupted. The Fps1 may be aquaglyceroporin, and may be referred to as glycerol channel protein, glycerol transport polypeptide, glycerol facilitator channel, or glycerol uptake/efflux facilitator protein. Glycerol may be secreted outside the cell by using the Fps1. The Fps1 may be classified as TCDB 1.A.8.5.1 in transporter classification system provided by Transport Classification Database (M. Saier; U of CA, San Diego). The Fps1 protein (Fps1p) may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 34. A polynucleotide encoding the Fps1p may have a polynucleotide sequence encoding amino acid sequence having about 95% or more sequence identity with an amino acid sequence of SEQ ID NO: 34, or it may have a polynucleotide sequence of SEQ ID NO: 35.

In the yeast cell, the activity of a plasma membrane transporter may be increased. The term "plasma membrane transporter" may refer to a polypeptide catalyzing organic products to move across the plasma membrane, and in some embodiments, may be a carboxylic acid transporter. The carboxylic acid transporter may be a monocarboxylate permease, and in some embodiments, may be Jen1. Jen1 may have an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 36. A polynucleotide encoding the Jen1 may be a polynucleotide encoding an amino acid sequence having about 95% sequence identity with an amino acid sequence of SEQ ID NO: 36, or may be a polynucleotide sequence of SEQ ID NO: 37.

Also, in the yeast cells according to an exemplary embodiment, activity of the radiation sensitivity complementing kinase is increased as compared with that of a parent cell; a gene that encodes a polypeptide converting pyruvate into acetaldehyde, a gene that encodes a polypeptide converting lactate to pyruvate, a gene that encodes a polypeptide converting dihydroxyacetone phosphate (DHAP) into glycerol-3-phosphate, or a combination thereof is deleted or disrupted; and a gene that encodes a polypeptide converting pyruvate into lactate is included or additionally introduced to the yeast cell. The yeast cell may be *Saccharomyces cerevisiae*. In some embodiments, the yeast cell in which a gene that encodes a polypeptide converting pyruvate into acetaldehyde, a gene that encodes a polypeptide converting lactate into pyruvate, a gene that encodes a polypeptide converting DHAP into glycerol-3-phosphate, or a combination thereof is deleted or disrupted; and to which a gene that encodes a polypeptide converting pyruvate into lactate is included or additionally introduced may be have accession number: KCTC 12415 BP.

In the yeast cells according to another exemplary embodiment, activity of the radiation sensitivity complementing kinase is increased as compared with that of a parent cell; a gene that encodes a polypeptide converting pyruvate into acetaldehyde, a gene that encodes a polypeptide converting lactate into pyruvate, a gene that encodes a polypeptide converting DHAP into glycerol-3-phosphate, a polynucleotide that encodes an external mitochondrial NADH dehydrogenase, an MPC, a polypeptide that converts pyruvate into oxaloacetate, a polypeptide that converts acetaldehyde into ethanol, or a combination thereof is deleted or disrupted; and a gene that encodes a polypeptide converting pyruvate into lactate is included or additionally introduced to the yeast cell. The yeast cell may be *Saccharomyces cerevisiae*.

In the yeast cells according to another exemplary embodiment, activity of the radiation sensitivity complementing kinase is increased as compared with that of a parent cell; a gene that encodes a polypeptide converting pyruvate into acetaldehyde, a gene that encodes a polypeptide converting lactate into pyruvate, a gene that encodes a polypeptide converting DHAP into glycerol-3-phosphate, a polynucleotide that encodes an external mitochondrial NADH dehydrogenase, an MPC, a polypeptide that converts pyruvate into oxaloacetate, a polypeptide that converts acetaldehyde into ethanol, Fps1, or a combination thereof is deleted or disrupted; and a gene that encodes a polypeptide converting pyruvate into lactate is included or additionally introduced to the yeast cell. The yeast cell may be *Saccharomyces cerevisiae*.

Also provided herein is a method for preparing a recombinant yeast cell having increased acid resistance and/or increased lactate production, and method for increasing the acid resistance and/or lactate production of a yeast cell. The method comprises increasing the expression of a radiation sensitivity complementing kinase in the yeast cell. The expression of a radiation sensitivity complementing kinase can be increased by any suitable method, as described herein, such as by increasing the copy number of a polynucleotide encoding the radiation sensitivity complementing kinase, or by modifying an expression regulatory sequence of a gene encoding the radiation sensitivity complementing kinase. For instance, the expression of a radiation sensitivity complementing kinase can be increased by introducing into the yeast cell an exogenous polynucleotide that encodes the radiation sensitivity complementing kinase; by providing a heterologous promoter operatively linked to a polynucleotide encoding a radiation sensitivity complementing kinase, or both. All other aspects of the method are as described with respect to the genetically engineered yeast cell.

Another aspect of exemplary embodiments provides a composition for producing lactate, wherein the composition includes the yeast cell. The yeast cell is defined the same as described above. The composition may further comprise components useful for producing lactate, such as a cell culture medium, carbon source (e.g., glucose), and other components used for cell culture.

Another aspect of exemplary embodiments provides a method of producing lactate, wherein the method includes culturing the yeast cell. The yeast cell is defined the same as described above.

The culturing of the yeast cell may be performed in a suitable medium under suitable culturing conditions known in the art. One of ordinary skill in the art may suitably change a culture medium and culturing conditions according to the microorganism selected. A culturing method may be batch culturing, continuous culturing, or fed-batch culturing. The yeast cell is the same as described above.

The culture medium may include various carbon sources, nitrogen sources, and trace elements.

The carbon source may be, for example, one or more carbohydrates such as glucose, sucrose, lactose, fructose, maltose, starch, or cellulose; fat such as soybean oil, sunflower oil, castor oil, or coconut oil; fatty acid such as palmitic acid, stearic acid, or linoleic acid; alcohol such as glycerol or ethanol; organic acid such as acetic acid, and/or a combination thereof. The culturing may be performed by having glucose as the carbon source. The nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium is a supply source of phosphorus and may include, for example, potassium dihydrogen phosphate, dipotassium phosphate, and corresponding sodium-containing salt thereof, and a metal salt such as magnesium sulfate or iron sulfate. Also, amino acid, vitamin, a suitable precursor, or the like may be included in the culture medium. The culture medium or individual component may be added to a culture medium solution in a batch or continuous manner.

Also, pH of the culture medium solution may be adjusted by adding a compound such as ammonium hydroxide, potassium hydroxide, ammonia, phosphoric acid, and sulfuric acid to the culture medium solution by using a suitable method during the culturing process. Also, an antifoaming agent such as fatty acid polyglycol ester may be used during the culturing process to inhibit the generation of bubbles.

The yeast cell may be cultured under an aerobic, microaerobic, or anaerobic condition. In some embodiments, the microaerobic condition refers to a culturing condition in which oxygen is dissolved in the medium at a lower level than that in the atmosphere. For example, the lower oxygen concentration level may be about 0.1% to about 10%, about 1% to about 9%, about 2% to about 8%, about 3% to about 7%, or about 4% to about 6% of a saturated dissolved oxygen in the atmosphere. Also, the microaerobic condition may include maintaining a dissolved oxygen (DO) concentration of the medium in a range of about 0.9 ppm to about 3.6 ppm, for example, about 0.9 ppm to about 3.6 ppm. A temperature for the culturing may be in a range of, for example, about 20° C. to about 45° C. or about 25° C. to about 45° C. A period of time for the culturing may be continued until a desired amount of lactate is obtained. The method of producing lactate may include collecting or isolating lactate from the culture.

The collecting of lactate from the culture may be performed by using a separation and purification method known in the art. The collecting of lactate may be performed by centrifugation, ion-exchange chromatography, filtration, precipitation, extraction, distillation, or combination thereof. For example, the culture may be centrifuged to separate biomass, and a supernatant thus obtained may be separated by ion-exchange chromatography.

According to an aspect of exemplary embodiments, the yeast cell may be an acid-resistant cell, and in addition, may produce lactate at high concentration and a high yield.

According to an aspect of exemplary embodiments, the method of producing lactate may be used to product lactate at a high concentration and a high yield.

Hereinafter, the present invention will be described in further detail with reference to the following examples. These examples are for illustrative purposes only and are not intended to limit the scope of the present invention.

Example 1. Manufacture of Yeast Cell with Improved Capability of Producing Lactate (1) Manufacture of *S. cerevisiae* CEN.PK2-1D (ΔPdc1:: Ldh)

(1.1) Manufacture of Vector for Pdc1 Deletion and Ldh Introduction

In order to block a pathway from pyruvate to ethanol through acetaldehyde in *S. cerevisiae* CEN.PK2-1D, a gene that encodes a pyruvate decarboxylase1 (pdc1) was deleted. At the same time, in order to express an Ldh derived from *Pelodiscus sinensis* japonicas, a pdc1 gene was deleted by substituting the pdc1 gene with an 'ldh cassette'. As used herein, unless stated otherwise, the term "cassette" refers to a unit sequence from which a protein may be expressed, where the cassette includes promoters, coding sequences, and terminators that are operably linked with each other.

In detail, to manufacture a vector including an 'ldh cassette', PCR was performed by using a genomic DNA of *S. cerevisiae* as a template and a primer set of SEQ ID NOS:

45 and 46 as primers to obtain a CCW12 promoter sequence (SEQ ID NO: 42) and an 'ldh gene (SEQ ID NO: 10)'. The CCW12 promoter sequence (SEQ ID NO: 42) and the ldh gene (SEQ ID NO: 10) were each digested with SacI/XbaI and BamHI/SalI, and linked to a pRS416 vector (ATCC87521), which was digested with the same enzymes, i.e., SacI/XbaI and BamHI/SalI. The pRS416 vector was a yeast centromere shuttle plasmid with a T7 promoter, ampicillin resistance in bacteria, a URA3 cassette in yeast (a selectable marker), and a restriction enzyme cloning.

Next, PCR was performed on the vector thus obtained using a pCEP4 plasmid (invitrogen, Cat. no. V044-50) as a template and a primer set of SEQ ID NOS: 33 and 34 as primers to obtain amplification product, i.e., was a 'hygromycin B phosphotransferase (HPH) cassette' sequence (SEQ ID NO: 49). The HPH cassette sequence was digested with SacI, and then, linked to the vector designed with the same enzyme to prepare a vector p416-ldh-HPH including the 'ldh cassette'. The pCEP4 plasmid used herein is an episomal mammalian expression vector that uses a cytomegalovirus (CMV) immediate early enhance/promoter for high level transcription of recombinant genes inserted into the multiple cloning site. The pCEP4 plasmid also carries the hygromycin B resistance gene for stable selection in transfected cells. Here, an 'ldh cassette' includes an ldh gene and its regulatory region, and thus the ldh cassette refers to a region that allows the ldh gene to be expressed. The ldh gene was transcripted under the control of the CCW 12 promoter. Also, the 'HPH cassette' includes a hygromycin B resistance gene and its regulatory region, and thus the HPH cassette refers to a region that allows the hygromycin B resistant gene to be expressed.

In order to prepare a pdc1 deletion cassette, PCR was performed using p416-ldh-HPH as a template and a primer set of SEQ ID NOS: 50 and 51 as primers to prepare a ldh gene fragment and a pUC57-Ura3HA vector (DNA2.0 Inc.; SEQ ID NO: 52). The ldh gene fragment and pUC57-Ura3HA vector were each digested with SacI and then linked to each other to prepare a pUC-uraHA-ldh vector. PCR was performed using sequences of SEQ ID NOS: 53 and 54 having the homologous sequence with the pdc1 gene as primers to amplify the pdc1 deletion cassette from the pUC-uraHA-ldh vector. 1 to 41 of SEQ ID NO: 53 and 1 to 44 of SEQ ID NO: 54 denote sites to be homologously recombined with the homologous chromosomes of S. cerevisiae and substituted with the pdc1 gene.

(1.2) Manufacture of S. cerevisiae CEN.PK2-1D (ΔPdc1::Ldh)

The pdc1 deletion cassette prepared in (1.1) was introduced to S. cerevisiae (CEN.PK2-1D, EUROSCARF accession number: 30000B). The introduction of the pdc1 deletion cassette was performed by general heat shock transformation. Afterwards, the cells were cultured in a uracil drop out medium to allow the pdc1 ORF on the chromosome to be substituted with the cassette.

Then, PCR was performed using a genome of the cells as a template and a primer set of SEQ ID NOS: 55 and 56 as primers on the cells thus obtained to confirm deletion of pdc1. Therefore, deletion of the pdc1 gene and introduction of the ldh gene were confirmed. As a result, S. cerevisiae CEN.PK2-1D (Δpdc1::ldh) was manufactured.

(2) Manufacture of S. cerevisiae CEN.PK2-1D (ΔPdc1::Ldh, ΔCyb2::Ldh)

(2.1) Manufacture of Vector for Cyb2 Deletion

In order to block a pathway from lactate to pyruvate, a cyb2 gene was deleted from the S. cerevisiae CEN.PK2-1D (Δpdc1::ldh) prepared in (1).

In detail, PCR was performed using the pUC-uraHA-ldh vector prepared in (1.1) as a template and cyb2 homologous recombinant sequences of SEQ ID NOS: 57 and 58 as primers to obtain a cyb2 deletion cassette. 1 to 45 of SEQ ID NO: 57 and 1 to 45 of SEQ ID NO: 58 denote sites to be homologously recombined with chromosomes of S. cerevisiae and substituted with the cyb2 gene.

(2.2) Manufacture of S. cerevisiae CEN.PK2-1D (ΔPdc1::Ldh, ΔCyb2::Ldh)

The cyb2 deletion cassette prepared in (2.1) was introduced to S. cerevisiae CEN.PK2-1D (Δpdc1::ldh). The introduction of the cyb2 deletion cassette was performed by general heat shock transformation. Afterwards, the cells were cultured in a uracil drop out medium to allow the cyb2 ORF on the chromosome to be substituted with the cassette.

Then, PCR was performed using a genome of the cells as a template and a primer set of SEQ ID NOS: 59 and 60 as primers on the strain thus obtained to confirm deletion of cyb2. As a result, S. cerevisiae CEN.PK2-1D (Δpdc1::ldh, Δcyb2::ldh) was manufactured.

(3) Manufacture of S. cerevisiae CEN.PK2-1D (ΔPdc1::Ldh, ΔCyb2::Ldh, ΔGpd1::Ldh)

(3.1) Manufacture of Vector for Gpd1 Deletion

In order to block a pathway from DHAP to glycerol-3-phosphate, a gene encoding a glycerol-3-phosphate dehydrogenase 1 (gpd1) was deleted from the S. cerevisiae CEN.PK2-1D (Δpdc1::ldh, Δcyb2::ldh) prepared in (2).

In particular, PCR was performed using the pUC-uraHA-ldh vector prepared in (1.1) as a template and gpd1 homologous recombinant sequences of SEQ ID NOS: 61 and 62 as primers to obtain a gpd1 deletion cassette. 1 to 50 of SEQ ID NO: 61 and 1 to 50 of SEQ ID NO: 62 denote sites to be homologously recombined with chromosomes of S. cerevisiae and substituted with the gpd1 gene.

(3.2) Manufacture of S. cerevisiae CEN.PK2-1D (ΔPdc1::Ldh, ΔCyb2::Ldh, ΔGpd1::Ldh)

The gpd1 deletion cassette prepared in (3.1) was introduced to S. cerevisiae CEN.PK2-1D (Δpdc1::ldh, Δcyb2::ldh) prepared in (2). The introduction of the pdc1 deletion cassette was performed by general heat shock transformation. Afterwards, the cells were cultured in a uracil drop out medium to allow the gdp1 ORF on the chromosome to be substituted with the cassette.

Then, PCR was performed using a genome of the cells as a template and a primer set of SEQ ID NOS: 63 and 64 as primers on the strain thus obtained to confirm deletion of gpd1. As a result, S. cerevisiae CEN.PK2-1D (Δpdc1::ldh, Δcyb2::ldh, Δgpd1::ldh) was manufactured.

S. cerevisiae CEN.PK2-1D (Δpdc1::ldh, Δcyb2::ldh, Δgpd1::ldh) has been deposited to Korean Collection for Type Cultures (KCTC) according to the Budapest Treaty on May 30, 2013, and received an accession number KCTC 12415BP.

(4) Manufacture of S. cerevisiae CEN.PK2-1D (ΔPdc1::Ldh, ΔCyb2::Ldh, ΔGpd1::Ldh, ΔNde1, ΔNde2)

(4.1) Manufacture of Vector for Nde1 Deletion

In order to prepare an nde1 deletion cassette, PCR was performed using the pUC-uraHA-ldh vector prepared in (1.1) as a template and a primer set of SEQ ID NOS: 65 and 66 as primers to prepare an nde1 deletion cassette.

(4.2) Manufacture of S. cerevisiae CEN.PK2-1D (ΔPdc1::Ldh, ΔCyb2::Ldh, ΔGpd1::Ldh, ΔNde1)

The nde1 deletion cassette prepared in (4.1) was introduced to S. cerevisiae CEN.PK2-1D (Δpdc1::ldh, Δcyb2::ldh, Δgpd1::ldh) prepared in (3). The introduction of the nde1 deletion cassette was performed by general heat shock transformation. Afterwards, the cells were cultured in a uracil drop out medium to allow the nde1 ORF on the chromosome to be substituted with the cassette.

Then, PCR was performed using a genome of the cells as a template and a primer set of SEQ ID NOS: 67 and 68 as primers on the cells thus obtained to confirm deletion of nde1. As a result, S. cerevisiae CEN.PK2-1D (Δpdc1::ldh, Δcyb2::ldh, Δgpd1::ldh, Δnde1) was manufactured.

(4.3) Manufacture of Vector for Nde2 Deletion

In order to prepare an nde2 deletion cassette, PCR was performed using the pUC-uraHA-ldh vector prepared in (1.1) as a template and a primer set of SEQ ID NOS: 69 and 70 as primers to prepare an nde2 deletion cassette.

(4.4) Manufacture of S. cerevisiae CEN.PK2-1D (ΔPdc1::Ldh, ΔCyb2::Ldh, ΔGpd1::Ldh, ΔNde1, ΔNde2)

The nde2 deletion cassette prepared in (4.3) was introduced to S. cerevisiae CEN.PK2-1D (Δpdc1::ldh, Δcyb2::ldh, Δgpd1::ldh, Δnde1) prepared in (4.2). The introduction of the nde2 deletion cassette was performed by general heat shock transformation. Afterwards, the cells were cultured in a uracil drop out medium to allow the nde2 ORF on the chromosome to be substituted with the cassette.

Then, PCR was performed using a genome of the cells as a template and a primer set of SEQ ID NOS: 71 and 72 as primers on the cells thus obtained to confirm deletion of nde2. As a result, S. cerevisiae CEN.PK2-1D (Δpdc1::ldh, Δcyb2::ldh, Δgpd1::ldh, Δnde1, Δnde2) was manufactured.

(5) Manufacture of S. cerevisiae CEN.PK2-1D (a Pdc1::Ldh, ΔCyb2::Ldh, ΔGpd1::Ldh, ΔNde1, ΔNde2, ΔMpc1, ΔMpc2)

(5.1) Manufacture of Vector for Mpc1 Deletion

In order to delete an mpc1 gene according to homologous recombination, PCR was performed using the pUC57-Ura3HA vector prepared in (1.1) as a template and a primer set of SEQ ID NOS: 73 and 74 (i.e., mpc1_del_F and mpc1_del_R) as primers to prepare an mpc1 deletion cassette.

(5.2) Manufacture of Saccharomyces cerevisiae Having Mpc1 Deletion

The mpc1 deletion cassette prepared in (5.1) was introduced to S. cerevisiae CEN.PK2-1D (Δpdc1::ldh, Δcyb2::ldh, Δgpd1::ldh, Δnde1, Δnde2). The introduction of the mpc1 deletion cassette was performed by general heat shock transformation. Afterwards, the cells were cultured in a uracil drop out medium to allow the mpc1 ORF on the chromosome to be substituted with the cassette.

Then, PCR was performed using a genome of the cells as a template and a primer set of SEQ ID NOS: 75 and 76 as primers on the cells thus obtained to confirm deletion of mpc1. As a result, S. cerevisiae CEN.PK2-1 D (Δpdc1::ldh, Δcyb2::ldh, Δgpd1::ldh, Δnde1, Δnde2, Δmpc1) was manufactured.

(5.3) Manufacture of Vector for Mpc2 Deletion

In order to delete an mpc2 gene according to homologous recombination, PCR was performed using the pUC57-Ura3HA vector prepared in (1.1) as a template and a primer set of SEQ ID NOS: 77 and 78 (i.e., mpc2_del_F and mpc2_del_R) as primers to prepare an mpc2 deletion cassette.

(5.4)) Manufacture of Saccharomyces cerevisiae Having Mpc1 and Mpc2 Deletion

The mpc2 deletion cassette prepared in (5.3) was introduced to S. cerevisiae CEN.PK2-1D(Δpdc1::ldh, Δcyb2::ldh, Δgpd1::ldh, Δnde1, Δnde2, Δmpc1). The introduction of the mpc2 deletion cassette was performed by general heat shock transformation. Afterwards, the cells were cultured in a uracil drop out medium to allow the mpc2 ORF on the chromosome to be substituted with the cassette.

Then, PCR was performed using a genome of the cells as a template and a primer set of SEQ ID NOS: 79 and 80 as primers on the cells thus obtained to confirm deletion of mpc2. As a result, S. cerevisiae CEN.PK2-1D(Δpdc1::ldh, Δcyb2::ldh, Δgpd1::ldh, Δnde1, Δnde2, Δmpc1, Δmpc2) was manufactured.

(6) Manufacture of S. cerevisiae CEN.PK2-1D(ΔPdc1::Ldh, ΔCyb2::Ldh, ΔGpd1::Ldh, ΔNde1, ΔNde2, ΔMpc1, ΔMpc2, Ldh+)

(6.1) Manufacture of Vector for Overexpression of LDH Derived from Bos Taurus

In order to overexpress an L-ldh gene derived from Bos Taurus, the CCW12 promoter sequence (SEQ ID NO: 42) prepared in (1.1) was cleaved by SacI and XbaI, followed by being introduced to a p416-GPD vector (ATCC® 87360™) of which a GPD promoter was also cleaved by SacI and XbaI, thereby manufacturing a p416-CCW12p vector.

Afterwards, PCR was performed using a genome DNA of the L-ldh gene (SEQ ID NO: 10) derived from Bos taurus as a template and a primer set of SEQ ID NOS: 81 and 82 as primers. Then, the obtained PCR fragments and the prepared p416-CCW12p vector were each cleaved by BamHI and SalI and ligated to each other to prepare a p416-CCW12p-LDH vector. FIG. 1 depicts a p416-CCW12p-LDH vector.

Figure 2:
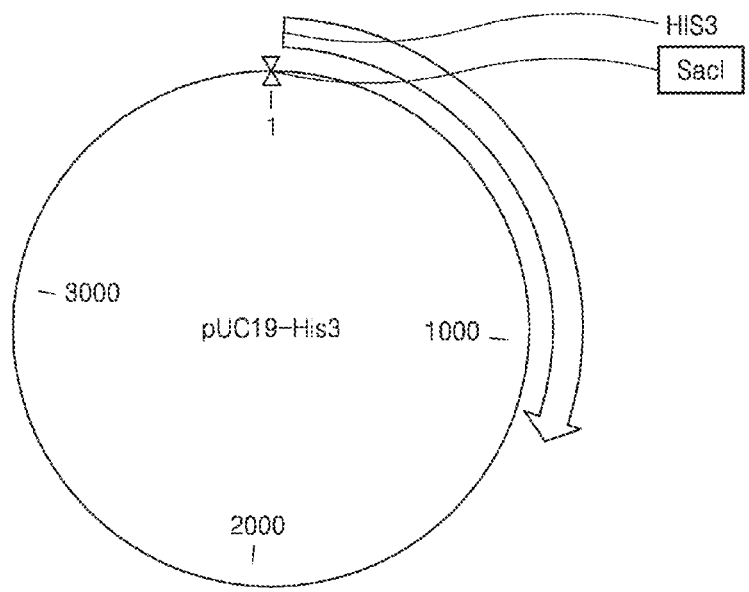
FIG. 2 is a vector map depicting a pUC19-HIS3 vector.
Figure 3:
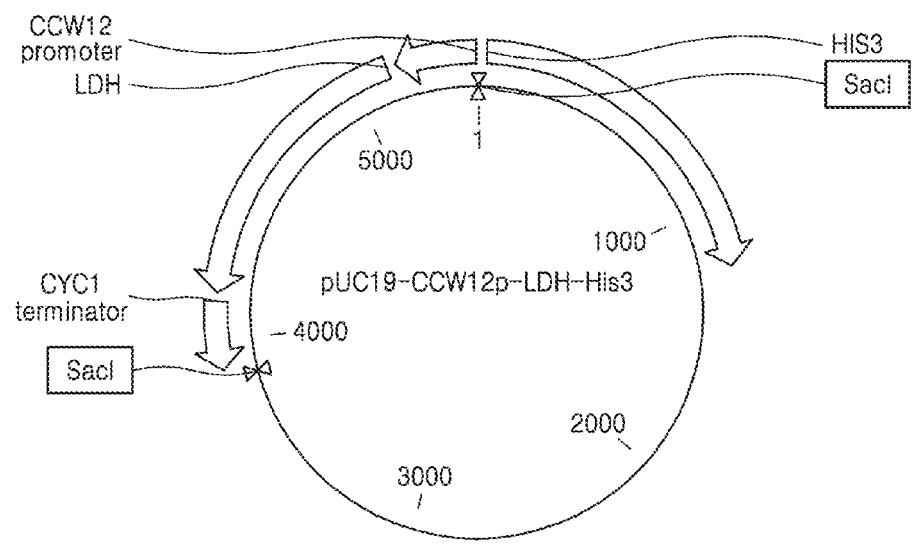
FIG. 3 is a vector map depicting a pUC19-CCW12p-LDH-HIS3 vector.

PCR was performed again using the p416-CCW12p-LDH vector as a template and a primer set of SEQ ID NOS: 83 and 84 as primers, and the PCR fragments obtained therefrom and a fabricated pUC19-HIS3 (Appl Environ Microbiol. 2002 May; 68(5):2095-100, FIG. 2) vector were each cleaved by SacI and ligated to each other to prepare a pUC19-CCW12p-LDH-HIS3 vector (FIG. 3). PCR was performed again using the pUC19-CCW12p-LDH-HIS3 vector as a template and a primer set of SEQ ID NOS: 85 and 86 as primers, so as to prepare a cassette to be introduced to a TRP1 site. Then, the expression cassette including the L-ldh gene derived from Bos taurus was able to be inserted to the TRP1 gene, and that is, the TRP1 gene was deleted while the L-ldh gene was inserted.

(6.2) Manufacture of S. cerevisiae CEN.PK2-1D (ΔPdc1::Ldh, ΔCyb2::Ldh, ΔGpd1::Ldh, ΔNde1, ΔNde2, ΔMpc1, ΔMpc2, Ldh+)

The expression cassette prepared in (6.1) including the L-ldh gene derived from Bos Taurus was introduced to S. cerevisiae CEN.PK2-1D(Δpdc1::ldh, Δcyb2::ldh, Δgpd1::ldh, Δnde1, Δnde2, Δmpc1, Δmpc2) prepared in (5). The introduction of the expression cassette was performed by general heat shock transformation. Afterwards, the cells were cultured in a histidine (his)-free minimal solid medium (YSD, 6.7 g/L yeast nitrogen base without amino acids, 1.4 g/L Amino acid dropout mix (-his)) to allow the trp1 ORF on the chromosome to be substituted with the expression cassette.

Then, PCR was performed using a genome of the cells as a template and a primer set of SEQ ID NOS: 87 and 88 as primers on the cells thus obtained to confirm deletion of the trp1 gene and introduction of the L-ldh gene. As a result, S. cerevisiae CEN.PK2-1D (Δpdc1::ldh, Δcyb2::ldh, Δgpd1::ldh, Δnde1, Δnde2, Δmpc1, Δmpc2, ldh+) was manufactured.

(7) Manufacture of S. cerevisiae CEN.PK2-1D(ΔPdc1::Ldh, ΔCyb2::Ldh, ΔGpd1::Ldh, ΔNde1 ΔNde2, ΔMpc1 ΔMpc2, Ldh+, $P_{cyc1}$PYC1)

In order to manufacture a strain with decreased pyc1 activity, replacement of the pyc1 promoter (Ppyc1) with a promoter whose expression level is lower than expression level of the Ppyc1 was performed as follows. The promoter whose expression level is lower than expression level of the Ppyc1 may be a CYC1 promoter ($P_{cyc1}$), a LEUM promoter ($P_{leum}$), or a combination thereof.

(7.1) Preparation of $P_{cyc1}$ Segment and Manufacture of a Recombinant Vector

Figure 4:
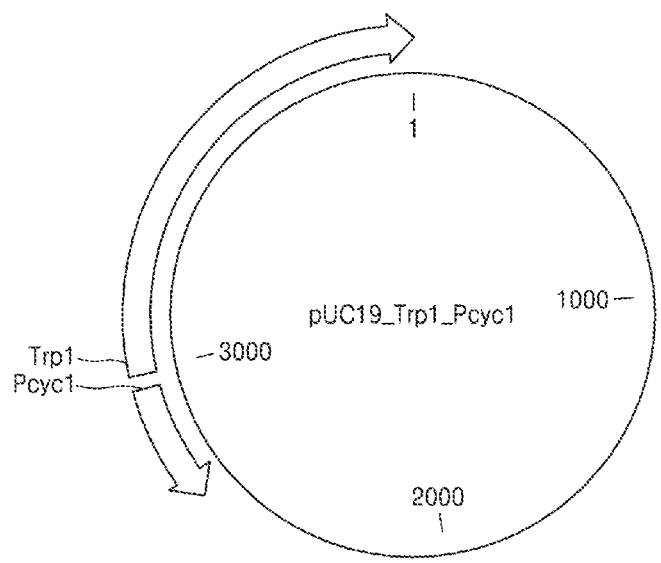
FIG. 4 is a vector map depicting a pUC19-Trp1-Pcyc1 vector.

In order to obtain DNA fragments including the CYC1 promoter ($P_{cyc1}$) (SEQ ID NO: 89), a chromosomal DNA (gDNA) of CEN.PK2-1D which is a wild strain of *Saccharomyces cerevisiae* was extracted by using Genomic-tip system manufactured by Qiagen company. Then, PCR was performed by using PCR HL premix kit (BIONEER company, hereinafter, the same kit was used) using the gDNA as a template. Following PCR, amplification of the Pcyc1 was performed using the PCR products that were obtained by using a primer set of SEQ ID NOS: 90 and 91 and then cleaved by EcoRI to prepare DNA fragments (hereinafter, referred to as "Pcyc1 cassette"), wherein the DNA fragments were then subjected to gel electrophoresis at 0.8% agarose gel and elution. Afterwards, a pUC19-Trp1 vector plasmid (Appl Environ Microbiol. 2002 May; 68(5):2095-100) and the obtained $P_{cyc1}$ cassette were treated by a restriction enzyme, EcoRI, and ligated to each other to manufacture a pUC19-Trp1-Pcyc1 vector. FIG. 4 depicts the pUC19-Trp1-Pcyc1 vector. The pUC19-TRP1-Pcyc1 was used to replay the pyc1 promoter ($P_{pyc1}$) to the cyc1 promoter ($P_{cyc1}$) according to homologous recombination. Then, PCR was performed again using the pUC19-TRP1-Pcyc1 as a template and a primer set of SEQ ID NOS: 92 and 93 as primers so as to manufacture a cassette to replace the $P_{pyc1}$ with $P_{cyc1}$.

(7.2) Manufacture of Strain Replacing Ppyc1 with Pcyc1

The $P_{cyc1}$ insertion cassette prepared in (7.1) was introduced to *S. cerevisiae* CEN.PK2-1D (Δpdc1::ldh, Δcyb2::ldh, Δgpd1::ldh, Δnde1, Δnde2, Δmpc1, Δmpc2, ldh+) prepared in (6). The introduction of the $P_{cyc1}$ insertion cassette was performed by general heat shock transformation. Afterwards, the cells were cultured in a uracil drop out medium to allow the pyc1 promoter ($P_{pyc1}$) ORF on the chromosome to be substituted with the cassette.

Then, PCR was performed using a genome of the cells as a template and a primer set of SEQ ID NOS: 94 and 95 as primers on the cells thus obtained to confirm deletion of the pyc1 promoter ($P_{pyc1}$) and introduction of the cyc1 promoter ($P_{cyc1}$). As a result, *S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1) was manufactured.

(8) Manufacture of *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1)

(8.1) Manufacture of Vector for Overexpression of Jen1

In order to overexpress a Jen1 gene, a coding site of the Jen1 gene was digested with BamHI and XhoI from genome DNA of *Saccharomyces cerevisiae* CEN.PK2-1D strain, and then, ligated to a p416-CCW12p vector, which was digested with the same enzyme, thereby manufacturing a pRS416-Jen1-CCW12p vector. Here, the Jen1 gene was transcribed by the CCW12 promoter. The Jen1 fragments obtained by PCR using the pRS416-Jen1-CCW12p as a template and the pUC57-Ura3HA vector (SEQ ID NO: 35) were each digested with SacI and ligated to each other to manufacture a pUC-uraHA-Jen1 vector. Then, a cassette for Jen1 insertion was obtained by PCR using the pUC-uraHA-Jen1 vector as a template.

(8.2) Manufacture of *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1)

The cassette prepared in (8.1) for Jen1 insertion was introduced to *S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1) prepared in (7). The introduction of the cassette was performed by general heat shock transformation. Afterwards, the cells were cultured in a uracil drop out medium to allow the adh4 ORF on the chromosome to be substituted with the cassette. As a result, *S. cerevisiae* CEN.PK2-1D(Δpdc1::ldh, Δcyb2::ldh, Δgpd1::ldh, Δnde1, Δnde2 mpc1, Δmpc2, ldh+, $P_{cyc1}$PYC1, Δadh4::$P_{ccw12}$JEN1) was manufactured.

(9) Manufacture of *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1)

(9.1) Manufacture of Vector for FPS1 Deletion

Figure 5:
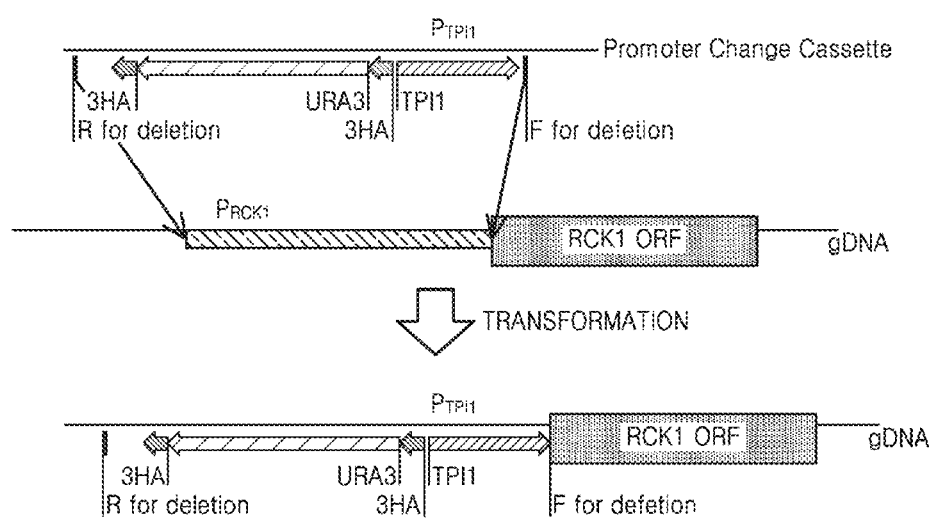
FIG. 5 is a schematic illustrating a process of manufacturing a strain to which a RCK1 promoter substitution vector is inserted in a parent strain *Saccharomyces cerevisiae*.

In order to delete a fps1 gene according to homologous recombination, PCR was performed using a pUC57-ura3HA vector of FIG. 5 as a template and a primer set of SEQ ID NOS: 96 and 97 (i.e., fps1_del_F and fps1_del_R) as primers, so as to manufacture a cassette for fps1 deletion.

(9.2) Manufacture of *S. cerevisiae* CEN.PK2-1D (a Pdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1)

The cassette prepared in (9.1) for fps1 deletion was introduced to *S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1). The introduction of the cassette was performed by general heat shock transformation. Afterwards, the cells were cultured in a uracil drop out medium to allow the fps1 ORF on the chromosome to be substituted with the cassette.

Then, PCR was performed using a genome of the cells as a template and a primer set of SEQ ID NOS: 98 and 99 as primers on the cells thus obtained to confirm deletion of the fps1gene. As a result, *S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, ΔFPS1) was manufactured.

Example 2. Manufacture of *S. cerevisiae* that Overexpresses an RCK1 Gene (1) Manufacture of Vector for Overexpression of RCK1

(1.1) Manufacture of Vector for RCK1 Promoter Replacement

In order to overexpress a RCK1 gene, replacement of the RCK1 promoter ($P_{RCK1}$) of *S. cerevisiae* CEN.PK2-1D Δpdc1::ldh Δcyb2::ldh Δgpd1::ldh (KCTC 12415BP) with TPI1 promoter ($P_{TPI1}$) whose expression level is higher than expression level of the $P_{RCK1}$ was performed as follows. FIG. 5 is a view illustrating a process of manufacturing a strain to which the RCK1 promoter substitution vector is inserted in a parent strain *S. cerevisiae*.

In order to obtain DNA fragments including the TPI1 promoter ($P_{TPI1}$) (SEQ ID NO: 100), a chromosomal DNA (gDNA) of CEN.PK2-1D which is a wild strain of *S. cerevisiae* was extracted by using Genomic-tip system manufactured by Qiagen company. Then, PCR was performed by using PCR HL premix kit using the gDNA as a template.

Figure 6:
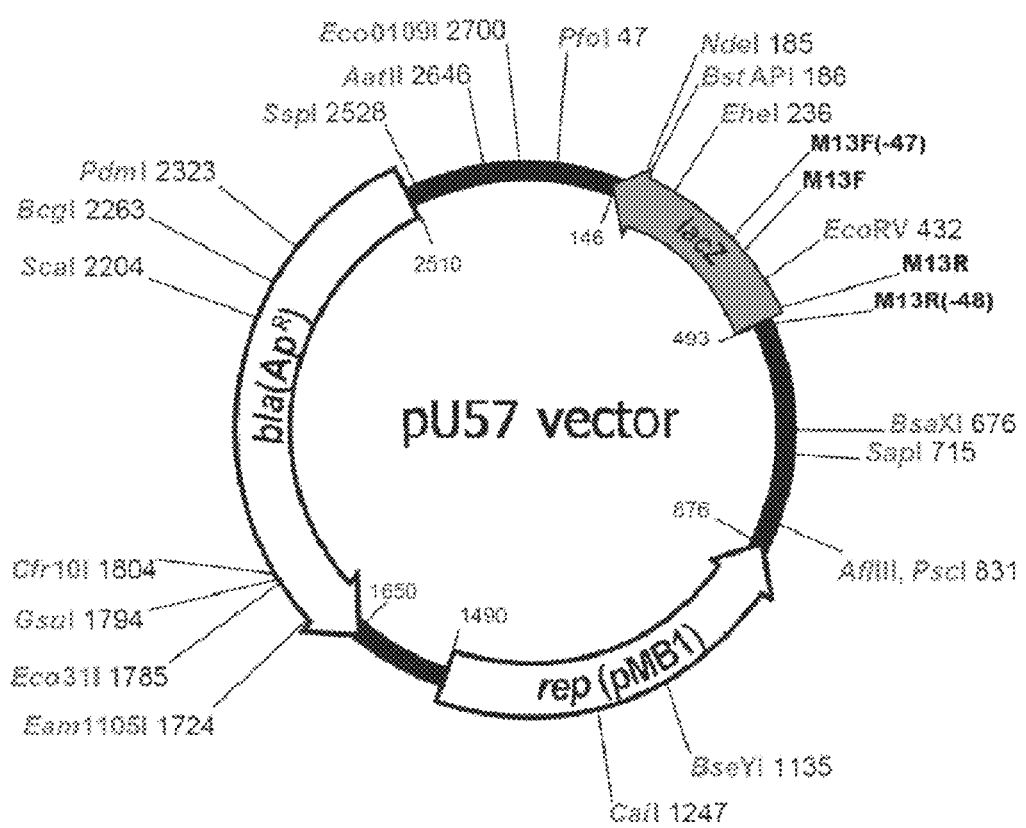
FIG. 6 is a vector map depicting a P57 vector.
Figure 7:
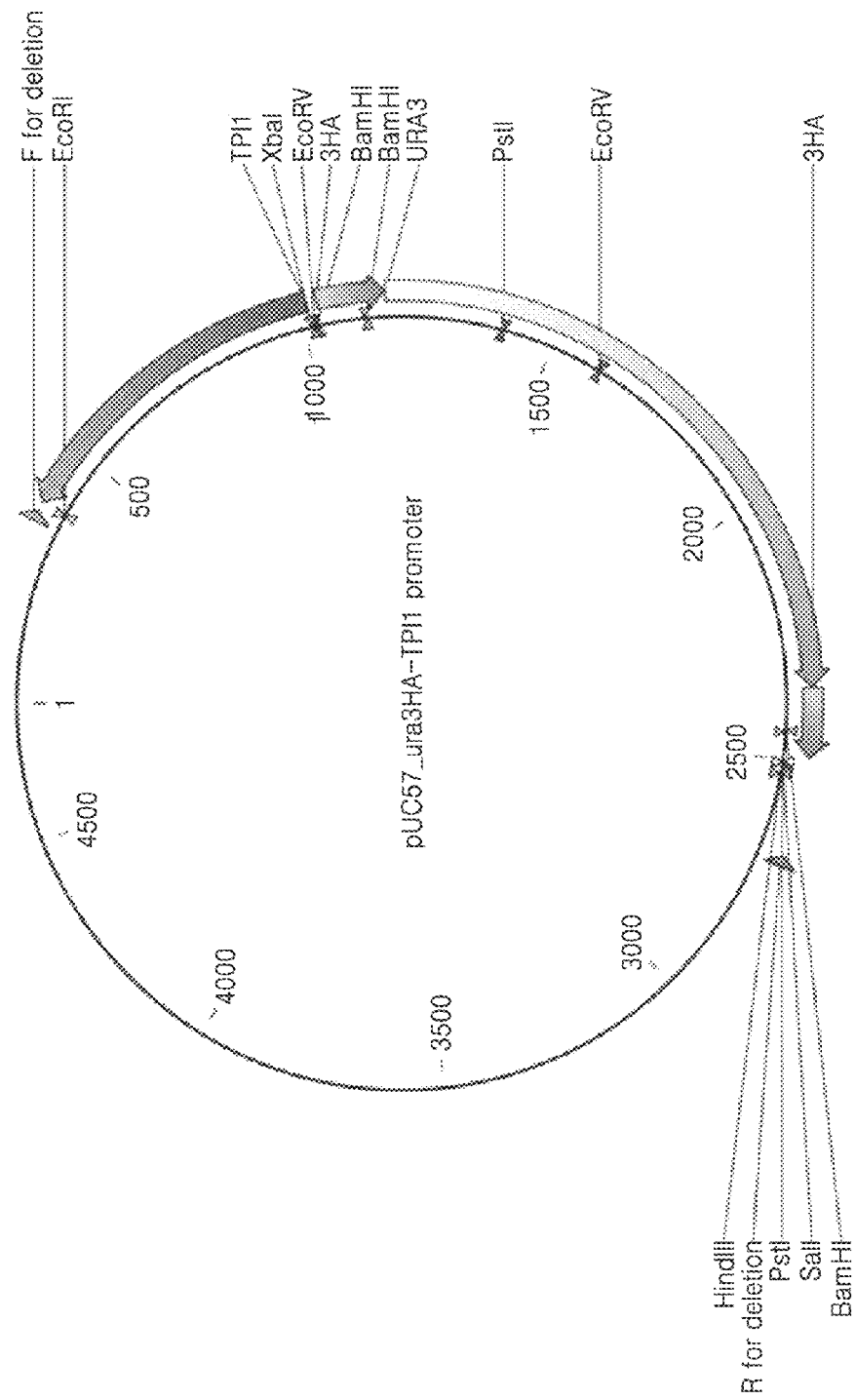
FIG. 7 is a vector map depicting a p57_ura3HA-$P_{TPI1}$ vector.

Following PCR, amplification of the $P_{TPI1}$ was performed using a primer set of SEQ ID NOS: 101 and 102 as primers and repeating a cycle 30 times of denaturation for 30 seconds at 94° C., annealing for 30 seconds at 52° C., and elongation for 30 seconds at 72° C. The PCR products were then cleaved by EcoRI to prepare DNA fragments (hereinafter, referred to as "$P_{TPI1}$ cassette"), wherein the DNA fragments were then subjected to gel electrophoresis at 0.8% agarose gel and elution. Afterwards, a P57 vector plasmid (GenScript)(SEQ ID NO: 103) and the obtained P$_{TPI1}$ cassette were treated by a restriction enzyme, EcoRI, and ligated to each other to manufacture a p57-P$_{TPI1}$ vector (SEQ ID NO: 104). FIG. 6 depicts the P57 vector and FIG. 7 depicts the p57-P$_{TPI1}$ vector.

In order to replace the RCK1 promoter (P$_{RCK1}$) with the PTPI1 promoter (P$_{TPI1}$) according to homologous recombination, PCR was performed using the p57-P$_{TPI1}$ vector as a template and a primer set of SEQ ID NOS: 105 and 106 as primers to prepare a cassette to replace the P$_{RCK1}$ with the P$_{TPI1}$.

(1.2) Manufacture of Vector for RCK1 Gene Introduction

Figure 8:
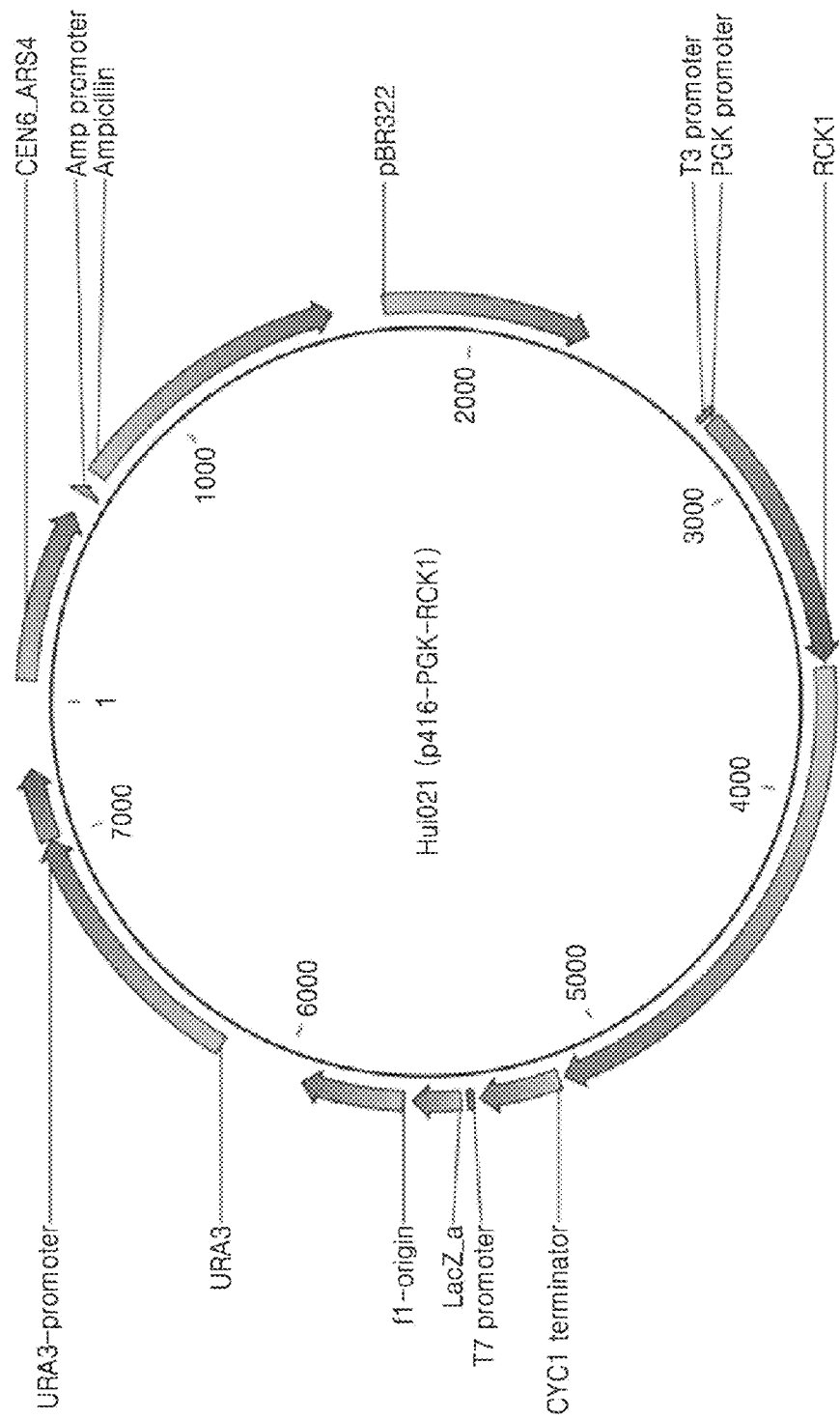
FIG. 8 is a vector map depicting a p416-PGK-RCK1 vector.

In order to prepare a vector including a RCK1 cassette, PCR was performed using a genome DNA of *S. cerevisiae* as a template and a primer set of SEQ ID NOS: 107 and 108 as primers to obtain a RCK1 ORF sequence and a PGK promoter (SEQ ID NO: 43). Each of the obtained sequence and the promoter was digested with SacI/XbaI and BamHI/SalI, and ligated to a pRS416 vector (ATCC87521) that was digested with the same enzymes, thereby obtaining a p416-PGK-RCK1 vector. FIG. 8 is a view of the p416-PGK-RCK1 vector.

(2) Manufacture of Strain for RCK1 Overexpression (2.1) Manufacture of *S. cerevisiae* CEN.PK2-1 D (ΔPdc1::Ldh, ΔCyb2::Ldh, ΔP$_{RCK1}$::P$_{TPI1}$)

The exchange cassette prepared in Example 2.1.1 was introduced to *S. cerevisiae* CEN.PK2-1D (Δpdc1::ldh, Δcyb2::ldh, Δgpd1::ldh) prepared in Example 1(3.2). The introduction of the expression cassette was performed by general heat shock transformation. Afterwards, the cells were cultured in uracil drop out medium to allow the RCK1 promoter ORF on the chromosome to be substituted with the cassette.

Then, PCR was performed using a genome of the cells as a template and a primer set of SEQ ID NOS: 109 and 110 as primers on the cells thus obtained to confirm the replacement of the P$_{RCK1}$ with P$_{TPI1}$. As a result, *S. cerevisiae* CEN.PK2-1D (Δpdc1::ldh, Δcyb2::ldh, Δgpd1::ldh, ΔP$_{RCK1}$::P$_{TPI1}$) was manufactured.

(2.2) Manufacture of *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, P$_{cyc1}$PYC1, ΔAdh4::P$_{ccw12}$JEN1, RCK1+)

The p416-PGK-RCK1 vector prepared in Example 2.1.2 was introduced to *S. cerevisiae* CEN.PK2-1D (Δpdc1::ldh, Δcyb2::ldh, Δgpd1::ldh, Δnde1, Δnde2 mpc1, Δmpc2, ldh+, P$_{cyc1}$PYC1, Δadh4::P$_{ccw12}$JEN1) prepared in Example 1(8). Such an introduction was performed by heat shock transformation typically used in the art, and afterwards, the cells were cultured in an uracil drop out medium. As a result, it was confirmed that the transformed strain CEN.PK2-1D (Δpdc1::ldh, Δcyb2::ldh, Δgpd1::ldh, Δnde1, Δnde2, Δmpc1, Δmpc2, ldh+, P$_{cyc1}$PYC1, Δadh4::P$_{ccw12}$JEN1, RCK1+) was obtained.

(2.3) Manufacture of *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, P$_{cyc1}$PYC1, ΔAdh4::P$_{ccw12}$JEN1, ΔP$_{RCK1}$::P$_{TPI1}$, ΔFPS1, ΔP$_{RCK1}$::P$_{TPI1}$)

The exchange-cassette prepared in Example 2.1.1 was introduced to the strain *S. cerevisiae* CEN.PK2-1D (Δpdc1::ldh, Δcyb2::ldh, Δgpd1::ldh, Δnde1, Δnde2, Δmpc1, Δmpc2, ldh+, P$_{cyc1}$PYC1, Δadh4::P$_{ccw12}$JEN1, ΔFPS1) prepared in Example 1(9). Such an introduction was performed by heat shock transformation typically used in the art, and afterwards, the cells were cultured in an uracil drop out medium and were set to substitute the cassette with RCK1 promoter, ORF, in a chromosome.

In regard to the strain obtained therefrom, PCR was performed by using the cell genome as a template and primers of SEQ ID NO: 109 and 110. Then, the obtained PCR products were subjected to electrophoresis to confirm the switch between P$_{RCK1}$ and P$_{TPI1}$. As a result, it was confirmed that the strain *S. cerevisiae* CEN.PK2-1D (Δpdc1::ldh, Δcyb2::ldh, Δgpd1::ldh, Δnde1, Δnde2, Δmpc1, Δmpc2, ldh+, P$_{cyc1}$PYC1, Δadh4::P$_{ccw12}$JEN1, ΔFPS1, ΔP$_{RCK1}$:P$_{TPI1}$) was obtained.

Example 3. Lactate Production by Using Strain with Overexpressed RCK1

(1) Evaluation of Lactate Production by Using Strains *S. cerevisiae* CEN.PK2-1D (ΔPdc1::Ldh, ΔCyb2::Ldh, ΔGpd1::Ldh) and *S. cerevisiae* CEN.PK2-1D (ΔPdc1::Ldh, ΔCyb2::Ldh, ΔGpd1::Ldh, ΔP$_{RCK1}$::P$_{TPI1}$)

*S. cerevisiae* CEN.PK2-1D (Δpdc1::ldh, Δcyb2::ldh, Δgpd1::ldh) (hereinafter, referred to as the strain of Control group 1) prepared in Example 1(3) and *S. cerevisiae* CEN.PK2-1D (Δpdc1::ldh, Δcyb2::ldh, Δgpd1::ldh, ΔP$_{RCK1}$::P$_{TPI1}$) prepared in Example 2(2.1) (hereinafter, referred to as the strain of Experiment group 1) were each inoculated in 25 ml of YPD broth including 9% glucose, 1% yeast extracts, and 2% Bacto-peptone, and cultured for 40 hours under anaerobic conditions by stirring the broth at a temperature of 30° C. at a rate of about 90 rpm. In the initial stage of the incubation, the optical density (OD) value of the cells at OD$_{600}$ nm was 1. Then, the yeast culture was periodically extracted from a flask during the incubation so as to measure OD values and concentrations of lactic acid, glucose, and ethanol. The cell growth in the middle of the incubation was evaluated based on OD values of the cells at OD$_{600}$ measured by using a spectrophotometer. Here, the concentrations of glucose and lactic acid were analyzed according to high performance liquid chromatography (HPLC).

Figure 9:
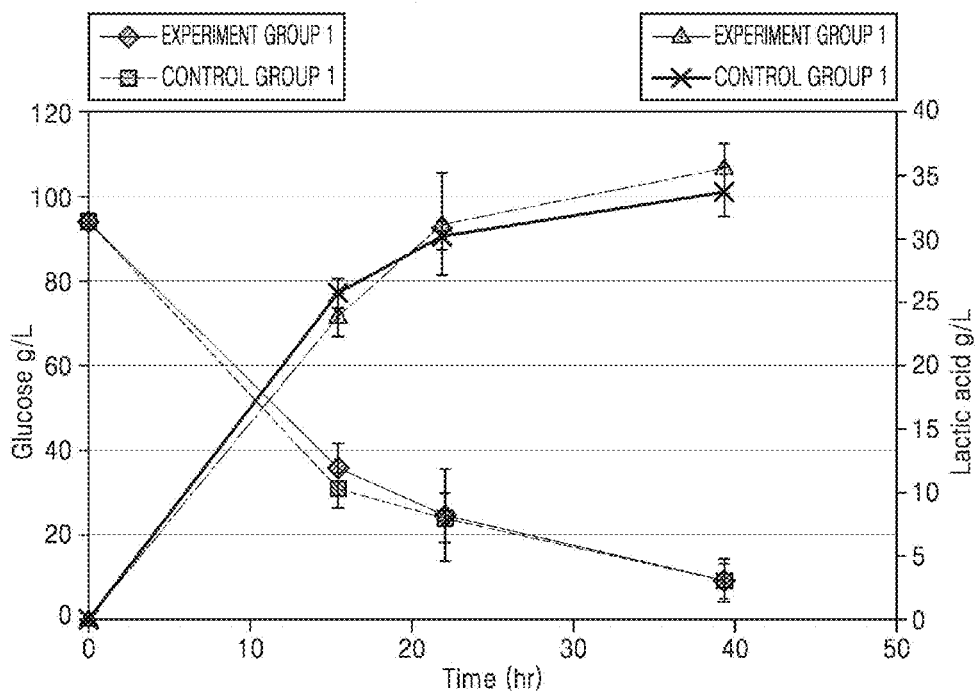
FIG. 9 is a graph that shows concentrations of lactic acid and glucose according to incubation in Control group 1 and Experiment group 1.

FIG. 9 is a graphical view that shows concentrations of lactic acid and glucose according to the incubation in Control group 1 and Experiment group 1. Referring to FIG. 9, it was confirmed that the strain of Experiment group 1 in which a RCK1 gene was overexpressed had higher lactic acid producibility than that of the strain of Control group 1.

In addition, in Table 1 below, the concentrations of lactic acid and glucose in the strains of Control group 1 and Experiment group 1 measured after 40 hours of the incubation. It was confirmed that the strain of Experiment group 1 in which a RCK1 gene was overexpressed had higher lactic acid production and yield than that of the strain of Control group 1.

TABLE 1

| Strain name | OD$_{600}$ | Glucose consumption (g/L) | LA (g/L) | ethanol (g/L) | Yield (%) |
|---|---|---|---|---|---|
| Control group 1 | 10.5 | 84.52 ± 4.90 | 34.14 ± 1.95 | 23.28 ± 1.58 | 40.39 |
| Experiment group 1 | 9.6 | 84.15 ± 4.70 | 36.61 ± 2.04 | 23.10 ± 1.17 | 43.50 |

(2) Evaluation of Lactate Producibility in Strains *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, P$_{cyc1}$PYC1, ΔAdh4::P$_{ccw12}$JEN1) and *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, RCK1+)

S. cerevisiae CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1) prepared in Example 1(8) (hereinafter, referred to as 'the strain of Control group 2') and S. cerevisiae CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, RCK1+) prepared in Example 2(2.2) (hereinafter, referred to as 'the strain of Experiment group 2') were each inoculated in 25 ml of 2×YSD/NB broth including 8% glucose, 13.4 g/L yeast nitrogen base, and yeast synthetic dropout without uracil, and cultured for 40 hours under anaerobic conditions by stirring the broth at a temperature of 30° C. at a rate of about 90 rpm. In the initial stage of the incubation, the OD value of the cells at $OD_{600}$ nm was 1. Then, the yeast culture was periodically extracted from a flask during the incubation so as to measure OD values and concentrations of lactic acid, glucose, and ethanol. The cell growth in the middle of the incubation was evaluated based on OD values of the cells at $OD_{600}$ measured by using a spectrophotometer. Here, the concentrations of glucose and lactic acid were analyzed according to HPLC.

Figure 10:
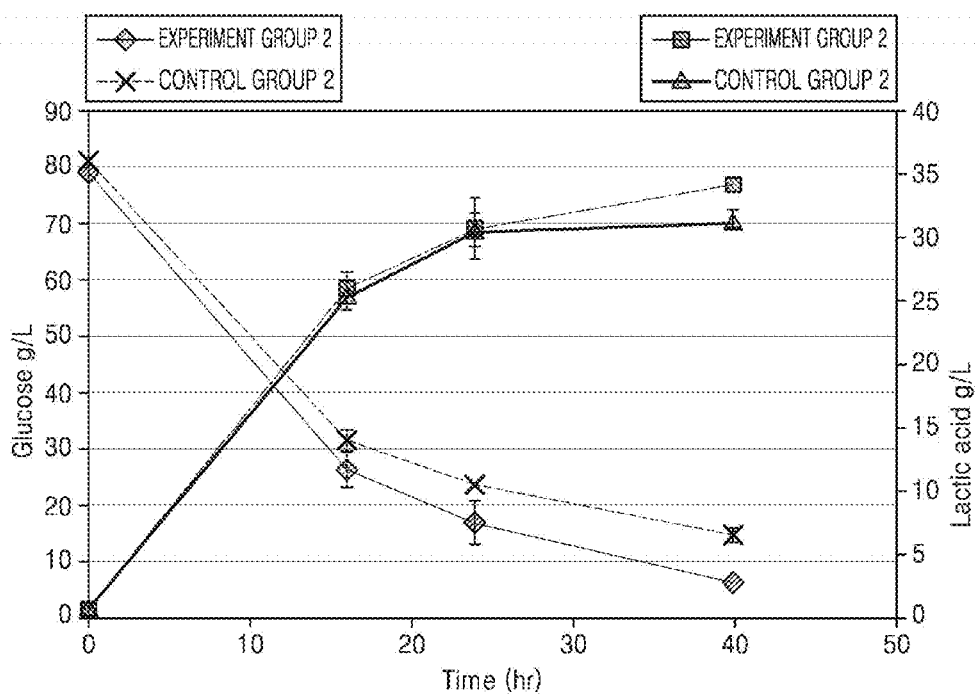
FIG. 10 is a graph that shows concentrations of lactic acid and glucose according to incubation in Control group 2 and Experiment group 2.

FIG. 10 is a graphical view that shows concentrations of lactic acid and glucose according to the incubation in Control group 2 and Experiment group 2. Referring to FIG. 10, it was confirmed that the strain of Experiment group 2 in which a RCK1 gene was overexpressed had higher lactic acid producibility and consumption of glucose than those of the strain of Control group 2.

In addition, in Table 2 below, the concentrations of lactic acid and glucose in the strains of Control group 2 and Experiment group 2 measured after 40 hours of the incubation. It was confirmed that the strain of Experiment group 2 in which a RCK1 gene was overexpressed had greater cell growth and higher glucose consumption and lactic acid production than the strain of Control group 2.

TABLE 2

| Strain name | $OD_{600}$ | Glucose consumption (g/L) | LA (g/L) | Ethanol (g/L) | Yield (%) |
|---|---|---|---|---|---|
| Control group 2 | 7.65 | 65.8 ± 1.5 | 33.9 ± 0.6 | 13.2 ± 0.48 | 51.52 |
| Experiment group 2 | 8.18 | 72.5 ± 0.5 | 37 ± 0.35 | 16.1 ± 0.31 | 50.97 |

(3) Evaluation of Lactate Producibility in Strains S. cerevisiae CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1) and S. cerevisiae CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1, Δ$P_{RCK1}$::$P_{TPI1}$)

S. cerevisiae CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, ΔFPS1) prepared in Example 1(9) (hereinafter, referred to as 'the strain of Control group 3') and S. cerevisiae CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, ΔFPS1, Δ$P_{RCK1}$::$P_{TPI1}$) prepared in Example 2(2.3) (hereinafter, referred to as 'the strain of Experiment group 3') were each inoculated in 25 ml of YPD broth including 12% glucose, 1% yeast extracts, and 2% Bacto-peptone, and cultured for 40 hours under anaerobic conditions by stirring the broth at a temperature of 30° C. at a rate of about 90 rpm. In the initial stage of the incubation, the OD value of the cells at $OD_{600}$ nm was 1. Afterwards, 3% glucose was added to the YPD broth after 24 hours of the incubation. Then, the yeast culture was periodically extracted from a flask during the incubation so as to measure OD values and concentrations of lactic acid, glucose, and ethanol. The cell growth in the middle of the incubation was evaluated based on OD values of the cells at $OD_{600}$ measured by using a spectrophotometer. The concentrations of glucose and lactic acid were analyzed according to HPLC.

Figure 11:
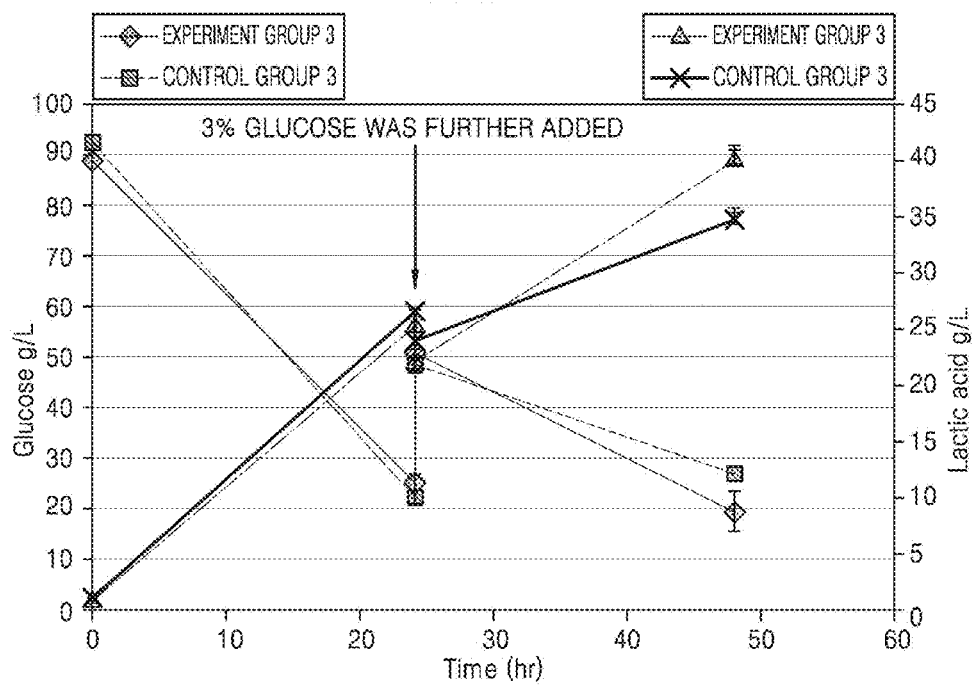
FIG. 11 is a graph that shows concentrations of lactic acid and glucose according to incubation in Control group 3 and Experiment group 3.

FIG. 11 is a graphical view that shows concentrations of lactic acid and glucose according to the incubation in Control group 3 and Experiment group 3. Referring to FIG. 11, was confirmed that the strain of Experiment group 3 in which a RCK1 gene was overexpressed had higher lactic acid production than the strain of Control group 3.

In addition, in Table 3 below, the concentrations of lactic acid and glucose in the strains of Control group 3 and Experiment group 3 measured after 40 hours of the incubation. It was confirmed that the strain of Experiment group 3 in which a RCK1 gene was overexpressed had higher glucose consumption, lactic acid production, and yield than the strain of Control group 3. Here, the lactic acid production of the strain of Experiment group 3 in which a RCK1 gene was overexpressed was improved about 16.9% as compared to that of the strain of Control group 3 in which a RCK1 gene was not overexpressed.

TABLE 3

| Strain name | $OD_{600}$ | Glucose consumption (g/L) | LA (g/L) | Ethanol (g/L) | Yield (%) |
|---|---|---|---|---|---|
| Control group 3 | 10.0 | 90.7 ± 1.50 | 33.6 ± 0.90 | 19.3 ± 0.09 | 37.05 |
| Experiment group 3 | 9.4 | 93.9 ± 1.50 | 39.3 ± 1.00 | 22.4 ± 0.65 | 41.80 |

Example 4. Measurement of Acid-Resistant Properties by Using Stain in which RCK1 Gene is Overexpressed RCK1 genes were set to be overexpressed in a yeast cell, and it was observed how such overexpression affects the acid-resistant properties of the yeast cell.

(1) Evaluation of Acid-Resistant Properties of Strains S. cerevisiae CEN.PK2-1D (ΔPdc1::Ldh, ΔCyb2::Ldh, ΔGpd1::Ldh) and S. cerevisiae CEN.PK2-1D (ΔPdc1::Ldh, ΔCyb2::Ldh, ΔGpd1::Ldh, Δ$P_{RCK1}$::$P_{TPI1}$)

The strains prepared in Control group 1 (CEN.PK2-1D (Δpdc1::ldh, Δcyb2::ldh, Δgpd1::ldh; KCTC 12415BP) and Experiment group 1 (CEN.PK2-1D (Δpdc1::ldh, Δcyb2::ldh, Δgpd1::ldh, Δ$P_{RCK1}$::$P_{TPI1}$) were each inoculated in a YPD medium including 8% glucose, 1% yeast extracts, and 2% Bacto-peptone, and cultured for 40 hours in total under anaerobic conditions by stirring the medium at a temperature of 30° C. at a rate of about 90 rpm. Here, to 2.5% lactic acid having a pH of 2.95 was added to the YPD medium. In the initial stage of the incubation, the OD value of the cells at $OD_{600}$ nm was 1. Then, the yeast culture was periodically extracted from a flask during the incubation so as to measure OD values and concentrations of lactic acid and glucose.

Figure 12:
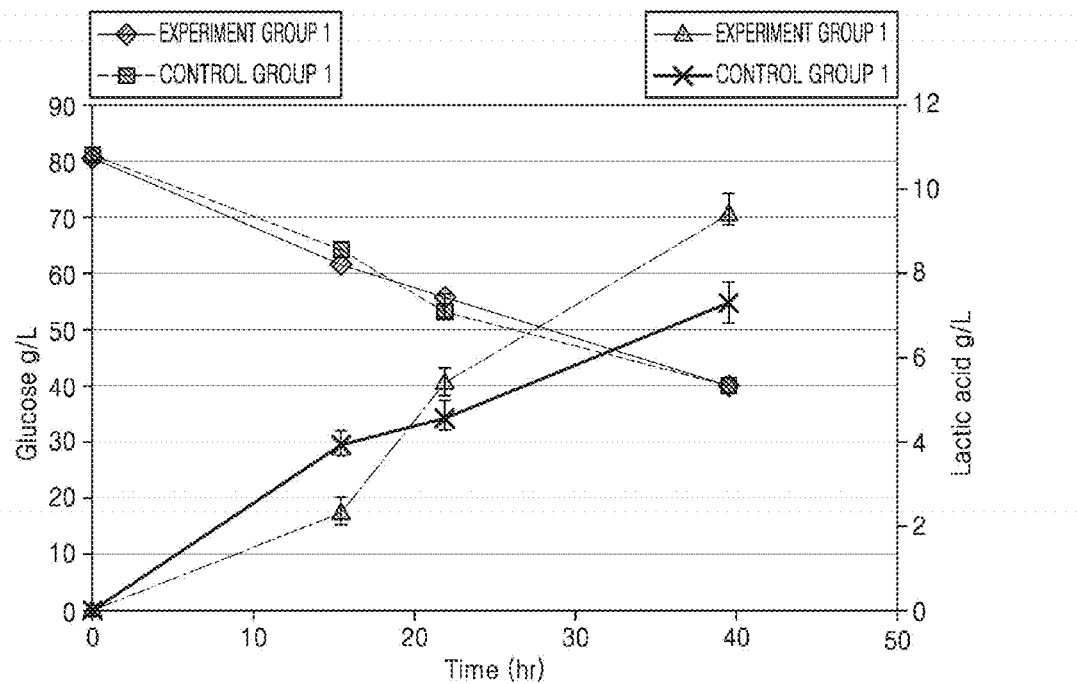
FIG. 12 is a graph that shows concentrations of lactic acid and glucose according to incubation in Control group 1 and Experiment group 1.

FIG. 12 is a graphical view that shows concentrations of lactic acid and glucose according to the incubation in Control group 1 and Experiment group 1. Referring to FIG. 12, it was confirmed that the strain of Experiment group 1 in which a RCK1 gene was overexpressed had higher lactic acid production than that of the strain of Control group 1. As lactic acid having a pH 2.95 was included in the media, the results suggest the strain of Experiment group 1 was more resistant to acid than the control group.

In addition, in Table 4 below, the concentrations of lactic acid and glucose in the strains of Control group 1 and Experiment group 1 measured after 40 hours of the incubation. It was confirmed that the strain of Experiment group 1 in which a RCK1 gene was overexpressed had higher lactic acid production and yield than the strain of Control group 1.

TABLE 4

| Strain name | $OD_{600}$ | Glucose consumption (g/L) | LA (g/L) | Yield (%) |
|---|---|---|---|---|
| Control group 1 | 5.2 ± 0.0 | 41.0 ± 1.0 | 7.7 ± 0.5 | 18.68 |
| Experiment group 1 | 5.1 ± 0.0 | 40.3 ± 0.2 | 9.8 ± 0.4 | 23.34 |

(2) Evaluation of Acid-Resistant Strains *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1) and *S. cerevisiae* CEN.PK2-1D (ΔPdc1::Ldh, ΔCyb2::Ldh, ΔGpd1::Ldh, ΔNde1, ΔNde2, ΔMpc1, ΔMpc2, Ldh+, $P_{cyc1}$PYC1, ΔAdh4::$P_{ccw12}$JEN1, ΔFPS1, $P_{RCK1}$::$P_{TPI1}$)

Control group 3 (*S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, ΔFPS1) and Experimental group 3 (*S. cerevisiae* CEN.PK2-1D (Δpdc1::ldh, Δcyb2::ldh, Δgpd1::ldh, Δnde1, Δnde2, Δmpc1, Δmpc2, ldh+, $P_{cyc1}$PYC1, Δadh4::$P_{ccw12}$JEN1, ΔFPS1, $P_{RCK1}$::$P_{TPI1}$) were each spread on a YPD solid medium and cultured at a temperature of 30° C. for at least 48 hours. Then, a colony obtained therefrom was inoculated in a 2 ml YPD broth containing 20 g/L of glucose and cultured for 24 hours in total under aerobic conditions by stirring the broth at a temperature of 30° C. at a rate of about 230 rpm. Cell growth was measured at absorbance of 600 nm, and upon dilution of the cultured cells, 10 uL of sterile water containing 10, $10^2$, $10^3$, and $10^4$ colonies, was inoculated in a medium containing lactic acid so as to confirm the viability and growth of the yeast cells.

Figure 13:
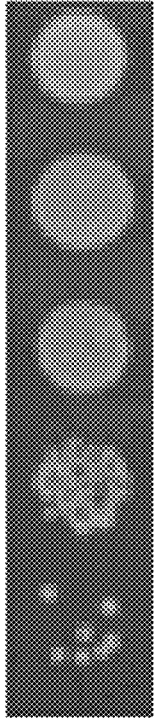
FIG. 13 is a series of images depicting the results of yeast cells cultured in an acidic YPD medium containing 45 g/L of lactic acid and having a pH of 3.5.

FIG. 13 shows the results of the viability of yeast cells cultured in an acidic YPD medium prepared with 45 g/L of lactic acid and having a pH of 3.5. Referring to FIG. 13, Experiment group 3 in which RCK1 was overexpressed exhibited greater viability than Control group 3 under the acidic conditions.

The results show that the yeast strain in which a RCK1 gene was overexpressed was unexpectedly more resistant to acid than a yeast in which RCK1 was not overexpressed.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A recombinant acid-resistant yeast cell comprising increased radiation sensitivity complementing kinase (RCK) activity as compared to the RCK activity of a parent cell of the recombinant yeast cell, wherein the yeast cell comprises a genetic modification that increases the RCK activity, wherein an activity of JEN1 is increased in the recombinant yeast cell as compared with that of a parent cell of the recombinant acid-resistant yeast cell;

wherein the recombinant acid-resistant yeast cell further comprises a polynucleotide encoding a lactate dehydrogenase; and deletion or disruption of:

a gene encoding a polypeptide that converts pyruvate to acetaldehyde;

a gene encoding a polypeptide that converts lactate to pyruvate;

a gene encoding a polypeptide that converts dihydroxyacetone phosphate (DHAP) to glycerol-3-phosphate;

a gene encoding NDE1 or NDE2, or both a gene encoding NDE1 and a gene encoding NDE2;

a gene encoding a mitochondrial pyruvate carrier (MPC);

a gene encoding a polypeptide that converts pyruvate to oxaloacetate;

a gene encoding a polypeptide that converts acetaldehyde to ethanol; and a gene encoding Fps1.

2. The recombinant yeast cell of claim 1, wherein the radiation sensitivity complementing kinase is classified under EC 2.7.11.1.

3. The recombinant yeast cell of claim 1, wherein the radiation sensitivity complementing kinase is RCK1 or RCK2.

4. The recombinant yeast cell of claim 1, wherein the radiation sensitivity complementing kinase comprises an amino acid sequence having at least 95% sequence identity with SEQ ID NO: 1 or 2.

5. The recombinant yeast cell of claim 1 comprising an increased expression level of a polynucleotide encoding the radiation sensitivity complementing kinase as compared to a parent cell of the recombinant yeast cell.

6. The recombinant yeast cell of claim 1 comprising an exogenous polynucleotide encoding the radiation sensitivity complementing kinase.

7. The recombinant yeast cell of claim 1 comprising an increased copy number of a gene encoding the radiation sensitivity complementing kinase in comparison to a parent cell of the recombinant yeast cell, or comprising a modification of an expression regulatory sequence of a gene encoding the radiation sensitivity complementing kinase, which causes the increased activity of a radiation sensitivity complementing kinase.

8. The recombinant yeast cell of claim 7 comprising an increased copy number of a gene encoding the radiation sensitivity complementing kinase in comparison to a parent cell of the recombinant yeast cell, wherein the increased copy number is due to the presence of an exogenous gene encoding the radiation sensitivity complementing kinase or amplification of an endogenous gene encoding the radiation sensitivity complementing kinase.

9. The recombinant yeast cell of claim 1, wherein the yeast cell belongs to *Saccharomyces, Kluyveromyces, Candida, Pichia, Issatchenkia, Debaryomyces, Zygosaccharomyces, Shizosaccharomyces,* or *Saccharomycopsis*.

10. The recombinant yeast cell of claim 1 wherein the polypeptide that converts pyruvate to acetaldehyde is classified as EC 4.1.1.1, the polypeptide that converts lactate to pyruvate is classified as EC 1.1.2.3 or EC 1.1.2.4, and the polypeptide that converts DHAP to glycerol-3-phosphate is classified as EC 1.1.1.8.

11. The recombinant yeast cell of claim 1, wherein the polypeptide that converts pyruvate to oxaloacetate is classified as EC 6.4.1.1, and the polypeptide that converts acetaldehyde to ethanol is classified as EC 1.1.1.1.

12. A method of producing lactate, the method comprising:

culturing the yeast cell of claim 1 to produce lactate.

13. The method of claim 12, wherein the method comprises:

collecting lactate from the culture.

14. The method of claim 12, wherein the culturing is performed under a condition within a range of pH 2 to 7.

15. A method for preparing a recombinant acid-resistant yeast cell of claim 1, the method comprising introducing into a yeast cell a genetic modification that increases the expression of a radiation sensitivity complementing kinase (RCK) in the yeast cell, wherein the yeast cell further comprises or is modified to comprise an exogenous polynucleotide encoding JEN1;
a polynucleotide encoding a lactate dehydrogenase; and deletion or disruption of:

a gene encoding a polypeptide that converts pyruvate to acetaldehyde;

a gene encoding a polypeptide that converts lactate to pyruvate;

a gene encoding a polypeptide that converts dihydroxyacetone phosphate (DHAP) to glycerol-3-phosphate;

a gene encoding NDE1 or NDE2, or both a gene encoding NDE1 and a gene encoding NDE2;

a gene encoding a mitochondrial pyruvate carrier (MPC);

a gene encoding a polypeptide that converts pyruvate to oxaloacetate;

a gene encoding a polypeptide that converts acetaldehyde to ethanol; and a gene encoding Fps1.

16. The method of claim 15, wherein the expression of a radiation sensitivity complementing kinase is increased by increasing the copy number of a polynucleotide encoding the radiation sensitivity complementing kinase, or by modifying an expression regulatory sequence of a gene encoding the radiation sensitivity complementing kinase.

17. The method of claim 15, wherein the expression of a radiation sensitivity complementing kinase is increased by introducing into the yeast cell an exogenous polynucleotide that encodes the radiation sensitivity complementing kinase.

* * * * *

SEQUENCE LISTING

<160> NUMBER OF SEQ ID NOS: 110

<210> SEQ ID NO 1
<211> LENGTH: 512
<212> TYPE: PRT
<213> ORGANISM: Saccharomyces cerevisiae

<400> SEQUENCE: 1

```
Met Ser Val Asn Pro Glu Phe Ile Ala Asp Gly Ile Asp Phe Tyr Pro
 1               5                  10                  15

Thr Thr Pro Asp Ala Ala Tyr Phe Asn Ala Ala Asp Gly Lys Asn Lys
             20                  25                  30

Val Asn Arg Ile Asn Gly Asn Ser Glu Asn Leu His His Ser Phe Ala
         35                  40                  45

Ser Gly Cys Arg Arg Ser Ser Leu Ser Val Asp Phe Asn Val Thr Ser
     50                  55                  60

Ser Asp Ser Glu Lys Ser Glu Gln Ser Cys Leu Glu Asn Asn Ser Gln
 65                  70                  75                  80

Glu Asp Glu Tyr Phe Cys Asp Ile Phe Ser Thr Glu Leu Lys Leu Asp
                 85                  90                  95

Glu Thr Ser Asn Lys Ser Thr Asp Tyr Ser Ser Asn His Gln Tyr
            100                 105                 110

Pro Glu Gln Leu Glu Leu His Asn Tyr Lys Leu Leu Asn Lys Ile Gly
        115                 120                 125

Glu Gly Ala Phe Ser Arg Val Phe Lys Ala Val Gly Ile Asn Thr Asp
    130                 135                 140

Asp Gln Ala Pro Val Ala Ile Lys Ala Ile Ile Lys Lys Gly Ile Ser
145                 150                 155                 160

Ser Asp Ala Ile Leu Lys Gly Asn Asp Arg Ile Gln Gly Ser Ser Arg
                165                 170                 175

Lys Lys Val Leu Asn Glu Val Ala Ile His Lys Leu Val Ser Lys Asn
            180                 185                 190

Asn Pro His Cys Thr Lys Phe Ile Ala Phe Gln Glu Ser Ala Asn Tyr
        195                 200                 205

Tyr Tyr Leu Val Thr Glu Leu Val Thr Gly Gly Glu Ile Phe Asp Arg
    210                 215                 220

Ile Val Gln Leu Thr Cys Phe Ser Glu Asp Leu Ala Arg His Val Ile
225                 230                 235                 240

Thr Gln Val Ala Ile Ala Ile Lys His Met His Tyr Met Gly Ile Val
                245                 250                 255

His Arg Asp Val Lys Pro Glu Asn Leu Leu Phe Glu Pro Ile Pro Phe
            260                 265                 270

Tyr Gly Leu Asp Gly Asp Met Gln Lys Glu Asp Glu Phe Thr Leu Gly
        275                 280                 285

Val Gly Gly Gly Ile Gly Leu Val Lys Leu Met Asp Phe Gly Leu
    290                 295                 300

Ala Lys Lys Leu Arg Asn Asn Thr Ala Lys Thr Pro Cys Gly Thr Ile
305                 310                 315                 320

Glu Tyr Val Ala Ser Glu Val Phe Thr Ser Lys Arg Tyr Ser Met Lys
                325                 330                 335

Val Asp Met Trp Ser Ile Gly Cys Val Leu Phe Thr Leu Leu Cys Gly
            340                 345                 350

Tyr Pro Pro Phe Tyr Glu Lys Asn Glu Lys Thr Leu Leu Lys Lys Ile
        355                 360                 365
```

```
Ser Arg Gly Asp Tyr Glu Phe Leu Ala Pro Trp Trp Asp Asn Ile Ser
    370                 375                 380

Ser Gly Ala Lys Asn Ala Val Thr His Leu Leu Glu Val Asp Pro Asn
385                 390                 395                 400

Lys Arg Tyr Asp Ile Asp Asp Phe Leu Asn Asp Pro Trp Leu Asn Ser
                405                 410                 415

Tyr Asp Cys Leu Lys Asp Ser Asn Ser Asn Ser Tyr Ala Ser Val Gln
                420                 425                 430

Ser Ile Leu Asn Asp Ser Phe Asp Glu Arg Ala Glu Thr Leu His Cys
            435                 440                 445

Ala Leu Ser Cys Gln Ser Glu Lys Gln Asp Asp Thr Glu Phe Ser Arg
450                 455                 460

Ser Glu Ser Ser Glu Tyr Ile Phe Met Thr Glu Glu Asp Arg Asn Leu
465                 470                 475                 480

Arg Gly Ser Trp Ile Gly Glu Pro Lys Glu Cys Phe Thr Leu Asp Leu
                485                 490                 495

Ala Thr Ser Ser Ile Tyr Arg Arg Arg Lys Asn Lys Ile Phe Phe Trp
                500                 505                 510

<210> SEQ ID NO 2
<211> LENGTH: 610
<212> TYPE: PRT
<213> ORGANISM: Saccharomyces cerevisiae

<400> SEQUENCE: 2

Met Leu Lys Ile Lys Ala Leu Phe Ser Lys Lys Pro Asp Gln Ala
  1               5                  10                  15

Asp Leu Ser Gln Glu Ser Lys Lys Pro Phe Lys Gly Lys Thr Arg Ser
                 20                  25                  30

Ser Gly Thr Asn Asn Lys Asp Val Ser Gln Ile Thr Ser Ser Pro Lys
             35                  40                  45

Lys Ser Phe Gln Asp Lys Asn Ile Val Gln Tyr Pro Ser Val Val Ala
 50                  55                  60

Asp Asp His His Met Lys Ser Leu Thr Asp Glu Leu Val Thr Thr Ile
 65                  70                  75                  80

Asp Ser Asp Ser Ser Pro Ser Asp Asn Ile Thr Thr Glu Asn Val Glu
                 85                  90                  95

Thr Val Thr Ser Val Pro Ala Ile Asp Val His Glu Ser Ser Glu Gly
                100                 105                 110

Gln Leu Ser Ser Asp Pro Leu Ile Ser Asp Glu Ser Leu Ser Glu Gln
            115                 120                 125

Ser Glu Ile Ile Ser Asp Ile Gln Asp Asp Ser Thr Asp Asp Asp Asn
130                 135                 140

Met Glu Asp Glu Ile Pro Glu Lys Ser Phe Leu Glu Gln Lys Glu Leu
145                 150                 155                 160

Ile Gly Tyr Lys Leu Ile Asn Lys Ile Gly Glu Gly Ala Phe Ser Lys
                165                 170                 175

Val Phe Arg Ala Ile Pro Ala Lys Asn Ser Ser Asn Glu Phe Leu Thr
                180                 185                 190

Lys Asn Tyr Lys Ala Val Ala Ile Lys Val Ile Lys Lys Ala Asp Leu
            195                 200                 205

Ser Ser Ile Asn Gly Asp His Arg Lys Lys Asp Lys Gly Lys Asp Ser
210                 215                 220

Thr Lys Thr Ser Ser Arg Asp Gln Val Leu Lys Glu Val Ala Leu His
225                 230                 235                 240
```

-continued

```
Lys Thr Val Ser Ala Gly Cys Ser Gln Ile Val Ala Phe Ile Asp Phe
                245                 250                 255
Gln Glu Thr Asp Ser Tyr Tyr Ile Ile Gln Glu Leu Leu Thr Gly
            260                 265                 270
Gly Glu Ile Phe Gly Glu Ile Val Arg Leu Thr Tyr Phe Ser Glu Asp
                275                 280                 285
Leu Ser Arg His Val Ile Lys Gln Leu Ala Leu Ala Val Lys His Met
    290                 295                 300
His Ser Leu Gly Val Val His Arg Asp Ile Lys Pro Glu Asn Leu Leu
305                 310                 315                 320
Phe Glu Pro Ile Glu Phe Thr Arg Ser Ile Lys Pro Lys Leu Arg Lys
                325                 330                 335
Ser Asp Asp Pro Gln Thr Lys Ala Asp Glu Gly Ile Phe Thr Pro Gly
                340                 345                 350
Val Gly Gly Gly Ile Gly Ile Val Lys Leu Ala Asp Phe Gly Leu
            355                 360                 365
Ser Lys Gln Ile Phe Ser Lys Asn Thr Lys Thr Pro Cys Gly Thr Val
    370                 375                 380
Gly Tyr Thr Ala Pro Glu Val Val Lys Asp Glu His Tyr Ser Met Lys
385                 390                 395                 400
Val Asp Met Trp Gly Ile Gly Cys Val Leu Tyr Thr Met Leu Cys Gly
                405                 410                 415
Phe Pro Pro Phe Tyr Asp Glu Lys Ile Asp Thr Leu Thr Glu Lys Ile
                420                 425                 430
Ser Arg Gly Glu Tyr Thr Phe Leu Lys Pro Trp Trp Asp Glu Ile Ser
    435                 440                 445
Ala Gly Ala Lys Asn Ala Val Ala Lys Leu Leu Glu Leu Glu Pro Ser
450                 455                 460
Lys Arg Tyr Asp Ile Asp Gln Phe Leu Asp Asp Pro Trp Leu Asn Thr
465                 470                 475                 480
Phe Asp Cys Leu Pro Lys Glu Gly Glu Ser Ser Gln Lys Lys Ala Gly
                485                 490                 495
Thr Ser Glu Arg Arg His Pro His Lys Lys Gln Phe Gln Leu Phe Gln
            500                 505                 510
Arg Asp Ser Ser Leu Leu Phe Ser Pro Ala Ala Val Ala Met Arg Asp
    515                 520                 525
Ala Phe Asp Ile Gly Asn Ala Val Lys Arg Thr Glu Glu Asp Arg Met
    530                 535                 540
Gly Thr Arg Gly Gly Leu Gly Ser Leu Ala Glu Asp Glu Leu Glu
545                 550                 555                 560
Asp Ser Tyr Ser Gly Ala Gln Gly Asp Glu Gln Leu Glu Gln Asn Met
                565                 570                 575
Phe Gln Leu Thr Leu Asp Thr Ser Thr Ile Leu Gln Arg Arg Lys Lys
            580                 585                 590
Val Gln Glu Asn Asp Val Gly Pro Thr Ile Pro Ile Ser Ala Thr Ile
    595                 600                 605
Arg Glu
    610

<210> SEQ ID NO 3
<211> LENGTH: 1539
<212> TYPE: DNA
<213> ORGANISM: Saccharomyces cerevisiae
```

<400> SEQUENCE: 3

```
atgtcagtaa acccagaatt tatagccgat ggcatcgatt tttatccaac aacgcccgat      60
gccgcgtatt tcaatgccgc tgatggtaaa aataaagtta acaggataaa tggtaactca     120
gaaaatttac accactcctt tgcatcgggt tgccgtagat catctctttc agtcgacttt     180
aatgttacct cgtccgattc agaaaaagt gaacagagct gcttggaaaa caactctcaa      240
gaagacgaat attttgtga cattttttcc actgaattaa aattagatga aacttctaac      300
aagtcaaccg attattccag ttcaaatcac cagtatcctg aacaactgga gttgcacaat     360
tataaactgc tcaataaaat tggtgaaggg gcattttcca gagtatttaa agcagtaggc     420
atcaacacgg atgaccaagc tcctgttgcc atcaaagcaa tcataaagaa aggcatttcg     480
agcgatgcca tcttaaaagg gaatgataga atccaaggtt ccagcagaaa gaaagtctta     540
aacgaagttg ccatccacaa actggtttcg aaaaataatc cgcattgtac aaaatttatc     600
gcattccagg aatcggcgaa ctactattac ttagtgacgg agttagtcac aggtggggaa     660
atatttgata ggatcgtcca actaacatgc tttagtgaag acttagctcg tcatgtcatt     720
actcaggtag caattgcaat taaacatatg cactacatgg gtattgtgca tcgtgatgtc     780
aaaccagaaa acctactatt tgaacccatc ccatttttatg gccttgatgg ggacatgcaa     840
aaagaagacg agtttacatt aggtgtcggc ggaggcggta ttggtttagt gaagctaatg     900
gacttcggac tagccaagaa acttcggaac aataccgcaa aaactccctg cggaacgata     960
gaatacgtcg catcagaagt attcacctcc aaacgatatt ccatgaaagt tgatatgtgg    1020
agtattggct gcgtactatt cacgttattg tgtggatatc ctccgtttta cgaaaagaac    1080
gaaaaaacat tattgaagaa aatatcgaga ggagattacg aattcttggc gccatggtgg    1140
gacaacataa gttctggcgc taagaacgca gttacccatc ttttggaggt tgacccaaac    1200
aagagatacg atatcgatga cttcctaaat gatccttggt taaattcgta cgattgtttg    1260
aaggattcaa actcaaattc ttatgccagc gtgcaaagca tactaaatga ttcattcgat    1320
gagagagcag agaccctaca ttgtgcatta agctgccaat ctgaaaaaca agatgacacc    1380
gagttttcca gaagtgaaag ctcggaatac atatttatga cggaagaaga cagaaaccta    1440
cggggcagtt ggatcggtga gccaaaagag tgttttacct tagaccttgc aacatcttct    1500
atataccgaa gaaggaagaa caagatattc ttctggtaa                            1539
```

<210> SEQ ID NO 4
<211> LENGTH: 1833
<212> TYPE: DNA
<213> ORGANISM: Saccharomyces cerevisiae

<400> SEQUENCE: 4

```
atgcttaaaa taaaggccct tttctcgaaa aagaaaccgg atcaggcaga tttgtctcag      60
gaatctaaaa aaccattcaa gggtaagacc aggtcaagcg gtacaaataa caaagatgtt     120
tcccagatta cttcttcccc taagaaaagc tttcaggaca aaaatatagt tcagtacccg     180
agtgttgtcg cagatgacca tcatatgaag tctttaaccg atgaattagt aaccacgata     240
gactcggact cttcaccgag tgataatatt accacggaaa atgtggaaac agttacttcc     300
gtgccagcta tcgatgtcca tgaaagtagt gaaggtcaat taagttccga ccccttaata     360
tctgacgaat ctctttcgga acaaagcgag attatcagtg atatccagga tgacagtact     420
gatgatgaca atatgtgaaga tgaaattccg gaaaaatcct tcctcgaaca aaaggaattg     480
ataggttaca agctgatcaa taaaatcggt gaaggtgctt tttcaaaagt ctttagagcc     540
```

```
atacctgcta aaaatagttc taatgaattt ttaactaaaa actataaagc tgttgccatt    600
aaagttatca aaaaggcaga tttatcctcg attaatggtg atcatcgtaa aaggacaaa     660
gggaaggaca gcactaaaac ttcttccaga gatcaagtct tgaaggaagt tgcactacat    720
aagacggttt ccgctggttg ttcacaaatt gtcgcgttca tagacttcca agaaacagat    780
agctattatt atattattca agagttacta accggtgggg aaatcttcgg cgaaattgtt    840
aggttgacct atttcagtga agatttatca aggcatgtaa tcaaacaatt agcactggct    900
gttaaacata tgcattcact aggtgtagtg catcgtgata taaaacctga aatcttctt    960
tttgaaccga ttgaattcac acgctctata aaaccaaaat tgaggaaatc ggatgatccg    1020
caaacaaagg cagacgaggg aattttcaca ccaggagttg gtggtggtgg aattggtata    1080
gtaaaactag ctgattttgg tttgtctaaa caaatatttt ccaagaacac caagactcct    1140
tgtggtacag tcggttacac tgcccctgaa gttgtcaaag atgagcatta ttctatgaaa    1200
gtggatatgt gggggattgg ttgcgttttg tacacaatgt tatgtgggtt cccgccattc    1260
tatgatgaga aaattgacac tttaactgaa aaaatatcaa ggggtgagta taccctttctg   1320
aaaccttggt gggatgaaat cagcgccggt gccaagaatg ccgtggctaa gctattagaa    1380
ctagagccgt ctaaaagata cgacattgac cagttttggt acgacccatg gttaaataca    1440
ttcgattgtt taccaaagga gggcgaatct tcacaaaaga aagcaggtac ttccgaaaga    1500
cgccatccgc ataagaaaca attccaacta tttcaaagag actcctcgct actgttttca    1560
ccagctgctg ttgctatgcg tgacgccttt gatattggta atgctgtgaa acgtaccgaa    1620
gaagaccgta tgggaacacg tggaggatta ggctcgcttg ctgaggacga agaattggaa    1680
gatagttaca gtggcgccca aggcgatgaa cagctggaac aaaatatgtt ccaattaacg    1740
ctggatacgt ccacgattct gcaaagaaga aaaaaagttc aagaaaatga cgtagggcct    1800
acaattccaa taagcgccac tatcagggaa tag                                 1833
```

<210> SEQ ID NO 5
<211> LENGTH: 332
<212> TYPE: PRT
<213> ORGANISM: Pelodiscus sinensis japonicus

<400> SEQUENCE: 5

```
Met Ser Val Lys Glu Leu Leu Ile Gln Asn Val His Lys Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Arg Gly Glu Met Leu Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140
```

```
Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 6
<211> LENGTH: 332
<212> TYPE: PRT
<213> ORGANISM: Ornithorhynchus anatinus

<400> SEQUENCE: 6

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
        50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
```

```
            180                 185                 190
His Gly Asp Ser Ser Val Pro Val Trp Ser Gly Val Asn Val Ala Gly
            195                 200                 205

Val Ser Leu Lys Asn Leu His Pro Asp Leu Gly Thr Asp Ala Asp Lys
        210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
            290                 295                 300

Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 7
<211> LENGTH: 332
<212> TYPE: PRT
<213> ORGANISM: Tursiops truncatus

<400> SEQUENCE: 7

Met Ala Thr Val Lys Asp Gln Leu Ile Gln Asn Leu Leu Lys Glu Glu
1               5                   10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220
```

```
Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
            245                 250                 255

Ala Asp Leu Ala Glu Ser Ile Met Lys Asn Leu Arg Arg Val His Pro
        260                 265                 270

Ile Ser Thr Met Ile Lys Gly Leu Tyr Gly Ile Lys Glu Asp Val Phe
    275                 280                 285

Leu Ser Val Pro Cys Ile Leu Gly Gln Asn Gly Ile Ser Asp Val Val
290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
            325                 330
```

<210> SEQ ID NO 8
<211> LENGTH: 332
<212> TYPE: PRT
<213> ORGANISM: Rattus norvegicus

<400> SEQUENCE: 8

```
Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270
```

Ile Ser Thr Met Ile Lys Gly Leu Tyr Gly Ile Lys Glu Asp Val Phe
             275                 280                 285

Leu Ser Val Pro Cys Ile Leu Gly Gln Asn Gly Ile Ser Asp Val Val
290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
             325                 330

<210> SEQ ID NO 9
<211> LENGTH: 332
<212> TYPE: PRT
<213> ORGANISM: Bos Taurus

<400> SEQUENCE: 9

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
             35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65              70                  75                  80

Lys Asp Tyr Asn Val Thr Ala Asn Ser Arg Leu Val Ile Ile Thr Ala
             85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
            115                 120                 125

Pro Asn Cys Lys Leu Leu Val Val Ser Asn Pro Val Asp Ile Leu Thr
            130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
            165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
            195                 200                 205

Val Ser Leu Lys Asn Leu His Pro Glu Leu Gly Thr Asp Ala Asp Lys
            210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
            245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
290                 295                 300

Lys Val Thr Leu Thr His Glu Glu Glu Ala Cys Leu Lys Lys Ser Ala

Asp Thr Leu Trp Gly Ile Gln Lys Glu Leu Gln Phe
            325                 330

<210> SEQ ID NO 10
<211> LENGTH: 999
<212> TYPE: DNA
<213> ORGANISM: Pelodiscus sinensis japonicus

<400> SEQUENCE: 10

| | | | | | |
|---|---|---|---|---|---|
| atgtccgtaa | aggaactact | tatacaaaac | gtccataagg | aggagcattc | tcacgctcac | 60 |
| aataagataa | cagttgtagg | agtaggtgca | gtaggtatgg | catgtgctat | ttcgatatta | 120 |
| atgaaagact | tggctgatga | actagccttg | gttgatgtga | ttgaggataa | gttacgtgga | 180 |
| gaaatgttag | atttgcaaca | tggttcattg | ttcttgagaa | ccccccaaaat | tgtctcgggt | 240 |
| aaggattatt | cagtcactgc | tcattctaaa | ctggttatca | ttacagcagg | tgcaagacag | 300 |
| caagaagggg | agagcagact | aaatctggtt | caacgtaatg | tcaacatctt | caagtttatc | 360 |
| atcccgaacg | tagtaaaata | cagtccagac | tgcatgttgc | ttgttgtgag | taatccagtt | 420 |
| gacatcttaa | cctatgttgc | gtggaaaatc | agtgggtttc | caaaacatag | ggtgattggc | 480 |
| tcaggatgca | accttgatag | cgccaggttt | aggtatctaa | tgggagaaaa | attaggtatt | 540 |
| cactccttat | cttgtcatgg | ctggataata | ggcgaacatg | gtgattcttc | ggtacctgtt | 600 |
| tggtccgggg | ttaatgtggc | tggtgttagt | ttaaaagcat | tatatcctga | cctgggtact | 660 |
| gatgccgata | agaacattg | gaaagaagtg | cacaaacaag | tggttgattc | tgcttacgaa | 720 |
| gttattaaac | ttaagggcta | cacttcttgg | gctataggtc | tatcagtagc | tgatttggca | 780 |
| gaaaccgtta | tgaaaaattt | aagaagagtc | cacccaattt | ccacgatggt | caagggtatg | 840 |
| tacggtgtta | gctctgacgt | cttcttatct | gttccttgtg | ttttgggata | tgcgggaatt | 900 |
| acagacgtcg | tgaagatgac | attgaaatca | gaggaagagg | aaaaactaag | aaagtcagcc | 960 |
| gatactctgt | ggggcattca | aaaggaattg | cagttttaa | | | 999 |

<210> SEQ ID NO 11
<211> LENGTH: 999
<212> TYPE: DNA
<213> ORGANISM: Bos Taurus

<400> SEQUENCE: 11

| | | | | | |
|---|---|---|---|---|---|
| atggcaacat | taaagatca | actaatccag | aatttgttga | agaggagca | tgttccacaa | 60 |
| aacaaaatca | caatcgtcgg | cgtaggtgca | gtaggtatgg | cttgtgccat | atccatcttg | 120 |
| atgaaagact | tagctgatga | ggtcgcgctg | gttgatgtaa | tggaggacaa | acttaaagga | 180 |
| gaaatgatgg | atcttcaaca | tggttcactc | tttttgagaa | ctcctaaaat | tgtatccggg | 240 |
| aaagattata | acgttaccgc | caattctaga | cttgttataa | tcacggctgg | tgcaagacaa | 300 |
| caggaaggcg | aatcaagact | taacttagtt | cagagaaacg | taaacatttt | caagtttatc | 360 |
| atcccaaata | ttgtaaaata | ctccccaaat | tgcaagttgc | tggttgtttc | aaatcctgtt | 420 |
| gacatattga | cttacgttgc | ttggaagatt | tcaggtttcc | caaagaatag | agtaatcgga | 480 |
| tctggttgca | atctcgattc | tgctcgtttt | aggtatctga | tgggtgaaag | attagggggtt | 540 |
| catccattga | gttgtcacgg | atggattcta | ggtgaacatg | gagatagttc | tgtgcctgtt | 600 |
| tggtcaggtg | tcaacgtagc | aggtgtctct | ttgaaaaatc | tacacccaga | actaggaaca | 660 |
| gatgccgaca | aggaacaatg | gaaggccgtc | cacaaacaag | tggtggattc | tgcctacgaa | 720 |

```
gtcatcaaat tgaagggcta cacatcttgg gcaattggct tatccgtcgc tgatctggct    780
gaatcaataa tgaaaaacct ccgtagagtg catcctataa gtactatgat taagggttta    840
tacgggatca aggaagatgt ttttctatct gtgccatgta ttttgggcca aaatggaatt    900
tctgacgttg ttaaagtgac acttactcat gaagaggaag cgtgtttgaa aaagagcgca    960
gacaccttat ggggcatcca aaaggaatta caattctaa                           999
```

<210> SEQ ID NO 12
<211> LENGTH: 563
<212> TYPE: PRT
<213> ORGANISM: Saccharomyces cerevisiae

<400> SEQUENCE: 12

```
Met Ser Glu Ile Thr Leu Gly Lys Tyr Leu Phe Glu Arg Leu Lys Gln
 1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
```

|     |     |     |     |     | 325 |     |     |     |     | 330 |     |     |     |     | 335 |     |
| --- | --- | --- | --- | --- | --- | --- | --- | --- | --- | --- | --- | --- | --- | --- | --- | --- |
| Ile | Ala | Asp | Ala | Ala | Lys | Gly | Tyr | Lys | Pro | Val | Ala | Val | Pro | Ala | Arg |
|     |     |     | 340 |     |     |     |     | 345 |     |     |     |     | 350 |     |     |
| Thr | Pro | Ala | Asn | Ala | Ala | Val | Pro | Ala | Ser | Thr | Pro | Leu | Lys | Gln | Glu |
|     |     |     | 355 |     |     |     |     | 360 |     |     |     |     | 365 |     |     |
| Trp | Met | Trp | Asn | Gln | Leu | Gly | Asn | Phe | Leu | Gln | Glu | Gly | Asp | Val | Val |
|     |     | 370 |     |     |     |     | 375 |     |     |     |     | 380 |     |     |     |
| Ile | Ala | Glu | Thr | Gly | Thr | Ser | Ala | Phe | Gly | Ile | Asn | Gln | Thr | Thr | Phe |
| 385 |     |     |     |     | 390 |     |     |     |     | 395 |     |     |     |     | 400 |
| Pro | Asn | Asn | Thr | Tyr | Gly | Ile | Ser | Gln | Val | Leu | Trp | Gly | Ser | Ile | Gly |
|     |     |     |     | 405 |     |     |     |     | 410 |     |     |     |     | 415 |     |
| Phe | Thr | Thr | Gly | Ala | Thr | Leu | Gly | Ala | Ala | Phe | Ala | Ala | Glu | Glu | Ile |
|     |     |     | 420 |     |     |     |     | 425 |     |     |     |     | 430 |     |     |
| Asp | Pro | Lys | Lys | Arg | Val | Ile | Leu | Phe | Ile | Gly | Asp | Gly | Ser | Leu | Gln |
|     |     |     | 435 |     |     |     |     | 440 |     |     |     |     | 445 |     |     |
| Leu | Thr | Val | Gln | Glu | Ile | Ser | Thr | Met | Ile | Arg | Trp | Gly | Leu | Lys | Pro |
|     | 450 |     |     |     |     | 455 |     |     |     |     | 460 |     |     |     |     |
| Tyr | Leu | Phe | Val | Leu | Asn | Asn | Asp | Gly | Tyr | Thr | Ile | Glu | Lys | Leu | Ile |
| 465 |     |     |     |     | 470 |     |     |     |     | 475 |     |     |     |     | 480 |
| His | Gly | Pro | Lys | Ala | Gln | Tyr | Asn | Glu | Ile | Gln | Gly | Trp | Asp | His | Leu |
|     |     |     |     | 485 |     |     |     |     | 490 |     |     |     |     | 495 |     |
| Ser | Leu | Leu | Pro | Thr | Phe | Gly | Ala | Lys | Asp | Tyr | Glu | Thr | His | Arg | Val |
|     |     |     | 500 |     |     |     |     | 505 |     |     |     |     | 510 |     |     |
| Ala | Thr | Thr | Gly | Glu | Trp | Asp | Lys | Leu | Thr | Gln | Asp | Lys | Ser | Phe | Asn |
|     |     | 515 |     |     |     |     | 520 |     |     |     |     | 525 |     |     |     |
| Asp | Asn | Ser | Lys | Ile | Arg | Met | Ile | Glu | Ile | Met | Leu | Pro | Val | Phe | Asp |
|     | 530 |     |     |     |     | 535 |     |     |     |     | 540 |     |     |     |     |
| Ala | Pro | Gln | Asn | Leu | Val | Glu | Gln | Ala | Lys | Leu | Thr | Ala | Ala | Thr | Asn |
| 545 |     |     |     |     | 550 |     |     |     |     | 555 |     |     |     |     | 560 |
| Ala | Lys | Gln |     |     |     |     |     |     |     |     |     |     |     |     |     |

<210> SEQ ID NO 13
<211> LENGTH: 1692
<212> TYPE: DNA
<213> ORGANISM: Saccharomyces cerevisiae

<400> SEQUENCE: 13

```
atgtctgaaa ttactttggg taaatatttg ttcgaaagat aaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact tgaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
```

-continued

```
ggtgtttacg tcggtacctt gtccaagcca gaagttaagg aagccgttga atctgctgac   840
ttgattttgt ctgtcggtgc tttgttgtct gatttcaaca ccggttcttt ctcttactct   900
tacaagacca agaacattgt cgaattccac tccgaccaca tgaagatcag aaacgccact   960
ttcccaggtg tccaaatgaa attcgttttg caaaagttgt tgaccactat tgctgacgcc  1020
gctaagggtt acaagccagt tgctgtccca gctagaactc cagctaacgc tgctgtccca  1080
gcttctaccc cattgaagca agaatggatg tggaaccaat tgggtaactt cttgcaagaa  1140
ggtgatgttg tcattgctga accggtaccc tccgctttcg gtatcaacca aaccactttc  1200
ccaaacaaca cctacggtat ctctcaagtc ttatggggtt ccattggttt caccactggt  1260
gctaccttgg gtgctgcttt cgctgctgaa gaaattgatc caagaagag agttatctta  1320
ttcattggtg acggttcttt gcaattgact gttcaagaaa tctccaccat gatcagatgg  1380
ggcttgaagc catacttgtt cgtcttgaac aacgatggtt acaccattga aagttgatt  1440
cacggtccaa aggctcaata caacgaaatt caaggttggg accacctatc cttgttgcca  1500
actttcggtg ctaaggacta tgaaacccac agagtcgcta ccaccggtga atgggacaag  1560
ttgacccaag acaagtcttt caacgacaac tctaagatca gaatgattga aatcatgttg  1620
ccagtcttcg atgctccaca aaacttggtt gaacaagcta agttgactgc tgctaccaac  1680
gctaagcaat aa                                                      1692
```

<210> SEQ ID NO 14
<211> LENGTH: 591
<212> TYPE: PRT
<213> ORGANISM: Saccharomyces cerevisiae

<400> SEQUENCE: 14

```
Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
             20                  25                  30

Gly Ser Thr Val Pro Lys Ser Lys Ser Phe Glu Gln Asp Ser Arg Lys
         35                  40                  45

Arg Thr Gln Ser Trp Thr Ala Leu Arg Val Gly Ala Ile Leu Ala Ala
     50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                 85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205
```

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
    435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 15
<211> LENGTH: 1776
<212> TYPE: DNA
<213> ORGANISM: Saccharomyces cerevisiae

<400> SEQUENCE: 15

```
atgctaaaat acaaaccttt actaaaaatc tcgaagaact gtgaggctgc tatcctcaga    60
gcgtctaaga ctagattgaa cacaatccgc gcgtacggtt ctaccgttcc aaaatccaag   120
tcgttcgaac aagactcaag aaaacgcaca cagtcatgga ctgccttgag agtcggtgca   180
attctagccg ctactagttc cgtggcgtat ctaaactggc ataatggcca aatagacaac   240
gagccgaaac tggatatgaa taaacaaaag atttcgcccg ctgaagttgc caagcataac   300
aagcccgatg attgttgggt tgtgatcaat ggttacgtat acgacttaac gcgattccta   360
ccaaatcatc caggtgggca ggatgttatc aagtttaacg ccgggaaaga tgtcactgct   420
attttgaac cactacatgc tcctaatgtc atcgataagt atatagctcc cgagaaaaaa   480
ttgggtcccc ttcaaggatc catgcctcct gaacttgtct gtcctcctta tgctcctggt   540
gaaactaagg aagatatcgc tagaaaagaa caactaaaat cgctgctacc tcctctagat   600
aatattatta acctttacga ctttgaatac ttggcctctc aaactttgac taaacaagcg   660
tgggcctact attcctccgg tgctaacgac gaagttactc acagagaaaa ccataatgct   720
tatcatagga tttttttcaa accaaagatc cttgtagatg tacgcaaagt agacatttca   780
actgacatgt tgggttctca tgtggatgtt cccttctacg tgtctgctac agctttgtgt   840
aaactgggaa acccttaga aggtgaaaaa gatgtcgcca gaggttgtgg ccaaggtgtg   900
acaaaagtcc cacaaatgat atctactttg gcttcatgtt cccctgagga aattattgaa   960
gcagcaccct ctgataaaca aattcaatgg taccaactat atgttaactc tgatagaaag  1020
atcactgatg atttggttaa aaatgtagaa aagctgggtg taaaggcatt atttgtcact  1080
gtggatgctc caagtttagg tcaaagagaa aaagatatga agctgaaatt ttccaataca  1140
aaggctggtc caaaagcgat gaagaaaact aatgtagaag aatctcaagg tgcttcgaga  1200
gcgttatcaa agtttattga ccccctcttg acttggaaag atatagaaga gttgaagaaa  1260
aagacaaaac tacctattgt tatcaaaggt gttcaacgta ccgaagatgt tatcaaagca  1320
gcagaaatcg gtgtaagtgg ggtggttcta tccaatcatg gtggtagaca attagatttt  1380
tcaagggctc ccattgaagt cctggctgaa accatgccaa tcctggaaca acgtaacttg  1440
aaggataagt tggaagtttt cgtggacggt ggtgttcgtc gtggtacaga tgtcttgaaa  1500
gcgttatgtc taggtgctaa aggtgttggt ttgggtagac cattcttgta tgcgaactca  1560
tgctatggtc gtaatggtgt tgaaaaagcc attgaaattt taagagatga aattgaaatg  1620
tctatgagac tattaggtgt tactagcatt gcggaattga gcctgatct tttagatcta  1680
tcaacactaa aggcaagaac agttggagta ccaaacgacg tgctgtataa tgaagtttat  1740
gagggaccta ctttaacaga atttgaggat gcatga                            1776
```

<210> SEQ ID NO 16
<211> LENGTH: 391
<212> TYPE: PRT
<213> ORGANISM: Saccharomyces cerevisiae

<400> SEQUENCE: 16

```
Met Ser Ala Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
                 20                  25                  30

Lys Pro Phe Lys Val Thr Val Ile Gly Ser Gly Asn Trp Gly Thr Thr
             35                  40                  45
```

| | | | | | | | | | | | |
|---|---|---|---|---|---|---|---|---|---|---|---|
|Ile|Ala|Lys|Val|Val|Ala|Glu|Asn|Cys|Lys|Gly|Tyr|Pro|Glu|Val|Phe|
| |50| | | |55| | | |60| | |

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
            290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 17
<211> LENGTH: 1176
<212> TYPE: DNA
<213> ORGANISM: Saccharomyces cerevisiae

<400> SEQUENCE: 17
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180

-continued

```
ccagaagttt tcgctccaat agtacaaatg tgggtgttcg aagaagagat caatggtgaa      240
aaattgactg aaatcataaa tactagacat caaaacgtga atacttgcc tggcatcact       300 ctacccgaca atttggttgc taatccagac ttgattgatt cagtcaagga tgtcgacatc      360
atcgttttca acattccaca tcaattttg ccccgtatct gtagccaatt gaaaggtcat       420
gttgattcac acgtcagagc tatctcctgt ctaaagggtt ttgaagttgg tgctaaaggt       480
gtccaattgc tatcctctta catcactgag gaactaggta ttcaatgtgg tgctctatct       540
ggtgctaaca ttgccaccga agtcgctcaa gaacactggt ctgaaacaac agttgcttac       600
cacattccaa aggatttcag aggcgagggc aaggacgtcg accataaggt tctaaaggcc       660
ttgttccaca gaccttactt ccacgttagt gtcatcgaag atgttgctgg tatctccatc       720
tgtggtgctt tgaagaacgt tgttgcctta ggttgtggtt tcgtcgaagg tctaggctgg       780
ggtaacaacg cttctgctgc catccaaaga gtcggtttgg gtgagatcat cagattcggt       840
caaatgtttt tcccagaatc tagagaagaa acatactacc aagagtctgc tggtgttgct       900
gatttgatca ccacctgcgc tggtggtaga aacgtcaagg ttgctaggct aatggctact       960
tctggtaagg acgcctggga atgtgaaaag gagttgttga atggccaatc cgctcaaggt      1020
ttaattacct gcaaagaagt tcacgaatgg ttggaaacat gtggctctgt cgaagacttc      1080
ccattatttg aagccgtata ccaaatcgtt tacaacaact acccaatgaa gaacctgccg      1140
gacatgattg aagaattaga tctacatgaa gattag                                1176

<210> SEQ ID NO 18
<211> LENGTH: 591
<212> TYPE: PRT
<213> ORGANISM: Saccharomyces cerevisiae

<400> SEQUENCE: 18

Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190
```

Lys Ser Leu Leu Pro Pro Leu Asp Asn Ile Ile Asn Leu Tyr Asp Phe
            195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
    275                 280                 285

Glu Lys Asp Val Ala Arg Gly Cys Gly Gln Gly Val Thr Lys Val Pro
290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
    355                 360                 365

Arg Glu Lys Asp Met Lys Leu Lys Phe Ser Asn Thr Lys Ala Gly Pro
370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
    435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
    515                 520                 525

Lys Ala Ile Glu Ile Leu Arg Asp Glu Ile Glu Met Ser Met Arg Leu
530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 19
<211> LENGTH: 391
<212> TYPE: PRT

<213> ORGANISM: Saccharomyces cerevisiae

<400> SEQUENCE: 19

```
Met Ser Ala Ala Ala Asp Arg Leu Asn Leu Thr Ser Gly His Leu Asn
  1               5                  10                  15
Ala Gly Arg Lys Arg Ser Ser Ser Val Ser Leu Lys Ala Ala Glu
             20                  25                  30
Lys Pro Phe Lys Val Thr Val Ile Gly Ser Gly Asn Trp Gly Thr Thr
             35                  40                  45
Ile Ala Lys Val Val Ala Glu Asn Cys Lys Gly Tyr Pro Glu Val Phe
     50                  55                  60
Ala Pro Ile Val Gln Met Trp Val Phe Glu Glu Ile Asn Gly Glu
 65                  70                  75                  80
Lys Leu Thr Glu Ile Ile Asn Thr Arg His Gln Asn Val Lys Tyr Leu
                 85                  90                  95
Pro Gly Ile Thr Leu Pro Asp Asn Leu Val Ala Asn Pro Asp Leu Ile
             100                 105                 110
Asp Ser Val Lys Asp Val Asp Ile Ile Val Phe Asn Ile Pro His Gln
             115                 120                 125
Phe Leu Pro Arg Ile Cys Ser Gln Leu Lys Gly His Val Asp Ser His
 130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                 165                 170                 175
Gly Ala Leu Ser Gly Ala Asn Ile Ala Thr Glu Val Ala Gln Glu His
             180                 185                 190
Trp Ser Glu Thr Thr Val Ala Tyr His Ile Pro Lys Asp Phe Arg Gly
             195                 200                 205
Glu Gly Lys Asp Val Asp His Lys Val Leu Lys Ala Leu Phe His Arg
 210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                 245                 250                 255
Gly Leu Gly Trp Gly Asn Asn Ala Ser Ala Ala Ile Gln Arg Val Gly
             260                 265                 270
Leu Gly Glu Ile Ile Arg Phe Gly Gln Met Phe Phe Pro Glu Ser Arg
         275                 280                 285
Glu Glu Thr Tyr Tyr Gln Glu Ser Ala Gly Val Ala Asp Leu Ile Thr
 290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                 325                 330                 335
Ser Ala Gln Gly Leu Ile Thr Cys Lys Glu Val His Glu Trp Leu Glu
             340                 345                 350
Thr Cys Gly Ser Val Glu Asp Phe Pro Leu Phe Glu Ala Val Tyr Gln
         355                 360                 365
Ile Val Tyr Asn Asn Tyr Pro Met Lys Asn Leu Pro Asp Met Ile Glu
 370                 375                 380
Glu Leu Asp Leu His Glu Asp
385                 390
```

<210> SEQ ID NO 20
<211> LENGTH: 1776
<212> TYPE: DNA
<213> ORGANISM: Saccharomyces cerevisiae

<400> SEQUENCE: 20

| | | | | | | |
|---|---|---|---|---|---|---|
| atgctaaaat | acaaaccttt | actaaaaatc | tcgaagaact | gtgaggctgc | tatcctcaga | 60 |
| gcgtctaaga | ctagattgaa | cacaatccgc | gcgtacggtt | ctaccgttcc | aaaatccaag | 120 |
| tcgttcgaac | aagactcaag | aaaacgcaca | cagtcatgga | ctgccttgag | agtcggtgca | 180 |
| attctagccg | ctactagttc | cgtggcgtat | ctaaactggc | ataatggcca | aatagacaac | 240 |
| gagccgaaac | tggatatgaa | taaacaaaag | atttcgcccg | ctgaagttgc | caagcataac | 300 |
| aagcccgatg | attgttgggt | tgtgatcaat | ggttacgtat | acgacttaac | gcgattccta | 360 |
| ccaaatcatc | caggtgggca | ggatgttatc | aagtttaacg | ccgggaaaga | tgtcactgct | 420 |
| attttttgaac | cactacatgc | tcctaatgtc | atcgataagt | atatagctcc | cgagaaaaaa | 480 |
| ttgggtcccc | ttcaaggatc | catgcctcct | gaacttgtct | gtcctcctta | tgctcctggt | 540 |
| gaaactaagg | aagatatcgc | tagaaaagaa | caactaaaat | cgctgctacc | tcctctagat | 600 |
| aatattatta | acctttacga | ctttgaatac | ttggcctctc | aaactttgac | taaacaagcg | 660 |
| tgggcctact | attcctccgg | tgctaacgac | gaagttactc | acagagaaaa | ccataatgct | 720 |
| tatcatagga | ttttttttcaa | accaaagatc | cttgtagatg | tacgcaaagt | agacatttca | 780 |
| actgacatgt | tgggttctca | tgtggatgtt | cccttctacg | tgtctgctac | agctttgtgt | 840 |
| aaactgggaa | accccttaga | aggtgaaaaa | gatgtcgcca | gaggttgtgg | ccaaggtgtg | 900 |
| acaaaagtcc | cacaaatgat | atctactttg | gcttcatgtt | cccctgagga | aattattgaa | 960 |
| gcagcaccct | ctgataaaca | aattcaatgg | taccaactat | atgttaactc | tgatagaaag | 1020 |
| atcactgatg | atttggttaa | aaatgtagaa | aagctgggtg | taaaggcatt | atttgtcact | 1080 |
| gtggatgctc | caagtttagg | tcaaagagaa | aaagatatga | agctgaaatt | ttccaataca | 1140 |
| aaggctggtc | caaaagcgat | gaagaaaact | aatgtagaag | aatctcaagg | tgcttcgaga | 1200 |
| gcgttatcaa | agtttattga | ccccctctttg | acttggaaag | atatagaaga | gttgaagaaa | 1260 |
| aagacaaaac | tacctattgt | tatcaaaggt | gttcaacgta | ccgaagatgt | tatcaaagca | 1320 |
| gcagaaatcg | gtgtaagtgg | ggtggttcta | tccaatcatg | tggtagaca | attagatttt | 1380 |
| tcaagggctc | ccattgaagt | cctggctgaa | accatgccaa | tcctggaaca | acgtaacttg | 1440 |
| aaggataagt | tggaagtttt | cgtggacggt | ggtgttcgtc | gtggtacaga | tgtcttgaaa | 1500 |
| gcgttatgtc | taggtgctaa | aggtgttggt | ttgggtagac | cattcttgta | tgcgaactca | 1560 |
| tgctatggtc | gtaatggtgt | tgaaaaagcc | attgaaattt | taagagatga | aattgaaatg | 1620 |
| tctatgagac | tattaggtgt | tactagcatt | gcggaattga | agcctgatct | tttagatcta | 1680 |
| tcaacactaa | aggcaagaac | agttggagta | ccaaacgacg | tgctgtataa | tgaagtttat | 1740 |
| gagggaccta | ctttaacaga | atttgaggat | gcatga | | | 1776 |

<210> SEQ ID NO 21
<211> LENGTH: 1176
<212> TYPE: DNA
<213> ORGANISM: Saccharomyces cerevisiae

<400> SEQUENCE: 21

| | | | | | | |
|---|---|---|---|---|---|---|
| atgtctgctg | ctgctgatag | attaaactta | acttccggcc | acttgaatgc | tggtagaaag | 60 |
| agaagttcct | cttctgtttc | tttgaaggct | gccgaaaagc | ctttcaaggt | tactgtgatt | 120 |

```
ggatctggta actggggtac tactattgcc aaggtggttg ccgaaaattg taagggatac      180
ccagaagttt tcgctccaat agtacaaatg tgggtgttcg aagaagagat caatggtgaa      240
aaattgactg aaatcataaa tactagacat caaaacgtga atacttgcc tggcatcact       300 ctacccgaca atttggttgc taatccagac ttgattgatt cagtcaagga tgtcgacatc      360
atcgttttca acattccaca tcaattttg ccccgtatct gtagccaatt gaaaggtcat       420
gttgattcac acgtcagagc tatctcctgt ctaaagggtt ttgaagttgg tgctaaaggt      480
gtccaattgc tatcctctta catcactgag gaactaggta ttcaatgtgg tgctctatct      540
ggtgctaaca ttgccaccga agtcgctcaa gaacactggt ctgaaacaac agttgcttac     600
cacattccaa aggatttcag aggcgagggc aaggacgtcg accataaggt tctaaaggcc      660
ttgttccaca gacctactt ccacgttagt gtcatcgaag atgttgctgg tatctccatc       720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact    960
tctggtaagg acgcctggga atgtgaaaag gagttgttga atggccaatc cgctcaaggt     1020
ttaattacct gcaaagaagt tcacgaatgg ttggaaacat gtggctctgt cgaagacttc     1080
ccattatttg aagccgtata ccaaatcgtt tacaacaact acccaatgaa gaacctgccg     1140
gacatgattg aagaattaga tctacatgaa gattag                               1176

<210> SEQ ID NO 22
<211> LENGTH: 560
<212> TYPE: PRT
<213> ORGANISM: Saccharomyces cerevisiae

<400> SEQUENCE: 22

Met Ile Arg Gln Ser Leu Met Lys Thr Val Trp Ala Asn Ser Ser Arg
1               5                   10                  15

Phe Ser Leu Gln Ser Lys Ser Gly Leu Val Lys Tyr Ala Lys Asn Arg
            20                  25                  30

Ser Phe His Ala Ala Arg Asn Leu Leu Glu Asp Lys Lys Val Ile Leu
        35                  40                  45

Gln Lys Val Ala Pro Thr Thr Gly Val Val Ala Lys Gln Ser Phe Phe
    50                  55                  60

Lys Arg Thr Gly Lys Phe Thr Leu Lys Ala Leu Leu Tyr Ser Ala Leu
65                  70                  75                  80

Ala Gly Thr Ala Tyr Val Ser Tyr Ser Leu Tyr Arg Glu Ala Asn Pro
                85                  90                  95

Ser Thr Gln Val Pro Gln Ser Asp Thr Phe Pro Asn Gly Ser Lys Arg
            100                 105                 110

Lys Thr Leu Val Ile Leu Gly Ser Gly Trp Gly Ser Val Ser Leu Leu
        115                 120                 125

Lys Asn Leu Asp Thr Thr Leu Tyr Asn Val Val Val Ser Pro Arg
    130                 135                 140

Asn Tyr Phe Leu Phe Thr Pro Leu Leu Pro Ser Thr Pro Val Gly Thr
145                 150                 155                 160

Ile Glu Leu Lys Ser Ile Val Glu Pro Val Arg Thr Ile Ala Arg Arg
                165                 170                 175

Ser His Gly Glu Val His Tyr Tyr Glu Ala Glu Ala Tyr Asp Val Asp
```

180                 185                 190
Pro Glu Asn Lys Thr Ile Lys Val Lys Ser Ser Ala Lys Asn Asn Asp
                195                 200                 205
Tyr Asp Leu Asp Leu Lys Tyr Asp Tyr Leu Val Val Gly Val Gly Ala
            210                 215                 220
Gln Pro Asn Thr Phe Gly Thr Pro Gly Val Tyr Glu Tyr Ser Ser Phe
225                 230                 235                 240
Leu Lys Glu Ile Ser Asp Ala Gln Glu Ile Arg Leu Lys Ile Met Ser
                245                 250                 255
Ser Ile Glu Lys Ala Ala Ser Leu Ser Pro Lys Asp Pro Glu Arg Ala
            260                 265                 270
Arg Leu Leu Ser Phe Val Val Gly Gly Pro Thr Gly Val Glu
        275                 280                 285
Phe Ala Ala Glu Leu Arg Asp Tyr Val Asp Gln Asp Leu Arg Lys Trp
        290                 295                 300
Met Pro Glu Leu Ser Lys Glu Ile Lys Val Thr Leu Val Glu Ala Leu
305                 310                 315                 320
Pro Asn Ile Leu Asn Met Phe Asp Lys Tyr Leu Val Asp Tyr Ala Gln
                325                 330                 335
Asp Leu Phe Lys Glu Glu Lys Ile Asp Leu Arg Leu Lys Thr Met Val
            340                 345                 350
Lys Lys Val Asp Ala Thr Thr Ile Thr Ala Lys Thr Gly Asp Gly Asp
        355                 360                 365
Ile Glu Asn Ile Pro Tyr Gly Val Leu Val Trp Ala Thr Gly Asn Ala
        370                 375                 380
Pro Arg Glu Val Ser Lys Asn Leu Met Thr Lys Leu Glu Glu Gln Asp
385                 390                 395                 400
Ser Arg Arg Gly Leu Leu Ile Asp Asn Lys Leu Gln Leu Leu Gly Ala
                405                 410                 415
Lys Gly Ser Ile Phe Ala Ile Gly Asp Cys Thr Phe His Pro Gly Leu
            420                 425                 430
Phe Pro Thr Ala Gln Val Ala His Gln Glu Gly Glu Tyr Leu Ala Gln
        435                 440                 445
Tyr Phe Lys Lys Ala Tyr Lys Ile Asp Gln Leu Asn Trp Lys Met Thr
        450                 455                 460
His Ala Lys Asp Asp Ser Glu Val Ala Arg Leu Lys Asn Gln Ile Val
465                 470                 475                 480
Lys Thr Gln Ser Gln Ile Glu Asp Phe Lys Tyr Asn His Lys Gly Ala
                485                 490                 495
Leu Ala Tyr Ile Gly Ser Asp Lys Ala Ile Ala Asp Leu Ala Val Gly
            500                 505                 510
Glu Ala Lys Tyr Arg Leu Ala Gly Ser Phe Thr Phe Leu Phe Trp Lys
        515                 520                 525
Ser Ala Tyr Leu Ala Met Cys Leu Ser Phe Arg Asn Arg Val Leu Val
        530                 535                 540
Ala Met Asp Trp Ala Lys Val Tyr Phe Leu Gly Arg Asp Ser Ser Ile
545                 550                 555                 560

<210> SEQ ID NO 23
<211> LENGTH: 545
<212> TYPE: PRT
<213> ORGANISM: Saccharomyces cerevisiae

<400> SEQUENCE: 23

-continued

```
Met Leu Pro Arg Leu Gly Phe Ala Arg Thr Ala Arg Ser Ile His Arg
 1               5                  10                  15

Phe Lys Met Thr Gln Ile Ser Lys Pro Phe Phe His Ser Thr Glu Val
            20                  25                  30

Gly Lys Pro Gly Pro Gln Gln Lys Leu Ser Lys Ser Tyr Thr Ala Val
            35                  40                  45

Phe Lys Lys Trp Phe Val Arg Gly Leu Lys Leu Thr Phe Tyr Thr Thr
 50                  55                  60

Leu Ala Gly Thr Leu Tyr Val Ser Tyr Glu Leu Tyr Lys Glu Ser Asn
 65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

Leu Lys Lys Leu Asp Thr Ser Leu Tyr Asn Val Thr Val Val Ser Pro
            115                 120                 125

Arg Ser Phe Phe Leu Phe Thr Pro Leu Leu Pro Ser Thr Pro Val Gly
            130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
                165                 170                 175

Asp Pro Lys Ala Lys Lys Val Met Val Gln Ser Val Ser Glu Asp Glu
            180                 185                 190

Tyr Phe Val Ser Ser Leu Ser Tyr Asp Tyr Leu Val Val Ser Val Gly
            195                 200                 205

Ala Lys Thr Thr Thr Phe Asn Ile Pro Gly Val Tyr Gly Asn Ala Asn
            210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
                245                 250                 255

Lys Arg Leu Leu Thr Phe Val Val Val Gly Gly Gly Pro Thr Gly Val
            260                 265                 270

Glu Phe Ala Ala Glu Leu Gln Asp Tyr Ile Asn Gln Asp Leu Arg Lys
            275                 280                 285

Trp Met Pro Asp Leu Ser Lys Glu Met Lys Val Ile Leu Ile Glu Ala
            290                 295                 300

Leu Pro Asn Ile Leu Asn Met Phe Asp Lys Thr Leu Ile Lys Tyr Ala
305                 310                 315                 320

Glu Asp Leu Phe Ala Arg Asp Glu Ile Asp Leu Gln Val Asn Thr Ala
                325                 330                 335

Val Lys Val Val Glu Pro Thr Tyr Ile Arg Thr Leu Gln Asn Gly Gln
            340                 345                 350

Thr Asn Thr Asp Ile Glu Tyr Gly Met Leu Val Trp Ala Thr Gly Asn
            355                 360                 365

Glu Pro Ile Asp Phe Ser Lys Thr Leu Met Ser Arg Ile Pro Glu Gln
            370                 375                 380

Thr Asn Arg Arg Gly Leu Leu Ile Asn Asp Lys Leu Glu Leu Leu Gly
385                 390                 395                 400

Ser Glu Asn Ser Ile Tyr Ala Ile Gly Asp Cys Thr Ala His Thr Gly
                405                 410                 415

Phe Phe Pro Thr Ala Gln Val Ala His Gln Glu Gly Glu Tyr Leu Ala
```

-continued

```
                420                 425                 430
Lys Ile Leu Asp Lys Lys Leu Gln Ile Glu Gln Leu Glu Trp Asp Met
            435                 440                 445
Leu Asn Ser Thr Asp Glu Thr Glu Val Ser Arg Leu Gln Lys Glu Val
        450                 455                 460
Asn Leu Arg Lys Ser Lys Leu Asp Lys Phe Asn Tyr Lys His Met Gly
465                 470                 475                 480
Ala Leu Ala Tyr Ile Gly Ser Glu Thr Ala Ile Ala Asp Leu His Met
                485                 490                 495
Gly Asp Ser Ser Tyr Gln Leu Lys Gly Met Phe Ala Phe Leu Phe Trp
            500                 505                 510
Lys Ser Ala Tyr Leu Ala Met Cys Leu Ser Ile Arg Asn Arg Ile Leu
        515                 520                 525
Ile Ala Met Asp Trp Thr Lys Val Tyr Phe Leu Gly Arg Asp Ser Ser
    530                 535                 540
Val
545

<210> SEQ ID NO 24
<211> LENGTH: 130
<212> TYPE: PRT
<213> ORGANISM: Saccharomyces cerevisiae

<400> SEQUENCE: 24

Met Ser Gln Pro Val Gln Arg Ala Ala Ala Arg Ser Phe Leu Gln Lys
  1               5                  10                  15
Tyr Ile Asn Lys Glu Thr Leu Lys Tyr Ile Phe Thr Thr His Phe Trp
             20                  25                  30
Gly Pro Val Ser Asn Phe Gly Ile Pro Ile Ala Ala Ile Tyr Asp Leu
         35                  40                  45
Lys Lys Asp Pro Thr Leu Ile Ser Gly Pro Met Thr Phe Ala Leu Val
     50                  55                  60
Thr Tyr Ser Gly Val Phe Met Lys Tyr Ala Leu Ser Val Ser Pro Lys
 65                  70                  75                  80
Asn Tyr Leu Leu Phe Gly Cys His Leu Ile Asn Glu Thr Ala Gln Leu
                 85                  90                  95
Ala Gln Gly Tyr Arg Phe Leu Lys Tyr Thr Tyr Phe Thr Thr Asp Glu
            100                 105                 110
Glu Lys Lys Ala Leu Asp Lys Glu Trp Lys Glu Lys Thr Gly
        115                 120                 125
Lys Gln
    130

<210> SEQ ID NO 25
<211> LENGTH: 1683
<212> TYPE: DNA
<213> ORGANISM: Saccharomyces cerevisiae

<400> SEQUENCE: 25
atgattagac aatcattaat gaaaacagtg tgggctaact cctccaggtt tagcctacag      60
agcaagtcgg ggcttgtgaa atatgccaaa aatagatcgt tccatgcagc aagaaatttg     120
ctagaggaca agaaagtcat tttgcaaaaa gtggcgccca ctactggcgt tgttgcgaag     180
cagtcctttt tcaagagaac tgggaaattt actttgaagg ctttattgta ttctgccctc     240
gcgggtacgg cttacgtttc atactcactt taccgagaag ctaacccttc tacccaagtt     300
```

```
cctcaatcgg acacttttcc aaacggttca agaggaaga ctttggtaat tctgggctcc      360
ggttggggtt ctgtgtcgct tttgaaaaat ttggacacca cgttgtataa tgttgttgtt     420
gtttctccaa gaaattattt tcttttact ccgctattgc catctacccc agttggtacc      480
atcgaattga atctattgt tgaacctgtc aggactattg ctagaagatc gcacggtgaa      540
gtccattact atgaagctga agcgtacgac gttgatcctg aaaacaaaac aattaaggtc     600
aaatcttccg ctaagaataa cgactacgac ttggacttga atacgacta tctggttgtc      660
ggtgtgggtg ctcaaccaaa cacttttggt actccgggag tttatgaata ttcttctttc     720
ttgaaggaaa tatccgacgc tcaagagatc agattaaaaa ttatgtccag tattgagaaa     780
gctgcctccc tatctccaaa agatcctgag agagcaagat tgttgagctt tgttgtcgtt    840
ggtggtggtc ccaccggtgt cgaatttgcc gctgaattga gagattatgt tgaccaggac    900
ttgagaaaat ggatgcccga attgagtaaa gaaattaaag tcactttggt ggaggctttg    960
ccaaacattt tgaacatgtt tgacaagtat ctcgttgact atgctcaaga tttattcaaa   1020
gaggaaaaaa tcgatttaag attgaaaaca atggttaaga aagttgacgc taccactata   1080
actgccaaaa ctggcgatgg tgacattgaa aatataccgt atggtgtatt agtttgggct   1140
acaggtaatg cgccaagaga agtgtctaag aacctaatga ctaaattaga ggaacaggac   1200
tcaagacgtg gtttgttgat agataacaaa cttcaacttt tgggtgctaa gggatctatt   1260
tttgctatcg gcgattgtac cttccaccct ggcttgttcc ctaccgctca agttgcccac   1320
caagaaggtg aatacttggc tcagtatttc aagaaagctt ataaaatcga tcaattgaac   1380
tggaaaatga cccatgctaa agacgattca gaagtcgcta gattaaagaa ccaaatagtc   1440
aaaacgcaat cgcaaattga agacttcaag tacaaccata agggtgctct ggcttatatt   1500
ggttcagata aagccattgc tgatcttgcc gttggtgaag ccaaatatag gttagccggc   1560
tcattcacct tcctattctg gaaatctgct tatttggcaa tgtgtctatc ctttagaaac   1620
agagttcttg tcgctatgga ttgggctaaa gtttatttct gggtagaga ttcatctatc    1680
tag                                                                  1683

<210> SEQ ID NO 26
<211> LENGTH: 1638
<212> TYPE: DNA
<213> ORGANISM: Saccharomyces cerevisiae

<400> SEQUENCE: 26
atgctgccca gacttggttt tgcgaggact gctaggtcca tacaccgttt caagatgacc       60
cagatctcta aacctttttt ccattccact gaagttggta agcccggacc acagcagaag      120
ctatcgaaat cttacactgc ggtattcaag aaatggtttg tcagaggttt aaagttaacc      180
ttttacacga cgttggccgg cacattgtat gtgtcatacg agctgtacaa agaatcgaac      240
ccacccaaac aggttcccca atcgaccgct tttgctaatg gtttgaaaaa gaaggagctg      300
gttatttggg gtacaggctg gggcgccata tctcttttga agaaattaga cacgtctttg      360
tataacgtga ccgtggtgtc gccaagaagc ttcttttttgt tcacaccgtt attccctca     420
acgcctgtgg gtacgataga gatgaagtct attgtcgaac cggttagatc gatcgctaga      480
agaacgcctg agaagttcag ctacattgag gcggaagcgt tggacgttga tccaaaggcc     540
aaaaaagtaa tggtgcaatc ggtgtcagag gacgaatatt tcgtttcgag cttaagttac     600
gattatcttt ttgttagtgt aggcgctaaa accactactt ttaacattcc cggggtctat      660
ggcaatgcta acttcttgaa agagattgaa gatgctcaaa atattcgtat gaagttaatg     720
```

-continued

```
aaaaccatag aacaggcaag ttcatttcct gtgaacgatc cggaaaggaa gcgattatta    780
acgttcgtgg ttgttggagg gggccctacg ggggttgaat ttgccgccga actgcaagat    840
tacatcaatc aagatttgag gaagtggatg cccgacttaa gtaaagaaat gaaggttatc    900
ttaattgaag ccctgcctaa tatcctaaac atgttcgata agacgttgat caagtatgcc    960
gaggaccttt tgccagaga tgaaattgac ttgcaagtga atactgccgt gaaagtcgta   1020
gagccaacct atatacgcac tctgcaaaac ggccaaacaa acacggatat cgaatacggg   1080
atgctggttt gggccacggg aaatgaacca atcgattttt caaagacact gatgagtaga   1140
ataccggagc aaactaatag gcgtggtctg ttaattaatg acaagttgga gcttctcggt   1200
tctgagaatt cgatttatgc aattggtgat tgtaccgcac acacgggttt cttccccacg   1260
gcacaagttg cacatcagga aggcgaatac ttggccaaga tcttggataa aaaattacag   1320
atagaacaat tggaatggga catgctcaac agtaccgatg aaactgaggt atcacgtcta   1380
caaaaagagg ttaatttgag gaaatctaag ttggataagt tcaactacaa gcatatgggt   1440
gcccttgcgt acatcggctc tgaaaccgca attgcagatt tgcatatggg cgactcatca   1500
taccagttga aaggtatgtt tgccttcttg ttttggaaat ccgcttattt ggccatgtgt   1560
ctctctatca ggaataggat tttaattgcc atggactgga ccaaagttta ctttcttgga   1620
agggattcct ccgtgtag                                                 1638

<210> SEQ ID NO 27
<211> LENGTH: 393
<212> TYPE: DNA
<213> ORGANISM: Saccharomyces cerevisiae

<400> SEQUENCE: 27
atgtctcaac cggttcaacg cgctgcagca cgctcattcc ttcaaaaata catcaataaa    60
gaaactttga atatatttt cacaacacac ttctggggtc ccgtatcaaa tttcggtatc    120
ccaattgctg ctatatatga tctgaaaaaa gaccctacac taatctctgg cccaatgact    180
tttgctttag ttacctattc aggtgttttc atgaagtatg ctctttcagt atcacccaaa    240
aactacttac tgtttggatg ccaccttatt aatgaaactc gcaattagc tcaaggctat    300 aggtttctca atacacgta tttcacaaca gatgaggaga gaaagctct agataaggaa    360 tggaaagaga aagaaaaaac tggtaaacag taa                                393

<210> SEQ ID NO 28
<211> LENGTH: 1178
<212> TYPE: PRT
<213> ORGANISM: Saccharomyces cerevisiae

<400> SEQUENCE: 28
```

Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
        35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp

```
                 85                  90                  95
Phe Ile His Pro Gly Tyr Gly Phe Leu Ser Glu Asn Ser Glu Phe Ala
                100                 105                 110

Asp Lys Val Val Lys Ala Gly Ile Thr Trp Ile Gly Pro Pro Ala Glu
            115                 120                 125

Val Ile Asp Ser Val Gly Asp Lys Val Ser Ala Arg Asn Leu Ala Ala
        130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Arg Gly Met Arg Val Val Arg
                180                 185                 190

Glu Gly Asp Asp Val Ala Asp Ala Phe Gln Arg Ala Thr Ser Glu Ala
            195                 200                 205

Arg Thr Ala Phe Gly Asn Gly Thr Cys Phe Val Glu Arg Phe Leu Asp
        210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                325                 330                 335

Ala Gly Ala Ser Leu Pro Gln Leu Gly Leu Phe Gln Asp Lys Ile Thr
            340                 345                 350

Thr Arg Gly Phe Ala Ile Gln Cys Arg Ile Thr Thr Glu Asp Pro Ala
        355                 360                 365

Lys Asn Phe Gln Pro Asp Thr Gly Arg Ile Glu Val Tyr Arg Ser Ala
370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                405                 410                 415

Gly Ser Thr Tyr Glu Ile Val Arg Arg Lys Met Ile Arg Ala Leu Ile
            420                 425                 430

Glu Phe Arg Ile Arg Gly Val Lys Thr Asn Ile Pro Phe Leu Leu Thr
        435                 440                 445

Leu Leu Thr Asn Pro Val Phe Ile Glu Gly Thr Tyr Trp Thr Thr Phe
450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
            500                 505                 510
```

```
Val Pro His Leu His Asp Ala Gln Gly Asn Val Ile Asn Val Thr Lys
        515                 520                 525

Ser Ala Pro Pro Ser Gly Trp Arg Gln Val Leu Leu Glu Lys Gly Pro
        530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
                580                 585                 590

Ala Gly Arg Phe Ala Leu Glu Cys Trp Gly Ala Thr Phe Asp Val
        595                 600                 605

Ala Met Arg Phe Leu His Glu Asp Pro Trp Glu Arg Leu Arg Lys Leu
        610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
        660                 665                 670

Ala Leu Asn Asp Leu Glu Gln Leu Lys Val Gly Val Asp Ala Val Lys
        675                 680                 685

Lys Ala Gly Gly Val Val Glu Ala Thr Val Cys Phe Ser Gly Asp Met
690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Ala Lys Leu Leu Ile Gly Ser Leu
                740                 745                 750

Arg Ala Lys Tyr Pro Asp Leu Pro Ile His Val His Thr His Asp Ser
        755                 760                 765

Ala Gly Thr Ala Val Ala Ser Met Thr Ala Cys Ala Leu Ala Gly Ala
        770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
                820                 825                 830

Met Arg Leu Leu Tyr Ser Cys Phe Glu Ala Asp Leu Lys Gly Pro Asp
        835                 840                 845

Pro Glu Val Tyr Gln His Glu Ile Pro Gly Gly Gln Leu Thr Asn Leu
        850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
                900                 905                 910

Ser Asn Lys Leu Thr Ser Asp Asp Val Arg Arg Leu Ala Asn Ser Leu
        915                 920                 925
```

Asp Phe Pro Asp Ser Val Met Asp Phe Phe Glu Gly Leu Ile Gly Gln
    930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
            980                 985                 990

Asp Glu Cys Asp Val Ala Ser Tyr Asn Met Tyr Pro Arg Val Tyr Glu
        995                 1000                1005

Asp Phe Gln Lys Met Arg Glu Thr Tyr Gly Asp Leu Ser Val Leu Pro
    1010                1015                1020

Thr Arg Ser Phe Leu Ser Pro Leu Glu Thr Asp Glu Ile Glu Val
1025                1030                1035                1040

Val Ile Glu Gln Gly Lys Thr Leu Ile Ile Lys Leu Gln Ala Val Gly
                1045                1050                1055

Asp Leu Asn Lys Lys Thr Gly Glu Arg Glu Val Tyr Phe Asp Leu Asn
            1060                1065                1070

Gly Glu Met Arg Lys Ile Arg Val Ala Asp Arg Ser Gln Lys Val Glu
        1075                1080                1085

Thr Val Thr Lys Ser Lys Ala Asp Met His Asp Pro Leu His Ile Gly
    1090                1095                1100

Ala Pro Met Ala Gly Val Ile Val Glu Val Lys Val His Lys Gly Ser
1105                1110                1115                1120

Leu Ile Lys Lys Gly Gln Pro Val Ala Val Leu Ser Ala Met Lys Met
                1125                1130                1135

Glu Met Ile Ile Ser Ser Pro Ser Asp Gly Gln Val Lys Glu Val Phe
            1140                1145                1150

Val Ser Asp Gly Glu Asn Val Asp Ser Ser Asp Leu Leu Val Leu Leu
        1155                1160                1165

Glu Asp Gln Val Pro Val Glu Thr Lys Ala
    1170                1175

<210> SEQ ID NO 29
<211> LENGTH: 1180
<212> TYPE: PRT
<213> ORGANISM: Saccharomyces cerevisiae

<400> SEQUENCE: 29

Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
            100                 105                 110

Ala Asp Lys Val Val Lys Ala Gly Ile Thr Trp Ile Gly Pro Pro Ala
        115                 120                 125

-continued

```
Glu Val Ile Asp Ser Val Gly Asp Lys Val Ser Ala Arg His Leu Ala
    130                 135                 140
Ala Arg Ala Asn Val Pro Thr Val Pro Gly Thr Pro Gly Pro Ile Glu
145                 150                 155                 160
Thr Val Gln Glu Ala Leu Asp Phe Val Asn Glu Tyr Gly Tyr Pro Val
                165                 170                 175
Ile Ile Lys Ala Ala Phe Gly Gly Gly Arg Gly Met Arg Val Val
            180                 185                 190
Arg Glu Gly Asp Asp Val Ala Asp Ala Phe Gln Arg Ala Thr Ser Glu
        195                 200                 205
Ala Arg Thr Ala Phe Gly Asn Gly Thr Cys Phe Val Glu Arg Phe Leu
    210                 215                 220
Asp Lys Pro Lys His Ile Glu Val Gln Leu Leu Ala Asp Asn His Gly
225                 230                 235                 240
Asn Val Val His Leu Phe Glu Arg Asp Cys Ser Val Gln Arg Arg His
                245                 250                 255
Gln Lys Val Val Glu Val Ala Pro Ala Lys Thr Leu Pro Arg Glu Val
            260                 265                 270
Arg Asp Ala Ile Leu Thr Asp Ala Val Lys Leu Ala Lys Val Cys Gly
        275                 280                 285
Tyr Arg Asn Ala Gly Thr Ala Glu Phe Leu Val Asp Asn Gln Asn Arg
    290                 295                 300
His Tyr Phe Ile Glu Ile Asn Pro Arg Ile Gln Val Glu His Thr Ile
305                 310                 315                 320
Thr Glu Glu Ile Thr Gly Ile Asp Ile Val Ser Ala Gln Ile Gln Ile
                325                 330                 335
Ala Ala Gly Ala Thr Leu Thr Gln Leu Gly Leu Leu Gln Asp Lys Ile
            340                 345                 350
Thr Thr Arg Gly Phe Ser Ile Gln Cys Arg Ile Thr Thr Glu Asp Pro
        355                 360                 365
Ser Lys Asn Phe Gln Pro Asp Thr Gly Arg Leu Glu Val Tyr Arg Ser
    370                 375                 380
Ala Gly Gly Asn Gly Val Arg Leu Asp Gly Gly Asn Ala Tyr Ala Gly
385                 390                 395                 400
Ala Thr Ile Ser Pro His Tyr Asp Ser Met Leu Val Lys Cys Ser Cys
                405                 410                 415
Ser Gly Ser Thr Tyr Glu Ile Val Arg Arg Lys Met Ile Arg Ala Leu
            420                 425                 430
Ile Glu Phe Arg Ile Arg Gly Val Lys Thr Asn Ile Pro Phe Leu Leu
        435                 440                 445
Thr Leu Leu Thr Asn Pro Val Phe Ile Glu Gly Thr Tyr Trp Thr Thr
    450                 455                 460
Phe Ile Asp Asp Thr Pro Gln Leu Phe Gln Met Val Ser Ser Gln Asn
465                 470                 475                 480
Arg Ala Gln Lys Leu Leu His Tyr Leu Ala Asp Leu Ala Val Asn Gly
                485                 490                 495
Ser Ser Ile Lys Gly Gln Ile Gly Leu Pro Lys Leu Lys Ser Asn Pro
            500                 505                 510
Ser Val Pro His Leu His Asp Ala Gln Gly Asn Val Ile Asn Val Thr
        515                 520                 525
Lys Ser Ala Pro Pro Ser Gly Trp Arg Gln Val Leu Leu Glu Lys Gly
    530                 535                 540
```

-continued

```
Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
            565                 570                 575

Val Arg Thr His Asp Leu Ala Thr Ile Ala Pro Thr Thr Ala His Ala
        580                 585                 590

Leu Ala Gly Ala Phe Ala Leu Glu Cys Trp Gly Gly Ala Thr Phe Asp
    595                 600                 605

Val Ala Met Arg Phe Leu His Glu Asp Pro Trp Glu Arg Leu Arg Lys
610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
            645                 650                 655

Phe Val Lys Gln Ala Lys Asp Asn Gly Val Asp Ile Phe Arg Val Phe
        660                 665                 670

Asp Ala Leu Asn Asp Leu Glu Gln Leu Lys Val Gly Val Asn Ala Val
    675                 680                 685

Lys Lys Ala Gly Gly Val Val Glu Ala Thr Val Cys Tyr Ser Gly Asp
690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
            725                 730                 735

Met Ala Gly Thr Met Lys Pro Ala Ala Ala Lys Leu Leu Ile Gly Ser
        740                 745                 750

Leu Arg Thr Arg Tyr Pro Asp Leu Pro Ile His Val His Ser His Asp
    755                 760                 765

Ser Ala Gly Thr Ala Val Ala Ser Met Thr Ala Cys Ala Leu Ala Gly
770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
            805                 810                 815

Thr Gly Ile Asn Val Glu His Val Arg Glu Leu Asp Ala Tyr Trp Ala
        820                 825                 830

Glu Met Arg Leu Leu Tyr Ser Cys Phe Glu Ala Asp Leu Lys Gly Pro
    835                 840                 845

Asp Pro Glu Val Tyr Gln His Glu Ile Pro Gly Gly Gln Leu Thr Asn
850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
            885                 890                 895

Lys Val Thr Pro Thr Ser Lys Val Val Gly Asp Leu Ala Gln Phe Met
        900                 905                 910

Val Ser Asn Lys Leu Thr Ser Asp Asp Ile Arg Arg Leu Ala Asn Ser
    915                 920                 925

Leu Asp Phe Pro Asp Ser Val Met Asp Phe Phe Glu Gly Leu Ile Gly
930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
```

```
              965                970                975
Phe Asp Leu Glu Lys Ile Arg Glu Asp Leu Gln Asn Arg Phe Gly Asp
                980                985                990
Ile Asp Glu Cys Asp Val Ala Ser Tyr Asn Met Tyr Pro Arg Val Tyr
                995               1000               1005
Glu Asp Phe Gln Lys Ile Arg Glu Thr Tyr Gly Asp Leu Ser Val Leu
   1010               1015               1020
Pro Thr Lys Asn Phe Leu Ala Pro Ala Glu Pro Asp Glu Glu Ile Glu
1025               1030               1035               1040
Val Thr Ile Glu Gln Gly Lys Thr Leu Ile Ile Lys Leu Gln Ala Val
              1045               1050               1055
Gly Asp Leu Asn Lys Lys Thr Gly Gln Arg Glu Val Tyr Phe Glu Leu
         1060               1065               1070
Asn Gly Glu Leu Arg Lys Ile Arg Val Ala Asp Lys Ser Gln Asn Ile
         1075               1080               1085
Gln Ser Val Ala Lys Pro Lys Ala Asp Val His Asp Thr His Gln Ile
         1090               1095               1100
Gly Ala Pro Met Ala Gly Val Ile Ile Glu Val Lys Val His Lys Gly
1105               1110               1115               1120
Ser Leu Val Lys Lys Gly Glu Ser Ile Ala Val Leu Ser Ala Met Lys
              1125               1130               1135
Met Glu Met Val Val Ser Ser Pro Ala Asp Gly Gln Val Lys Asp Val
              1140               1145               1150
Phe Ile Lys Asp Gly Glu Ser Val Asp Ala Ser Asp Leu Leu Val Val
         1155               1160               1165
Leu Glu Glu Glu Thr Leu Pro Pro Ser Gln Lys Lys
    1170               1175               1180

<210> SEQ ID NO 30
<211> LENGTH: 3537
<212> TYPE: DNA
<213> ORGANISM: Saccharomyces cerevisiae

<400> SEQUENCE: 30
atgtcgcaaa gaaaattcgc cggcttgaga gataacttca atctcttggg tgaaaagaac      60
aaaatattgg tggctaatag aggagaaatt ccaatcagaa ttttcgtac cgctcatgaa      120 ctgtctatgc agacggtagc tatatattct catgaagatc gtctttcaac gcacaaacaa      180
aaggctgacg aagcatacgt cataggtgaa gtaggccaat ataccccgt cggcgcttat      240 ttggccattg acgaaatcat ttccattgcc caaaaacacc aggtagattt catccatcca      300
ggttatgggt tcttgtctga aaattcggaa tttgccgaca agtagtgaa ggccggtatc      360 acttggattg ccctccagc tgaagttatt gactccgtgg gtgataaggt ctcagctaga      420
aacctggcag caaaagctaa tgtgcccacc gttcctggta caccaggtcc tatagaaact      480
gtagaggaag cacttgactt cgtcaatgaa tacggctacc cggtgatcat taaggccgcc      540
tttggtggtg gtggtagagg tatgagagtc gttagagaag gtgacgacgt ggcagatgcc      600
tttcaacgtg ctacctccga agcccgtact gccttcggta atggtacctg ctttgtggaa      660
agattcttgg acaagccaaa gcatattgaa gttcaattgt ggccgataa ccacggaaac      720 gtggttcatc ttttcgaaag agactgttcc gtgcagagaa gacaccaaaa ggttgtcgaa      780
gtggccccag caaagacttt accccgtgaa gtccgtgacg ccattttgac agatgcagtt      840
aaattggcca agagtgtgg ctacagaaat gcgggtactg ctgaattctt ggttgataac      900
```

```
caaaatagac actatttcat tgaaattaat ccaagaatcc aagtggaaca taccatcaca    960
gaagaaatta ccggtataga tattgtggcg gctcagatcc aaattgcggc aggtgcctct   1020
ctaccccagc tgggcctatt ccaggacaaa attacgactc gtggctttgc cattcagtgc   1080
cgtattacca cggaagaccc tgctaagaac ttccaaccag ataccggtag aatagaagtg   1140
taccgttctg caggtggtaa tggtgttaga ctggatggtg gtaacgccta tgcaggaaca   1200
ataatctcac ctcattacga ctcaatgctg tcaaatgct  catgctccgg ttccacctac   1260
gaaatcgttc gtagaaaaat gattcgtgca ttaatcgagt tcagaattag aggtgtcaag   1320
accaacattc ccttcctatt gactcttttg accaatccag tatttattga gggtacatac   1380
tggacgactt ttattgacga cacccccacaa ctgttccaaa tggtttcatc acaaaacaga  1440
gcccaaaaac ttttacatta cctcgccgac gtggcagtca atggttcatc tatcaagggt   1500
caaattggct tgccaaaatt aaaatcaaat ccaagtgtcc cccatttgca cgatgctcag   1560
ggcaatgtca tcaacgttac aaagtctgca ccaccatccg gatggaggca agtgctacta   1620
gaaaaggggc cagctgaatt tgccagacaa gttagacagt tcaatggtac tttattgatg   1680
gacaccacct ggagagacgc tcatcaatct ctacttgcaa caagagtcag aacccacgat   1740
ttggctacaa tcgctccaac aaccgcacat gcccttgcag gtcgtttcgc cttagaatgt   1800
tggggtggtg ccacattcga tgttgcaatg agattttttgc atgaggatcc atgggaacgt   1860
ttgagaaaat taagatctct ggtgcctaat attccattcc aaatgttatt gcgtggtgcc   1920
aatggtgtgg cttattcttc attgcctgac aatgctattg accatttcgt caagcaagcc   1980
aaggataatg gtgttgatat atttagagtc tttgatgcct taaatgactt ggaacaattg   2040
aaggtcggtg tagatgctgt gaagaaggca ggtggtgttg tagaagccac tgtttgtttc   2100
tctggggata tgcttcagcc aggcaagaaa tacaatttgg attactactt ggaaattgct   2160
gaaaaaattg tccaaatggg cactcatatc ctgggtatca agatatggc  aggtaccatg   2220
aagccagcag ctgccaaaact actgattgga tctttgaggg ctaagtaccc tgatctccca   2280
atacatgttc acactcacga ttctgcaggt actgctgttg catcaatgac tgcgtgtgct   2340
ctggcgggcg ccgatgtcgt tgatgttgcc atcaactcaa tgtctggttt aacttcacaa   2400
ccatcaatca atgctctgtt ggcttcatta gaaggtaata ttgacactgg tattaacgtt   2460
gagcatgtcc gtgaactaga tgcatattgg gcagagatga gattgttata ctcttgtttc   2520
gaggctgact tgaagggccc agatccagaa gtttatcaac atgaaatccc aggtggtcaa   2580
ttgacaaact tgttgtttca gcccaacaa  ttgggtcttg gagaacaatg ggccgaaaca   2640
aaaagagctt acagagaagc caattatttta ttgggtgata ttgtcaaagt taccccaact   2700
tcgaaggtcg ttggtgatct ggcacaattt atggtctcca ataaattaac ttccgatgat   2760
gtgagacgcc tggctaattc tttggatttc cctgactctg ttatggattt cttcgaaggc   2820
ttaatcggcc aaccatatgg tgggttccca gaaccattta gatcagacgt tttaaggaac   2880
aagagaagaa agttgacttg tcgtccaggc ctggaactag agccatttga tctcgaaaaa   2940
attagagaag acttgcagaa tagatttggt gatgttgatg agtgcgacgt tgcttcttat   3000
aacatgtacc aagagtttta tgaagacttc caaaagatga gagaaacgta tggtgattta   3060
tctgtattgc caacaagaag cttttttgtct ccactagaga ctgacgaaga aattgaagtt   3120
gtaatcgaac aaggtaaaac gctaattatc aagctacagg ctgtgggtga tttgaacaaa   3180
aagaccggtg aaagagaagt ttactttgat ttgaatggtg aaatgagaaa aattcgtgtt   3240
gctgacagat cacaaaaagt ggaaactgtt actaaatcca aagcagacat gcatgatcca   3300
```

```
ttacacattg gtgcaccaat ggcaggtgtc attgttgaag ttaaagttca taaaggatca    3360
ctaataaaga agggccaacc tgtagccgta ttaagcgcca tgaaaatgga aatgattata    3420
tcttctccat ccgatggaca agttaaagaa gtgtttgtct ctgatggtga aaatgtggac    3480
tcttctgatt tattagttct attagaagac caagttcctg ttgaaactaa ggcatga      3537

<210> SEQ ID NO 31
<211> LENGTH: 3543
<212> TYPE: DNA
<213> ORGANISM: Saccharomyces cerevisiae

<400> SEQUENCE: 31
atgagcagta gcaagaaatt ggccggtctt agggacaatt tcagtttgct cggcgaaaag      60
aataagatct tggtcgccaa tagaggtgaa attccgatta gaattttttag atctgctcat    120 gagctgtcta tgagaaccat cgccatatac tcccatgagg accgtctttc aatgcacagg     180
ttgaaggcgg acgaagcgta tgttatcggg gaggagggcc agtatacacc tgtgggtgct     240
tacttggcaa tggacgagat catcgaaatt gcaagaaagc ataaggtgga tttcatccat     300
ccaggttatg ggttcttgtc tgaaaattcg gaatttgccg acaaagtagt gaaggccggt     360
atcacttgga tcggccctcc agctgaagtt attgactctg tgggtgacaa agtctctgcc     420
agacacttgg cagcaagagc taacgttcct accgttcccg gtactccagg acctatcgaa     480
actgtgcaag aggcacttga cttcgttaat gaatacggct acccggtgat cattaaggcc     540
gcctttggtg gtggtggtag aggtatgaga gtcgttagag aaggtgacga cgtggcagat     600
gcctttcaac gtgctacctc cgaagcccgt actgccttcg gtaatggtac ctgctttgtg     660
gaaagattct tggacaagcc aaagcatatt gaagttcaat tgttggctga taaccacgga     720
aacgtggttc atcttttcga aagagactgt tctgtgcaaa gaagacacca aaaagttgtc     780
gaagtcgctc cagcaaagac tttgccccgt gaagttcgtg acgctatttt gacagatgct     840
gttaaattag ctaaggtatg tggttacaga aacgcaggta ccgccgaatt cttggttgac     900
aaccaaaaca gacactattt cattgaaatt aatccaagaa ttcaagtgga gcataccatc     960
actgaagaaa tcaccggtat tgacattgtt tctgcccaaa tccagattgc cgcaggtgcc    1020
actttgactc aactaggtct attacaggat aaaatcacca cccgtgggtt ttccatccaa    1080
tgtcgtatta ccactgaaga tcccctctaag aattccaac cggataccgg tcgcctggag    1140
gtctatcgtt ctgccggtgg taatggtgtg agattggacg gtggtaacgc ttatgcaggt    1200
gctactatct cgcctcacta cgactcaatg ctggtcaaat gttcatgctc tggttctact    1260
tatgaaatcg tccgtaggaa gatgattcgt gccctgatcg aattcagaat cagaggtgtt    1320
aagaccaaca ttcccttcct attgactctt ttgaccaatc cagtttttat tgagggtaca    1380
tactggacga cttttattga cgacaccccca caactgttcc aaatggtatc gtcacaaaac    1440
agagcgcaaa aactgttaca ctatttggca gacttggcag ttaacggttc ttctattaag    1500
ggtcaaattg gcttgccaaa actaaaatca aatccaagtg tcccccattt gcacgatgct    1560
cagggcaatg tcatcaacgt tacaaagtct gcaccaccat ccggatggag acaagtgcta    1620
ctggaaaagg gaccatctga atttgccaag caagtcgacg agttcaatgg tactctactg    1680
atggacacca cctggagaga cgctcatcaa tctctacttg caacaagagt cagaacccac    1740
gatttggcta caatcgctcc aacaaccgca catgcccttg caggtgcttt cgctttagaa    1800
tgttggggtg gtgctacatt cgacgttgca atgagattct gcatgagga tccatgggaa    1860
```

```
cgtctgagaa aattaagatc tctggtgcct aatattccat tccaaatgtt attacgtggt    1920
gccaacggtg tggcttactc ttcattacct gacaatgcta ttgaccattt tgtcaagcaa    1980
gccaaggata atggtgttga tatatttaga gttttttgatg ccttgaatga tttagaacaa   2040
ttaaaagttg gtgtgaatgc tgtcaagaag gccggtggtg ttgtcgaagc tactgtttgt    2100
tactctggtg acatgcttca gccaggtaag aaatacaact tagactacta cctagaagtt    2160
gttgaaaaaa tagttcaaat gggtacacat atcttgggta ttaaggatat ggcaggtact    2220
atgaaaccgg ccgctgccaa attattaatt ggctccctaa gaaccagata tccggattta    2280
ccaattcatg ttcacagtca tgactccgca ggtactgctg ttgcgtctat gactgcatgt    2340
gccctagcag gtgctgatgt tgtcgatgta gctatcaatt caatgtcggg cttaacttcc    2400
caaccatcaa ttaatgcact gttggcttca ttagaaggta acattgatac tgggattaac    2460
gttgagcatg ttcgtgaatt agatgcatac tgggccgaaa tgagactgtt gtattcttgt    2520
ttcgaggccg acttgaaggg accagatcca gaagtttacc aacatgaaat cccaggtggt    2580
caattgacta acttgttatt ccaagctcaa caactgggtc ttggtgaaca atgggctgaa    2640
actaaaagag cttacagaga agccaattac ctactgggag atattgttaa agttaccccca   2700 acttctaagg ttgtcggtga tttagctcaa ttcatggttt ctaacaaact gacttccgac    2760
gatattagac gtttagctaa ttcttttggac tttcctgact ctgttatgga cttttttgaa    2820
ggtttaattg gtcaaccata cggtgggttc ccagaaccat taagatctga tgtattgaga    2880
aacaagagaa gaaagttgac gtgccgtcca ggtttagaat tagaaccatt tgatctcgaa    2940
aaaattagag aagacttgca gaacagattc ggtgatattg atgaatgcga tgttgcttct    3000
tacaatatgt atccaagggt ctatgaagat ttccaaaaga tcagagaaac atacggtgat    3060
ttatcagttc taccaaccaa aaatttccta gcaccagcag aacctgatga agaaatcgaa    3120
gtcaccatcg aacaaggtaa gactttgatt atcaaattgc aagctgttgg tgacttaaat    3180
aagaaaactg ggcaaagaga agtgtatttt gaattgaacg tgaattaag aaagatcaga    3240 gttgcagaca agtcacaaaa catacaatct gttgctaaac caaaggctga tgtccacgat    3300
actcaccaaa tcggtgcacc aatggctggt gttatcatag aagttaaagt acataaaggg    3360 tcttttggtga aaaagggcga atcgattgct gttttgagtg ccatgaaaat ggaaatggtt    3420
gtctcttcac cagcagatgg tcaagttaaa gacgttttca ttaaggatgg tgaaagtgtt    3480
gacgcatcag atttgttggt tgtcctagaa gaagaaaccc tacccccatc ccaaaaaaag    3540
taa                                                                   3543
```

<210> SEQ ID NO 32
<211> LENGTH: 382
<212> TYPE: PRT
<213> ORGANISM: Saccharomyces cerevisiae

<400> SEQUENCE: 32

Met Ser Ser Val Thr Gly Phe Tyr Ile Pro Pro Ile Ser Phe Phe Gly
 1               5                  10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
    50                  55                  60

Ile Tyr Asp Lys Thr Gln Pro Asn Pro Asn Ile Ala Asn Val Thr Ala

```
                65                  70                  75                  80
Gly Leu Lys Val Leu Lys Glu Gln Asn Ser Glu Ile Val Val Ser Ile
                    85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
        195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
370                 375                 380

<210> SEQ ID NO 33
<211> LENGTH: 1149
<212> TYPE: DNA
<213> ORGANISM: Saccharomyces cerevisiae

<400> SEQUENCE: 33
atgtcttccg ttactgggtt ttacattcca ccaatctctt tctttggtga aggtgcttta    60
gaagaaaccg ctgattacat caaaaacaag gattacaaaa aggctttgat cgttactgat   120
cctggtattg cagctattgg tctctccggt agagtccaaa gatgttggaa gaacgtgac    180 ttaaacgttg ctatctatga caaaactcaa ccaaacccaa atattgccaa tgtcacagct   240
ggtttgaagg ttttgaagga acaaaactct gaaattgttg tttccattgg tggtggttct   300
gctcacgaca atgctaaggc cattgcttta ttggctacta acggtgggga aatcggagac   360
```

```
tatgaaggtg tcaatcaatc taagaaggct gctttaccac tatttgccat caacactact    420
gctggtactg cttccgaaat gaccagattc actattatct ctaatgaaga aaagaaaatc    480
aagatggcta tcattgacaa caacgtcact ccagctgttg ctgtcaacga tccatctacc    540
atgtttggtt tgccacctgc tttgactgct gctactggtc tagatgcttt gactcactgt    600
atcgaagctt atgtttccac cgcctctaac ccaatcaccg atgcctgtgc tttgaagggt    660
attgatttga tcaatgaaag cttagtcgct gcatacaaag acggtaaaga caagaaggcc    720
agaactgaca tgtgttacgc tgaatacttg gcaggtatgg ctttcaacaa tgcttctcta    780
ggttatgttc atgcccttgc tcatcaactt ggtggtttct accacttgcc tcatggtgtt    840
tgtaacgctg tcttgttgcc tcatgttcaa gaggccaaca tgcaatgtcc aaaggccaag    900
aagagattag gtgaaattgc tttgcatttc ggtgcttctc aagaagatcc agaagaaacc    960
atcaaggctt gcacgttttt aaacagaacc atgaacattc aagaaacttt gaaagaatta   1020
ggtgttaaaa ccgaagattt tgaaattttg gctgaacacg ccatgcatga tgcctgccat   1080
ttgactaacc cagttcaatt caccaaagaa caagtggttg ccattatcaa gaaagcctat   1140
gaatattaa                                                            1149
```

<210> SEQ ID NO 34
<211> LENGTH: 669
<212> TYPE: PRT
<213> ORGANISM: Saccharomyces cerevisiae

<400> SEQUENCE: 34

Met Ser Asn Pro Gln Lys Ala Leu Asn Asp Phe Leu Ser Ser Glu Ser
 1               5                  10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His His Ser Gly Gly
        35                  40                  45

Thr Asn Asn Asn Asn Asn Asn Asn Asn Asn Asn Ser Asn Asn
    50                  55                  60

Asn Asn Asn Gly Asn Asp Gly Gly Asn Asp Asp Asp Tyr Asp Tyr Glu
65                  70                  75                  80

Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
    130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Thr Gly Ala Gln Thr Asn Met Glu
        195                 200                 205

Ser Asn Glu Ser Pro Arg Asn Val Pro Ile Met Val Lys Pro Lys Thr
    210                 215                 220

Leu Tyr Gln Asn Pro Gln Thr Pro Thr Val Leu Pro Ser Thr Tyr His

```
            225                 230                 235                 240
Pro Ile Asn Lys Trp Ser Ser Val Lys Asn Thr Tyr Leu Lys Glu Phe
                245                 250                 255
Leu Ala Glu Phe Met Gly Thr Met Val Met Ile Ile Phe Gly Ser Ala
                260                 265                 270
Val Val Cys Gln Val Asn Val Ala Gly Lys Ile Gln Gln Asp Asn Phe
                275                 280                 285
Asn Val Ala Leu Asp Asn Leu Asn Val Thr Gly Ser Ser Ala Glu Thr
                290                 295                 300
Ile Asp Ala Met Lys Ser Leu Thr Ser Leu Val Ser Ser Val Ala Gly
305                 310                 315                 320
Gly Thr Phe Asp Asp Val Ala Leu Gly Trp Ala Ala Ala Val Val Met
                325                 330                 335
Gly Tyr Phe Cys Ala Gly Gly Ser Ala Ile Ser Gly Ala His Leu Asn
                340                 345                 350
Pro Ser Ile Thr Leu Ala Asn Leu Val Tyr Arg Gly Phe Pro Leu Lys
                355                 360                 365
Lys Val Pro Tyr Tyr Phe Ala Gly Gln Leu Ile Gly Ala Phe Thr Gly
                370                 375                 380
Ala Leu Ile Leu Phe Ile Trp Tyr Lys Arg Val Leu Gln Glu Ala Tyr
385                 390                 395                 400
Ser Asp Trp Trp Met Asn Glu Ser Val Ala Gly Met Phe Cys Val Phe
                405                 410                 415
Pro Lys Pro Tyr Leu Ser Ser Gly Arg Gln Phe Phe Ser Glu Phe Leu
                420                 425                 430
Cys Gly Ala Met Leu Gln Ala Gly Thr Phe Ala Leu Thr Asp Pro Tyr
                435                 440                 445
Thr Cys Leu Ser Ser Asp Val Phe Pro Leu Met Met Phe Ile Leu Ile
                450                 455                 460
Phe Ile Ile Asn Ala Ser Met Ala Tyr Gln Thr Gly Thr Ala Met Asn
465                 470                 475                 480
Leu Ala Arg Asp Leu Gly Pro Arg Leu Ala Leu Tyr Ala Val Gly Phe
                485                 490                 495
Asp His Lys Met Leu Trp Val His His His Phe Phe Trp Val Pro
                500                 505                 510
Met Val Gly Pro Phe Ile Gly Ala Leu Met Gly Gly Leu Val Tyr Asp
                515                 520                 525
Val Cys Ile Tyr Gln Gly His Glu Ser Pro Val Asn Trp Ser Leu Pro
530                 535                 540
Val Tyr Lys Glu Met Ile Met Arg Ala Trp Phe Arg Arg Pro Gly Trp
545                 550                 555                 560
Lys Lys Arg Asn Arg Ala Arg Thr Ser Asp Leu Ser Asp Phe Ser
                565                 570                 575
Tyr Asn Asn Asp Asp Glu Glu Phe Gly Glu Arg Met Ala Leu Gln
                580                 585                 590
Lys Thr Lys Thr Lys Ser Ser Ile Ser Asp Asn Glu Asn Glu Ala Gly
                595                 600                 605
Glu Lys Lys Val Gln Phe Lys Ser Val Gln Arg Gly Lys Arg Thr Phe
                610                 615                 620
Gly Gly Ile Pro Thr Ile Leu Glu Glu Glu Asp Ser Ile Glu Thr Ala
625                 630                 635                 640
Ser Leu Gly Ala Thr Thr Thr Asp Ser Ile Gly Leu Ser Asp Thr Ser
                645                 650                 655
```

Ser Glu Asp Ser His Tyr Gly Asn Ala Lys Lys Val Thr
            660                 665

<210> SEQ ID NO 35
<211> LENGTH: 2010
<212> TYPE: DNA
<213> ORGANISM: Saccharomyces cerevisiae

<400> SEQUENCE: 35

| | | | | | |
|---|---|---|---|---|---|
| atgagtaatc | ctcaaaaagc | tctaaacgac | tttctgtcca | gtgaatctgt | tcatacacat | 60 |
| gatagttcta | ggaaacaatc | taataagcag | tcatccgacg | aaggacgctc | ttcatcacaa | 120 |
| ccttcacatc | atcactctgg | tggtactaac | aacaataata | acaataataa | taataataat | 180 |
| aacagtaaca | caacaacaa | cggcaacgat | gggggaaatg | atgacgacta | tgattatgaa | 240 |
| atgcaagatt | atagaccttc | tccgcaaagt | gcgcggccta | ctcccacgta | tgttccacaa | 300 |
| tattctgtag | aaagtgggac | tgctttcccg | attcaagagg | ttattcctag | cgcatacatt | 360 |
| aacacacaag | atataaaacca | taagataac | ggtccgccga | gtgcaagcag | taatagagca | 420 |
| ttcaggccta | gagggcagac | cacagtgtcg | gccaacgtgc | ttaacattga | agattttac | 480 |
| aaaaatgcag | acgatgcgca | taccatcccg | gagtcacatt | tatcgagaag | gagaagtagg | 540 |
| tcgagggcta | cgagtaatgc | tgggcacagt | gccaatacag | gcgccacgaa | tggcaggact | 600 |
| actggtgccc | aaactaatat | ggaaagcaat | gaatcaccac | gtaacgtccc | cattatggtg | 660 |
| aagccaaaga | cattatacca | gaaccctcaa | acacctacag | tcttgccctc | cacataccat | 720 |
| ccaattaata | aatggtcttc | cgtcaaaaac | acttatttga | aggaattttt | agccgagttt | 780 |
| atgggaacaa | tggttatgat | tattttcggt | agtgctgttg | tttgtcaggt | caatgttgct | 840 |
| gggaaaatac | agcaggacaa | tttcaacgtg | gctttggata | accttaacgt | taccgggtct | 900 |
| tctgcagaaa | cgatagacgc | tatgaagagt | ttaacatcct | tggtttcatc | cgttgcgggc | 960 |
| ggtaccttg | atgatgtggc | attgggctgg | gctgctgccg | tggtgatggg | ctatttctgc | 1020 |
| gctggtggta | gtgccatctc | aggtgctcat | ttgaatccgt | ctattacatt | agccaatttg | 1080 |
| gtgtatagag | ttttcccct | gaagaaagtt | cctattact | ttgctggaca | attgatcggt | 1140 |
| gccttcacag | gcgctttgat | cttgtttatt | tggtacaaaa | gggtgttaca | agaggcatat | 1200 |
| agcgattggt | ggatgaatga | aagtgttgcg | ggaatgtttt | gcgttttcc | aaagccttat | 1260 |
| ctaagttcag | gacggcaatt | tttttccgaa | tttttatgtg | gagctatgtt | acaagcagga | 1320 |
| acatttgcgc | tgaccgatcc | ttatacgtgt | ttgtcctctg | atgttttccc | attgatgatg | 1380 |
| tttatttga | ttttcattat | caatgcttcc | atggcttatc | agacaggtac | agcaatgaat | 1440 |
| ttggctcgtg | atctgggccc | acgtcttgca | ctatatgcag | ttggatttga | tcataaaatg | 1500 |
| ctttgggtgc | atcatcatca | tttcttttgg | gttcccatgg | taggcccatt | tattggtgcg | 1560 |
| ttaatggggg | ggttggttta | cgatgtctgt | atttatcagg | gtcatgaatc | tccagtcaac | 1620 |
| tggtctttac | cagtttataa | ggaaatgatt | atgagagcct | ggtttagaag | gcctggttgg | 1680 |
| aagaagagaa | atagagcaag | aagaacatcg | gacctgagtg | acttctcata | caataacgat | 1740 |
| gatgatgagg | aatttggaga | agaatggct | cttcaaaaga | caaagaccaa | gtcatctatt | 1800 |
| tcagacaacg | aaaatgaagc | aggagaaaag | aaagtgcaat | ttaaatctgt | tcagcgcggc | 1860 |
| aaaagaacgt | ttggtggtat | accaacaatt | cttgaagaag | aagattccat | tgaaactgct | 1920 |
| tcgctaggtc | gacgacgac | tgattctatt | ggttatccg | acacatcatc | agaagattcg | 1980 |
| cattatggta | atgctaagaa | ggtaacatga | | | | 2010 |

<210> SEQ ID NO 36
<211> LENGTH: 616
<212> TYPE: PRT
<213> ORGANISM: Saccharomyces cerevisiae

<400> SEQUENCE: 36

```
Met Ser Ser Ser Ile Thr Asp Glu Lys Ile Ser Gly Glu Gln Gln Gln
  1               5                  10                  15

Pro Ala Gly Arg Lys Leu Tyr Tyr Asn Thr Ser Thr Phe Ala Glu Pro
             20                  25                  30

Pro Leu Val Asp Gly Glu Gly Asn Pro Ile Asn Tyr Glu Pro Glu Val
         35                  40                  45

Tyr Asn Pro Asp His Glu Lys Leu Tyr His Asn Pro Ser Leu Pro Ala
     50                  55                  60

Gln Ser Ile Gln Asp Thr Arg Asp Glu Leu Leu Glu Arg Val Tyr
 65                  70                  75                  80

Ser Gln Asp Gln Gly Val Glu Tyr Glu Asp Glu Asp Lys Pro
                 85                  90                  95

Asn Leu Ser Ala Ala Ser Ile Lys Ser Tyr Ala Leu Thr Arg Phe Thr
            100                 105                 110

Ser Leu Leu His Ile His Glu Phe Ser Trp Glu Asn Val Asn Pro Ile
        115                 120                 125

Pro Glu Leu Arg Lys Met Thr Trp Gln Asn Trp Asn Tyr Phe Phe Met
    130                 135                 140

Gly Tyr Phe Ala Trp Leu Ser Ala Ala Trp Ala Phe Phe Cys Val Ser
145                 150                 155                 160

Val Ser Val Ala Pro Leu Ala Glu Leu Tyr Asp Arg Pro Thr Lys Asp
                165                 170                 175

Ile Thr Trp Gly Leu Gly Leu Val Leu Phe Val Arg Ser Ala Gly Ala
            180                 185                 190

Val Ile Phe Gly Leu Trp Thr Asp Lys Ser Ser Arg Lys Trp Pro Tyr
        195                 200                 205

Ile Thr Cys Leu Phe Leu Phe Val Ile Ala Gln Leu Cys Thr Pro Trp
    210                 215                 220

Cys Asp Thr Tyr Glu Lys Phe Leu Gly Val Arg Trp Ile Thr Gly Ile
225                 230                 235                 240

Ala Met Gly Gly Ile Tyr Gly Cys Ala Ser Ala Thr Ala Ile Glu Asp
                245                 250                 255

Ala Pro Val Lys Ala Arg Ser Phe Leu Ser Gly Leu Phe Phe Ser Ala
            260                 265                 270

Tyr Ala Met Gly Phe Ile Phe Ala Ile Ile Phe Tyr Arg Ala Phe Gly
        275                 280                 285

Tyr Phe Arg Asp Asp Gly Trp Lys Ile Leu Trp Phe Ser Ile Phe
    290                 295                 300

Leu Pro Ile Leu Leu Ile Phe Trp Arg Leu Leu Trp Pro Glu Thr Lys
305                 310                 315                 320

Tyr Phe Thr Lys Val Leu Lys Ala Arg Lys Leu Ile Leu Ser Asp Ala
                325                 330                 335

Val Lys Ala Asn Gly Gly Glu Pro Leu Pro Lys Ala Asn Phe Lys Gln
            340                 345                 350

Lys Met Val Ser Met Lys Arg Thr Val Gln Lys Tyr Trp Leu Leu Phe
        355                 360                 365

Ala Tyr Leu Val Val Leu Leu Val Gly Pro Asn Tyr Leu Thr His Ala
```

```
                    370              375              380
Ser Gln Asp Leu Leu Pro Thr Met Leu Arg Ala Gln Leu Gly Leu Ser
385                 390              395              400

Lys Asp Ala Val Thr Val Ile Val Val Val Thr Asn Ile Gly Ala Ile
                405              410              415

Cys Gly Gly Met Ile Phe Gly Gln Phe Met Glu Val Thr Gly Arg Arg
            420              425              430

Leu Gly Leu Leu Ile Ala Cys Thr Met Gly Gly Cys Phe Thr Tyr Pro
        435              440              445

Ala Phe Met Leu Arg Ser Glu Lys Ala Ile Leu Gly Ala Gly Phe Met
450                 455              460

Leu Tyr Phe Cys Val Phe Gly Val Trp Gly Ile Leu Pro Ile His Leu
465                 470              475              480

Ala Glu Leu Ala Pro Ala Asp Ala Arg Ala Leu Val Ala Gly Leu Ser
                485              490              495

Tyr Gln Leu Gly Asn Leu Ala Ser Ala Ala Ala Ser Thr Ile Glu Thr
            500              505              510

Gln Leu Ala Asp Arg Tyr Pro Leu Glu Arg Asp Ala Ser Gly Ala Val
        515              520              525

Ile Lys Glu Asp Tyr Ala Lys Val Met Ala Ile Leu Thr Gly Ser Val
    530              535              540

Phe Ile Phe Thr Phe Ala Cys Val Phe Val Gly His Glu Lys Phe His
545                 550              555              560

Arg Asp Leu Ser Ser Pro Val Met Lys Lys Tyr Ile Asn Gln Val Glu
                565              570              575

Glu Tyr Glu Ala Asp Gly Leu Ser Ile Ser Asp Ile Val Glu Gln Lys
            580              585              590

Thr Glu Cys Ala Ser Val Lys Met Ile Asp Ser Asn Val Ser Lys Thr
        595              600              605

Tyr Glu Glu His Ile Glu Thr Val
    610              615

<210> SEQ ID NO 37
<211> LENGTH: 1851
<212> TYPE: DNA
<213> ORGANISM: Saccharomyces cerevisiae

<400> SEQUENCE: 37
atgtcgtcgt caattacaga tgagaaaata tctggtgaac agcaacaacc tgctggcaga      60
aaactatact ataacacaag tacatttgca gagcctcctc tagtggacgg agaaggtaac     120
cctataaatt atgagccgga agtttacaac ccggatcacg aaaagctata ccataaccca     180
tcactgcctg cacaatcaat tcaggataca agagatgatg aattgctgga agagttttat     240
agccaggatc aaggtgtaga gtatgaggaa gatgaagagg ataagccaaa cctaagcgct     300
gcgtccatta aagttatgc tttaacgaga tttacgtcct tactgcacat ccacgagttt     360
tcttgggaga atgtcaatcc catacccgaa ctgcgcaaaa tgacatggca gaattggaac     420 tatttttta tgggttattt tgcgtggttg tctgcggctt gggccttctt ttgcgttca     480 gtatcagtcg ctccattggc tgaactatat gacagaccaa ccaaggacat cacctggggg     540
ttgggattgg tgttatttgt tcgttcagca ggtgctgtca tatttggttt atggacagat     600
aagtcttcca gaaagtggcc gtacattaca tgtttgttct tatttgtcat tgcacaactc     660
tgtactccat ggtgtgacac atacgagaaa tttctgggcg taaggtggat aaccggtatt     720
```

```
gctatgggag gaatttacgg atgtgcttct gcaacagcga ttgaagatgc acctgtgaaa    780
gcacgttcgt tcctatcagg tctattttt tctgcttacg ctatggggtt catatttgct    840
atcatttttt acagagcctt tggctacttt agggatgatg gctggaaaat attgttttgg    900
tttagtattt ttctaccaat tctactaatt ttctggagat tgttatggcc tgaaacgaaa    960
tacttcacca aggttttgaa agcccgtaaa ttaatattga gtgacgcagt gaaagctaat   1020
ggtggcgagc ctctaccaaa agccaacttt aaacaaaaga tggtatccat gaagagaaca   1080
gttcaaaagt actggttgtt gttcgcatat ttggttgttt tattggtggg tccaaattac   1140
ttgactcatg cttctcaaga cttgttgcca accatgctgc gtgcccaatt aggcctatcc   1200
aaggatgctg tcactgtcat tgtagtggtt accaacatcg gtgctatttg tgggggtatg   1260
atatttggac agttcatgga agttactgga agaagattag gcctattgat tgcatgcaca   1320
atgggtggtt gcttcaccta ccctgcattt atgttgagaa gcgaaaaggc tatattaggt   1380
gccggtttca tgttatattt ttgtgtcttt ggtgtctggg gtatcctgcc cattcacctt   1440
gcagagttgg cccctgctga tgcaagggct ttggttgccg gttatctta ccagctaggt   1500 aatctagctt ctgcagcggc ttccacgatt gagacacagt tagctgatag atacccatta   1560
gaaagagatg cctctggtgc tgtgattaaa gaagattatg ccaaagttat ggctatcttg   1620
actggttctg ttttcatctt cacatttgct tgtgttttg ttggccatga gaaattccat   1680
cgtgatttgt cctctcctgt tatgaagaaa tatataaacc aagtggaaga atacgaagcc   1740
gatggtcttt cgattagtga cattgttgaa caaaagacgg aatgtgcttc agtgaagatg   1800
attgattcga acgtctcaaa gacatatgag gagcatattg agaccgttta a            1851

<210> SEQ ID NO 38
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 38
atttggcgag cgttggttgg tggatcaagc ccacgcgtag gcaatcctcg agcagatccg     60
ccaggcgtgt atatatagcg tggatggcca ggcaacttta gtgctgacac atacaggcat    120
atatatatgt gtgcgacgac acatgatcat atggcatgca tgtgctctgt atgtatataa    180
aactcttgtt ttcttctttt ctctaaatat tctttcctta tacattagga cctttgcagc    240
ataaattact atacttctat agacacgcaa acacaaatac acacactaa                289

<210> SEQ ID NO 39
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 39
atagcttcaa aatgtttcta ctcctttttt actcttccag attttctcgg actccgcgca     60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180
tctttttctt cgtcgaaaaa ggcaataaaa atttttatca cgtttctttt tcttgaaaat    240
tttttttttg attttttttct ctttcgatga cctcccattg atatttaagt taataaacgg    300
tcttcaattt ctcaagtttc agtttcattt ttcttgttct attacaactt tttttacttc    360
```
ttgctcatta gaaagaaagc atagcaatct aatctaagtt t                401

<210> SEQ ID NO 40
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 40

| | | | | | |
|---|---|---|---|---|---|
| agtttatcat | tatcaatact | cgccatttca | aagaatacgt | aaataattaa | tagtagtgat | 60 |
| tttcctaact | ttatttagtc | aaaaaattag | ccttttaatt | ctgctgtaac | ccgtacatgc | 120 |
| ccaaaatagg | gggcgggtta | cacagaatat | ataacatcgt | aggtgtctgg | gtgaacagtt | 180 |
| tattcctggc | atccactaaa | tataatgag | cccgcttttt | aagctggcat | ccagaaaaaa | 240 |
| aaagaatccc | agcaccaaaa | tattgttttc | ttcaccaacc | atcagttcat | aggtccattc | 300 |
| tcttagcgca | actacagaga | acaggggcac | aaacaggcaa | aaacgggca | caacctcaat | 360 |
| ggagtgatgc | aacctgcctg | gagtaaatga | tgacacaagg | caattgaccc | acgcatgtat | 420 |
| ctatctcatt | ttcttacacc | ttctattacc | ttctgctctc | tctgatttgg | aaaaagctga | 480 |
| aaaaaaggt | tgaaccagt | tccctgaaat | tattcccta | cttgactaat | aagtatataa | 540 |
| agacggtagg | tattgattgt | aattctgtaa | atctatttct | taaacttctt | aaattctact | 600 |
| tttatagtta | gtcttttttt | tagttttaaa | acaccagaac | ttagtttcga | cggat | 655 |

<210> SEQ ID NO 41
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 41

| | | | | | |
|---|---|---|---|---|---|
| gccgggatcg | aagaaatgat | ggtaaatgaa | ataggaaatc | aaggagcatg | aaggcaaaag | 60 |
| acaaatataa | gggtcgaacg | aaaaataaag | tgaaagtgt | tgatatgatg | tatttggctt | 120 |
| tgcggcgccg | aaaaaacgag | tttacgcaat | tgcacaatca | tgctgactct | gtggcggacc | 180 |
| cgcgctcttg | ccggcccggc | gataacgctg | ggcgtgaggc | tgtgcccggc | ggagtttttt | 240 |
| gcgcctgcat | tttccaaggt | ttaccctgcg | ctaaggggcg | agattggaga | agcaataaga | 300 |
| atgccggttg | gggttgcgat | gatgacgacc | acgacaactg | gtgtcattat | ttaagttgcc | 360 |
| gaaagaacct | gagtgcattt | gcaacatgag | tatactagaa | gaatgagcca | agacttgcga | 420 |
| gacgcgagtt | tgccggtggt | gcgaacaata | gagcgaccat | gaccttgaag | gtgagacgcg | 480 |
| cataaccgct | agagtacttt | gaagaggaaa | cagcaatagg | gttgctacca | gtataaatag | 540 |
| acaggtacat | acaacactgg | aaatggttgt | ctgtttgagt | acgctttcaa | ttcatttggg | 600 |
| tgtgcacttt | attatgttac | aatatggaag | ggaactttac | acttctccta | tgcacatata | 660 |
| ttaattaaag | tccaatgcta | gtagagaagg | ggggtaacac | ccctccgcgc | tcttttccga | 720 |
| ttttttctta | aaccgtggaa | tatttcggat | atccttttgt | tgtttccggg | tgtacaatat | 780 |
| ggacttcctc | ttttctggca | accaaaccca | tacatcggga | ttcctataat | accttcgttg | 840 |
| gtctccctaa | catgtaggtg | gcggagggga | gatatacaat | agaacagata | ccagacaaga | 900 |
| cataatgggc | taaacaagac | tacaccaatt | acactgcctc | attgatggtg | gtacataacg | 960 |
| aactaatact | gtagccctag | acttgatagc | catcatcata | tcgaagtttc | actacccttt | 1020 |

| | |
|---|---:|
| ttccatttgc catctattga agtaataata ggcgcatgca acttctttc tttttttttc | 1080 |
| ttttctctct ccccgttgt tgtctcacca tatccgcaat gacaaaaaaa tgatggaaga | 1140 |
| cactaaagga aaaaattaac gacaaagaca gcaccaacag atgtcgttgt tccagagctg | 1200 |
| atgaggggta tctcgaagca cacgaaactt tttccttcct tcattcacgc acactactct | 1260 |
| ctaatgagca acggtatacg gccttccttc cagttacttg aatttgaaat aaaaaaaagt | 1320 |
| ttgctgtctt gctatcaagt ataaatagac ctgcaattat taatcttttg tttcctcgtc | 1380 |
| attgttctcg ttcccttct ccttgtttc tttttctgca caatatttca agctatacca | 1440 |
| agcatacaat caactccaag ctggccgc | 1468 |

<210> SEQ ID NO 42
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 42

| | |
|---|---:|
| ttcgcggcca cctacgccgc tatctttgca acaactatct gcgataactc agcaaatttt | 60 |
| gcatattcgt gttgcagtat tgcgataatg ggagtcttac ttccaacata acggcagaaa | 120 |
| gaaatgtgag aaaattttgc atcctttgcc tccgttcaag tatataaagt cggcatgctt | 180 |
| gataatcttt ctttccatcc tacattgttc taattattct tattctcctt tattctttcc | 240 |
| taacatacca agaaattaat cttctgtcat tcgcttaaac actatatcaa ta | 292 |

<210> SEQ ID NO 43
<211> LENGTH: 798
<212> TYPE: DNA
<213> ORGANISM: Artificial Sequence
<220> FEATURE:
<223> OTHER INFORMATION: Synthetic PGK promoter

<400> SEQUENCE: 43

| | |
|---|---:|
| ctttcctctt tttattaacc ttaatttta ttttagattc ctgacttcaa ctcaagacgc | 60 |
| acagatatta taacatctgc ataataggca tttgcaagaa ttactcgtga gtaaggaaag | 120 |
| agtgaggaac tatcgcatac ctgcatttaa agatgccgat ttgggcgcga atcctttatt | 180 |
| ttggcttcac cctcatacta ttatcagggc cagaaaaagg aagtgtttcc ctccttcttg | 240 |
| aattgatgtt accctcataa agcacgtggc ctcttatcga gaagaaatt accgtcgctc | 300 |
| gtgatttgtt tgcaaaaaga acaaaactga aaaaacccag acacgctcga cttcctgtct | 360 |
| tcctattgat tgcagcttcc aatttcgtca cacaacaagg tcctagcgac ggctcacagg | 420 |
| ttttgtaaca agcaatcgaa ggttctggaa tggcgggaaa gggtttagta ccacatgcta | 480 |
| tgatgcccac tgtgatctcc agagcaaagt tcgttcgatc gtactgttac tctctctctt | 540 |
| tcaaacagaa ttgtccgaat cgtgtgacaa caacagcctg ttctcacaca ctcttttctt | 600 |
| ctaaccaagg gggtggttta gtttagtaga acctcgtgaa acttacattt acatatatat | 660 |
| aaacttgcat aaattggtca atgcaagaaa tacatatttg gtcttttcta attcgtagtt | 720 |
| tttcaagttc ttagatgctt tcttttttctc ttttttacag atcatcaagg aagtaattat | 780 |
| ctactttta caacaaat | 798 |

<210> SEQ ID NO 44
<211> LENGTH: 252
<212> TYPE: DNA
<213> ORGANISM: Artificial Sequence -continued

```
<220> FEATURE:
<223> OTHER INFORMATION: Synthetic CYC1 terminator

<400> SEQUENCE: 44
tcatgtaatt agttatgtca cgcttacatt cacgccctcc ccccacatcc gctctaaccg      60
aaaaggaagg agttagacaa cctgaagtct aggtccctat ttattttttt atagttatgt     120
tagtattaag aacgttattt atatttcaaa ttttcttttt ttttctgtac agacgcgtgt     180
acgcatgtaa cattatactg aaaaccttgc ttgagaaggt tttgggacgc tcgaaggctt     240
taatttgcgg cc                                                        252

<210> SEQ ID NO 45
<211> LENGTH: 31
<212> TYPE: DNA
<213> ORGANISM: Artificial Sequence
<220> FEATURE:
<223> OTHER INFORMATION: primer

<400> SEQUENCE: 45
cgagctcttc gcggccacct acgccgctat c                                    31

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
gctctagata ttgatatagt gtttaagcga at                                   32

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
cggccatggc gggagctcgc atgcaag                                         27

<210> SEQ ID NO 48
<211> LENGTH: 28
<212> TYPE: DNA
<213> ORGANISM: Artificial Sequence
<220> FEATURE:
<223> OTHER INFORMATION: primer

<400> SEQUENCE: 48
cgggatatca ctagtgagct cgctccgc                                        28

<210> SEQ ID NO 49
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 49
gccgggagag ctcgcatgca agtaacctat tcaaagtaat atctcataca tgtttcatga     60
gggtaacaac atgcgactgg gtgagcatat gttccgctga tgtgatgtgc aagataaaca    120
agcaaggcag aaactaactt cttcttcatg taataaacac accccgcgtt tatttaccta    180
```

```
tctctaaact tcaacacctt atatcataac taatatttct tgagataagc acactgcacc    240
catacctttcc ttaaaaacgt agcttccagt ttttggtggt tccggcttcc ttcccgattc    300
cgcccgctaa acgcatattt ttgttgcctg gtggcatttg caaaatgcat aacctatgca    360
tttaaaagat tatgtatgct cttctgactt ttcgtgtgat gaggctcgtg gaaaaaatga    420
ataatttatg aatttgagaa caattttgtg ttgttacggt attttactat ggaataatca    480
atcaattgag gattttatgc aaatatcgtt tgaatatttt tccgacccct tgagtacttt    540
tcttcataat tgcataatat tgtccgctgc ccctttttct gttagacggt gtcttgatct    600
acttgctatc gttcaacacc acctattttt ctaactattt ttttttttagc tcatttgaat    660
cagcttatgg tgatggcaca tttttgcata aacctagctg tcctcgttga acataggaaa    720
aaaaaatata taacaaggc tctttcactc tccttgcaat cagatttggg tttgttccct    780
ttatttttcat atttcttgtc atattccttt ctcaattatt attttctact cataacctca    840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa   1020
tagctgcgcc gatggtttct acaaagatcg ttatgttat cggcactttg catcggccgc   1080
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta gccagacgag   1260
cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc caacaatgtc ctgacggaca atggccgcat   1500
aacagcggtc attgactgga gcgaggcgat gttcggggat tcccaatacg aggtcgccaa   1560
catcttcttc tggaggccgt ggttggcttg tatggagcag cagacgcgct acttcgagcg   1620
gaggcatccg gagcttgcag gatcgccgcg gctccgggcg tatatgctcc gcattggtct   1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat ggggaggct aactgaggat ccgtagatac   1920
attgatgcta tcaatcaaga gaactggaaa gattgtgtaa ccttgaaaaa cggtgaaact   1980
tacgggtcca agattgtcta cagattttcc tgatttgcca gcttactatc cttcttgaaa   2040
atatgcactc tatatctttt agttcttaat tgcaacacat agatttgctg tataacgaat   2100
tttatgctat ttttaaatt tggagttcag tgataaaagt gtcacagcga atttcctcac   2160
atgtagggac cgaattgttt acaagttctc tgtaccacca tggagacatc aaaaattgaa   2220
aatctatgga aagatatgga cggtagcaac aagaatatag cacgagccgc ggagcgagct   2280
cggccgcact agtgatatcc cgcggccatg gcggccggga g                        2321
```

<210> SEQ ID NO 50
<211> LENGTH: 18
<212> TYPE: DNA
<213> ORGANISM: Artificial Sequence
<220> FEATURE:
<223> OTHER INFORMATION: primer

<400> SEQUENCE: 50
gaaacagcta tgaccatg                                                      18

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
gacatgacga gctcgaattg ggtaccggcc gc                                      32

<210> SEQ ID NO 52
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 52

| | | | | | |
|---|---|---|---|---|---|
| gatgacggtg | aaaacctctg | acacatgcag | ctcccggaga | cggtcacagc | ttgtctgtaa    60 |
| gcggatgccg | ggagcagaca | agcccgtcag | ggcgcgtcag | cgggtgttgg | cgggtgtcgg   120 |
| ggctggctta | actatgcggc | atcagagcag | attgtactga | gagtgcacca | tatgcggtgt   180 |
| gaaataccgc | acagatgcgt | aaggagaaaa | taccgcatca | ggcgccattc | gccattcagg   240 |
| ctgcgcaact | gttgggaagg | gcgatcggtg | cgggcctctt | cgctattacg | ccagctggcg   300 |
| aaagggggat | gtgctgcaag | gcgattaagt | tgggtaacgc | cagggttttc | ccagtcacga   360 |
| cgttgtaaaa | cgacggccag | tgaattcgag | ctcggtacct | cgcgaatgca | tctagatatc   420 |
| ggatcccgac | gagctgcacc | gcggtggcgg | ccgtatcttt | acccatacg | atgttcctga   480 |
| ctatgcgggc | tatcccctatg | acgtcccgga | ctatgcagga | tcctatccat | atgacgttcc   540 |
| agattacgct | gctcagtgcg | gccgcctgag | agtgcaccat | accacagctt | tcaattcaa   600 |
| ttcatcattt | ttttttttatt | cttttttttg | atttcggttt | ctttgaaatt | ttttttgattc   660 |
| ggtaatctcc | gaacagaagg | aagaacgaag | gaaggagcac | agacttagat | tggtatatat   720 |
| acgcatatgt | agtgttgaag | aaacatgaaa | ttgcccagta | ttcttaaccc | aactgcacag   780 |
| aacaaaaacc | tgcaggaaac | gaagataaat | catgtcgaaa | gctacatata | aggaacgtgc   840 |
| tgctactcat | cctagtcctg | ttgctgccaa | gctatttaat | atcatgcacg | aaaagcaaac   900 |
| aaacttgtgt | gcttcattgg | atgttcgtac | caccaaggaa | ttactggagt | tagttgaagc   960 |
| attaggtccc | aaaatttgtt | tactaaaaac | acatgtggat | atcttgactg | atttttccat  1020 |
| ggagggcaca | gttaagccgc | taaaggcatt | atccgccaag | tacaattttt | tactcttcga  1080 |
| agacagaaaa | tttgctgaca | ttggtaatac | agtcaaattg | cagtactctg | cgggtgtata  1140 |
| cagaatagca | gaatgggcag | acattacgaa | tgcacgggt | gtggtgggcc | caggtattgt  1200 |
| tagcggtttg | aagcaggcgg | cagaagaagt | aacaaaggaa | cctagaggcc | ttttgatgtt  1260 |
| agcagaattg | tcatgcaagg | gctccctatc | tactggagaa | tatactaagg | gtactgttga  1320 |
| cattgcgaag | agcgacaaag | attttgttat | cggctttatt | gctcaaagag | acatgggtgg  1380 |
| aagagatgaa | ggttacgatt | ggttgattat | gacacccggt | gtgggtttag | atgacaaggg  1440 |
| agacgcattg | ggtcaacagt | atagaaccgt | ggatgatgtg | gtctctacag | gatctgacat  1500 |
| tattattgtt | ggaagaggac | tatttgcaaa | gggaagggat | gctaaggtag | agggtgaacg  1560 |

```
ttacagaaaa gcaggctggg aagcatattt gagaagatgc ggccagcaaa actaaaaaac    1620
tgtattataa gtaaatgcat gtatactaaa ctcacaaatt agagcttcaa tttaattata    1680
tcagttatta ccctatgcgg tgtgaaatac cgcacagatg cgtaaggaga aaataccgca    1740
tcaggaaatt gtagcggccg cgaatttgag cttatctttt acccatacga tgttcctgac    1800
tatgcgggct atccctatga cgtcccggac tatgcaggat cctatccata tgacgttcca    1860
gattacgcta ctagcggggg gcccggtgac gggcccgtcg actgcagagg cctgcatgca    1920
agcttggcgt aatcatggtc atagctgttt cctgtgtgaa attgttatcc gctcacaatt    1980
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg ggagaggcg gtttgcgtat tgggcgctct     2160
tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata agataccag gcgtttcccc ctggaagctc cctcgtgcgc     2460
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc caacgatca    3480
aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
```

```
ctcttcctttt ttcaatatta ttgaagcatt tatcagggtt attgtctcat gagcggatac    4020
atatttgaat gtatttagaa aaataaacaa atagggggtc cgcgcacatt tccccgaaaa    4080
gtgccacctg acgtctaaga aaccattatt atcatgacat taacctataa aaataggcgt    4140
atcacgaggc cctttcgtct cgcgcgtttc ggt                                  4173
```

<210> SEQ ID NO 53
<211> LENGTH: 62
<212> TYPE: DNA
<213> ORGANISM: Artificial Sequence
<220> FEATURE:
<223> OTHER INFORMATION: primer

<400> SEQUENCE: 53

```
gcttataaaa ctttaactaa taattagaga ttaaatcgct taaggtttcc cgactggaaa    60
gc                                                                    62
```

<210> SEQ ID NO 54
<211> LENGTH: 64
<212> TYPE: DNA
<213> ORGANISM: Artificial Sequence
<220> FEATURE:
<223> OTHER INFORMATION: primer

<400> SEQUENCE: 54

```
ctactcataa cctcacgcaa aataacacag tcaaatcaat caaaccagtc acgacgttgt    60
aaaa                                                                  64
```

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55

```
ggacgtaaag ggtagcctcc                                                 20
```

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56

```
gaagcggacc cagacttaag cc                                              22
```

<210> SEQ ID NO 57
<211> LENGTH: 65
<212> TYPE: DNA
<213> ORGANISM: Artificial Sequence
<220> FEATURE:
<223> OTHER INFORMATION: primer

<400> SEQUENCE: 57

```
ccgaaatgat tcccttttcct gcacaacacg agatctttca cgcatccagt cacgacgttg    60
taaaa                                                                 65
```

<210> SEQ ID NO 58
<211> LENGTH: 64
<212> TYPE: DNA

```
<213> ORGANISM: Artificial Sequence
<220> FEATURE:
<223> OTHER INFORMATION: primer

<400> SEQUENCE: 58
aaagtagcct taaagctagg ctataatcat gcatcctcaa attctaggtt tcccgacgga    60
aagc                                                                 64

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
cgcaagaacg tagtatccac atgcc                                          25

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
ggatatttac agaacgatgc g                                              21

<210> SEQ ID NO 61
<211> LENGTH: 70
<212> TYPE: DNA
<213> ORGANISM: Artificial Sequence
<220> FEATURE:
<223> OTHER INFORMATION: primer

<400> SEQUENCE: 61
ccctatgtct ctggccgatc acgcgccatt gtccctcaga aacaaatcaa ccagtcacga    60
cgttgtaaaa                                                           70

<210> SEQ ID NO 62
<211> LENGTH: 70
<212> TYPE: DNA
<213> ORGANISM: Artificial Sequence
<220> FEATURE:
<223> OTHER INFORMATION: primer

<400> SEQUENCE: 62
tagaagcaac tgtgccgaca gcctctgaat gagtggtgtt gtaaccaccc aggtttcccg    60
actggaaagc                                                           70

<210> SEQ ID NO 63
<211> LENGTH: 25
<212> TYPE: DNA
<213> ORGANISM: Artificial Sequence
<220> FEATURE:
<223> OTHER INFORMATION: primer

<400> SEQUENCE: 63
tcaatgagac tgttgtcctc ctact                                          25

<210> SEQ ID NO 64
<211> LENGTH: 24
<212> TYPE: DNA
<213> ORGANISM: Artificial Sequence
```

```
<220> FEATURE:
<223> OTHER INFORMATION: primer

<400> SEQUENCE: 64
tacatccttg tcgagccttg ggca                                              24

<210> SEQ ID NO 65
<211> LENGTH: 60
<212> TYPE: DNA
<213> ORGANISM: Artificial Sequence
<220> FEATURE:
<223> OTHER INFORMATION: primer

<400> SEQUENCE: 65
atgattagac aatcattaat gaaaacagtg tgggctaact ccagtcacga cgttgtaaaa       60

<210> SEQ ID NO 66
<211> LENGTH: 60
<212> TYPE: DNA
<213> ORGANISM: Artificial Sequence
<220> FEATURE:
<223> OTHER INFORMATION: primer

<400> SEQUENCE: 66
ctagatagat gaatctctac ccaagaaata aactttagcc aggtttcccg actggaaagc       60

<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
actgatcatc atttaaaaat gt                                                22

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
aaggaaaaaa attttcacac ta                                                22

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
atgctgccca gacttggttt tgcgaggact gctaggtcca tacaccgttt ccagtcacga       60
cgttgtaaaa                                                              70

<210> SEQ ID NO 70
<211> LENGTH: 60
<212> TYPE: DNA
<213> ORGANISM: Artificial Sequence
<220> FEATURE:
<223> OTHER INFORMATION: primer

<400> SEQUENCE: 70
```
ctacacggag gaatcccttc caagaaagta aactttggtc aggtttcccg actggaaagc    60

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
caggaacata gtagaaagac    20

<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
taacgcgaat cttccatg    18

<210> SEQ ID NO 73
<211> LENGTH: 65
<212> TYPE: DNA
<213> ORGANISM: Artificial Sequence
<220> FEATURE:
<223> OTHER INFORMATION: primer

<400> SEQUENCE: 73
aatgtctcaa ccggttcaac gcgctgcagc acgctcattc cttcaaagag ctgcaccgcg    60
gtggc    65

<210> SEQ ID NO 74
<211> LENGTH: 65
<212> TYPE: DNA
<213> ORGANISM: Artificial Sequence
<220> FEATURE:
<223> OTHER INFORMATION: primer

<400> SEQUENCE: 74
ttactgttta ccagtttttt ctttctcttt ccattcctta tctagagacc gggccccccg    60
ctagt    65

<210> SEQ ID NO 75
<211> LENGTH: 19
<212> TYPE: DNA
<213> ORGANISM: Artificial Sequence
<220> FEATURE:
<223> OTHER INFORMATION: primer

<400> SEQUENCE: 75
ggacgtggcc tgtaaagtt    19

<210> SEQ ID NO 76
<211> LENGTH: 23
<212> TYPE: DNA
<213> ORGANISM: Artificial Sequence
<220> FEATURE:
<223> OTHER INFORMATION: primer

<400> SEQUENCE: 76
agaatatgca tgaacatatc cat    23

<210> SEQ ID NO 77
<211> LENGTH: 64
<212> TYPE: DNA
<213> ORGANISM: Artificial Sequence
<220> FEATURE:
<223> OTHER INFORMATION: primer

<400> SEQUENCE: 77
aatgtctaca tcatccgtac gttttgcatt taggcggttc tggcaagagc tgcaccgcgg    60
tggc    64

<210> SEQ ID NO 78
<211> LENGTH: 66
<212> TYPE: DNA
<213> ORGANISM: Artificial Sequence
<220> FEATURE:
<223> OTHER INFORMATION: primer

<400> SEQUENCE: 78
ttatctgccc gtagtaattt cctttttgct ttctgcggcg ccgctgagac cgggcccccc    60
gctagt    66

<210> SEQ ID NO 79
<211> LENGTH: 18
<212> TYPE: DNA
<213> ORGANISM: Artificial Sequence
<220> FEATURE:
<223> OTHER INFORMATION: primer

<400> SEQUENCE: 79
ctattgcgcg catgacta    18

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
tgcattgcct tctattatcc    20

<210> SEQ ID NO 81
<211> LENGTH: 34
<212> TYPE: DNA
<213> ORGANISM: Artificial Sequence
<220> FEATURE:
<223> OTHER INFORMATION: primer

<400> SEQUENCE: 81
aattgaattc atggcaacat taaaagatca acta    34

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
aattgtcgac ttagaattgt aattcctttt ggatg    35

<210> SEQ ID NO 83
<211> LENGTH: 26
<212> TYPE: DNA

```
<213> ORGANISM: Artificial Sequence
<220> FEATURE:
<223> OTHER INFORMATION: primer

<400> SEQUENCE: 83
gagctcaatt aaccctcact aaaggg                                          26

<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
gagctccaaa ttaaagcctt cgagcg                                          26

<210> SEQ ID NO 85
<211> LENGTH: 69
<212> TYPE: DNA
<213> ORGANISM: Artificial Sequence
<220> FEATURE:
<223> OTHER INFORMATION: primer

<400> SEQUENCE: 85
tgagcacgtg agtatacgtg attaagcaca caaaggcagc ttggagtatg gtgctgcaag     60
gcgattaag                                                             69

<210> SEQ ID NO 86
<211> LENGTH: 67
<212> TYPE: DNA
<213> ORGANISM: Artificial Sequence
<220> FEATURE:
<223> OTHER INFORMATION: primer

<400> SEQUENCE: 86
aggcaagtgc acaaacaata cttaaataaa tactactcag taataacccg gctcgtatgt     60
tgtgtgg                                                               67

<210> SEQ ID NO 87
<211> LENGTH: 21
<212> TYPE: DNA
<213> ORGANISM: Artificial Sequence
<220> FEATURE:
<223> OTHER INFORMATION: primer

<400> SEQUENCE: 87
gccaaatgat ttagcattat c                                               21

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
aaaaggagag ggccaagagg g                                               21

<210> SEQ ID NO 89
<211> LENGTH: 296
<212> TYPE: DNA
<213> ORGANISM: Saccharomyces cerevisiae

<400> SEQUENCE: 89
```

```
tttggcgagc gttggttggt ggatcaagcc cacgcgtagg caatcctcga gcagatccgc    60
caggcgtgta tatatagcgt ggatggccag gcaactttag tgctgacaca tacaggcata   120
tatatatgtg tgcgacgaca catgatcata tggcatgcat gtgctctgta tgtatataaa   180
actcttgttt tcttcttttc tctaaatatt ctttccttat acattaggac ctttgcagca   240
taaattacta tacttctata gacacacaaa cacaaataca cacactaaat taataa       296
```

<210> SEQ ID NO 90
<211> LENGTH: 27
<212> TYPE: DNA
<213> ORGANISM: Artificial Sequence
<220> FEATURE:
<223> OTHER INFORMATION: primer

<400> SEQUENCE: 90

```
cggaattcat ttggcgagcg ttggttg                                        27
```

<210> SEQ ID NO 91
<211> LENGTH: 31
<212> TYPE: DNA
<213> ORGANISM: Artificial Sequence
<220> FEATURE:
<223> OTHER INFORMATION: primer

<400> SEQUENCE: 91

```
cggaattctt agtgtgtgta tttgtgtttg c                                   31
```

<210> SEQ ID NO 92
<211> LENGTH: 60
<212> TYPE: DNA
<213> ORGANISM: Artificial Sequence
<220> FEATURE:
<223> OTHER INFORMATION: primer

<400> SEQUENCE: 92

```
cgtcacgtgt tttgccattt tgtacgacaa atgaaccgcc tcaaccctat ctcggtctat    60
```

<210> SEQ ID NO 93
<211> LENGTH: 66
<212> TYPE: DNA
<213> ORGANISM: Artificial Sequence
<220> FEATURE:
<223> OTHER INFORMATION: primer

<400> SEQUENCE: 93

```
tgaagttatc tctcaagccg gcgaattttc tttgcgacat gaattcttat taatttagtg    60
tgtgta                                                               66
```

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94

```
caatcatgtc ctcgacctta a                                              21
```

<210> SEQ ID NO 95
<211> LENGTH: 19
<212> TYPE: DNA
<213> ORGANISM: Artificial Sequence
<220> FEATURE:

<223> OTHER INFORMATION: primer

<400> SEQUENCE: 95
gaagatgttt cgctaaaag                                                   19

<210> SEQ ID NO 96
<211> LENGTH: 70
<212> TYPE: DNA
<213> ORGANISM: Artificial Sequence
<220> FEATURE:
<223> OTHER INFORMATION: primer

<400> SEQUENCE: 96
atgagtaatc ctcaaaaagc tctaaacgac tttctgtcca gtgaatctgt ccagtcacga      60
cgttgtaaaa                                                             70

<210> SEQ ID NO 97
<211> LENGTH: 70
<212> TYPE: DNA
<213> ORGANISM: Artificial Sequence
<220> FEATURE:
<223> OTHER INFORMATION: primer

<400> SEQUENCE: 97
tcatgttacc ttcttagcat taccataatg cgaatcttct gatgatgtgt aggtttcccg      60
actggaaagc                                                             70

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
atgagtaatc ctcaaaaagc                                                  20

<210> SEQ ID NO 99
<211> LENGTH: 17
<212> TYPE: DNA
<213> ORGANISM: Artificial Sequence
<220> FEATURE:
<223> OTHER INFORMATION: primer

<400> SEQUENCE: 99
tcatgttacc ttcttag                                                     17

<210> SEQ ID NO 100
<211> LENGTH: 627
<212> TYPE: DNA
<213> ORGANISM: Artificial Sequence
<220> FEATURE:
<223> OTHER INFORMATION: Synthetic TPI1 promoter

<400> SEQUENCE: 100
gctacccaaa tggactgatt gtgagggaga cctaactaca tagtgtttaa agattacgga      60
tatttaactt acttagaata atgccatttt tttgagttat aataatccta cgttagtgtg     120
agcgggattt aaactgtgag gaccttaata cattcagaca cttctgcggt atcaccctac     180
ttattccctt cgagattata tctaggaacc catcaggttg gtggaagatt acccgttcta     240
agacttttca gcttcctcta ttgatgttac acctggacac cccttttctg gcatccagtt     300
tttaatcttc agtggcatgt gagattctcc gaaattaatt aaagcaatca cacaattctc     360

```
tcggatacca cctcggttga aactgacagg tggtttgtta cgcatgctaa tgcaaaggag    420
cctatatacc tttggctcgg ctgctgtaac agggaatata aagggcagca aatttagga     480 gtttagtgaa cttgcaacat ttactatttt cccttcttac gtaaatattt ttcttttaa    540 ttctaaatca atcttttca attttttgtt tgtattcttt tcttgcttaa atctataact    600
acaaaaaaca catacataaa ctaaaaa                                        627
```

<210> SEQ ID NO 101
<211> LENGTH: 18
<212> TYPE: DNA
<213> ORGANISM: Artificial Sequence
<220> FEATURE:
<223> OTHER INFORMATION: primer

<400> SEQUENCE: 101

```
gtttaaagat tacggata                                                   18
```

<210> SEQ ID NO 102
<211> LENGTH: 27
<212> TYPE: DNA
<213> ORGANISM: Artificial Sequence
<220> FEATURE:
<223> OTHER INFORMATION: primer

<400> SEQUENCE: 102

```
tttttagttt atgtatgtgt tttttgt                                         27
```

<210> SEQ ID NO 103
<211> LENGTH: 2710
<212> TYPE: DNA
<213> ORGANISM: Artificial Sequence
<220> FEATURE:
<223> OTHER INFORMATION: Synthetic P57 vector

<400> SEQUENCE: 103

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tatcggatgc cgggaccgac gagtgcagag gcgtgcaagc gagcttggcg    480
taatcatggt catagctgtt tcctgtgtga aattgttatc cgctcacaat tccacacaac    540
atacgagccg gaagcataaa gtgtaaagcc tggggtgcct aatgagtgag ctaactcaca    600
ttaattgcgt tgcgctcact gcccgctttc cagtcgggaa acctgtcgtg ccagctgcat    660
taatgaatcg gccaacgcgc ggggagaggc ggtttgcgta ttgggcgctc ttccgcttcc    720
tcgctcactg actcgctgcg ctcggtcgtt cggctgcggc gagcggtatc agctcactca    780
aaggcggtaa tacggttatc cacagaatca ggggataacg caggaaagaa catgtgagca    840
aaaggccagc aaaaggccag gaaccgtaaa aaggccgcgt tgctggcgtt tttccatagg    900
ctccgccccc ctgacgagca tcacaaaaat cgacgctcaa gtcagaggtg gcgaaacccg    960
acaggactat aaagatacca ggcgtttccc cctggaagct ccctcgtgcg ctctcctgtt   1020
```

| | |
|---|---|
| ccgaccctgc cgcttaccgg atacctgtcc gcctttctcc cttcgggaag cgtggcgctt | 1080 |
| tctcatagct cacgctgtag gtatctcagt tcggtgtagg tcgttcgctc caagctgggc | 1140 |
| tgtgtgcacg aaccccccgt tcagcccgac cgctgcgcct tatccggtaa ctatcgtctt | 1200 |
| gagtccaacc cggtaagaca cgacttatcg ccactggcag cagccactgg taacaggatt | 1260 |
| agcagagcga ggtatgtagg cggtgctaca gagttcttga agtggtggcc taactacggc | 1320 |
| tacactagaa gaacagtatt tggtatctgc gctctgctga agccagttac cttcggaaaa | 1380 |
| agagttggta gctcttgatc cggcaaacaa accaccgctg gtagcggtgg ttttttttgtt | 1440 |
| tgcaagcagc agattacgcg cagaaaaaaa ggatctcaag aagatccttt gatcttttct | 1500 |
| acggggtctg acgctcagtg gaacgaaaac tcacgttaag ggattttggt catgagatta | 1560 |
| tcaaaaagga tcttcaccta gatcctttta aattaaaaat gaagttttaa atcaatctaa | 1620 |
| agtatatatg agtaaacttg gtctgacagt taccaatgct taatcagtga ggcacctatc | 1680 |
| tcagcgatct gtctatttcg ttcatccata gttgcctgac tccccgtcgt gtagataact | 1740 |
| acgatacggg agggcttacc atctggcccc agtgctgcaa tgataccgcg agacccacgc | 1800 |
| tcaccggctc cagatttatc agcaataaac cagccagccg gaagggccga gcgcagaagt | 1860 |
| ggtcctgcaa ctttatccgc ctccatccag tctattaatt gttgccggga agctagagta | 1920 |
| agtagttcgc cagttaatag tttgcgcaac gttgttgcca ttgctacagg catcgtggtg | 1980 |
| tcacgctcgt cgtttggtat ggcttcattc agctccggtt cccaacgatc aaggcgagtt | 2040 |
| acatgatccc ccatgttgtg caaaaaagcg gttagctcct tcggtcctcc gatcgttgtc | 2100 |
| agaagtaagt tggccgcagt gttatcactc atggttatgg cagcactgca taattctctt | 2160 |
| actgtcatgc catccgtaag atgcttttct gtgactggtg agtactcaac caagtcattc | 2220 |
| tgagaatagt gtatgcggcg accgagttgc tcttgcccgg cgtcaatacg ggataatacc | 2280 |
| gcgccacata gcagaacttt aaaagtgctc atcattggaa aacgttcttc ggggcgaaaa | 2340 |
| ctctcaagga tcttaccgct gttgagatcc agttcgatgt aacccactcg tgcacccaac | 2400 |
| tgatcttcag catcttttac tttcaccagc gtttctgggt gagcaaaaac aggaaggcaa | 2460 |
| aatgccgcaa aaaagggaat aagggcgaca cggaaatgtt gaatactcat actcttcctt | 2520 |
| tttcaatatt attgaagcat ttatcagggt tattgtctca tgagcggata catatttgaa | 2580 |
| tgtatttaga aaaataaaca aataggggtt ccgcgcacat ttccccgaaa agtgccacct | 2640 |
| gacgtctaag aaaccattat tatcatgaca ttaacctata aaaataggcg tatcacgagg | 2700 |
| ccctttcgtc | 2710 |

<210> SEQ ID NO 104
<211> LENGTH: 4777
<212> TYPE: DNA
<213> ORGANISM: Artificial Sequence
<220> FEATURE:
<223> OTHER INFORMATION: Synthetic P57-Ptpi1 vector

<400> SEQUENCE: 104

| | |
|---|---|
| gatgacggtg aaaacctctg acacatgcag ctcccggaga cggtcacagc ttgtctgtaa | 60 |
| gcggatgccg ggagcagaca gcccgtcag ggcgcgtcag cgggtgttgg cgggtgtcgg | 120 |
| ggctggctta actatgcggc atcagagcag attgtactga gagtgcacca tatgcggtgt | 180 |
| gaaataccgc acagatgcgt aaggagaaaa taccgcatca ggcgccattc gccattcagg | 240 |
| ctgcgcaact gttgggaagg gcgatcgtg cgggcctctt cgctattacg ccagctggcg | 300 |
| aaagggggat gtgctgcaag gcgattaagt tgggtaacgc cagggttttc ccagtcacga | 360 |

-continued

```
cgttgtaaaa cgacggccag tgaattcttt ttagtttatg tatgtgtttt ttgtagttat    420
agatttaagc aagaaaagaa tacaaacaaa aaattgaaaa agattgattt agaattaaaa    480
agaaaaatat ttacgtaaga agggaaaata gtaaatgttg caagttcact aaactcctaa    540
attatgctgc cctttatatt ccctgttaca gcagccgagc caaaggtata taggctcctt    600
tgcattagca tgcgtaacaa accacctgtc agtttcaacc gaggtggtat ccgagagaat    660
tgtgtgattg ctttaattaa tttcggagaa tctcacatgc cactgaagat taaaaactgg    720
atgccagaaa aggggtgtcc aggtgtaaca tcaatagagg aagctgaaaa gtcttagaac    780
gggtaatctt ccaccaacct gatgggttcc tagatataat ctcgaaggga ataagtaggg    840
tgataccgca gaagtgtctg aatgtattaa ggtcctcaca gtttaaatcc cgctcacact    900
aacgtaggat tattataact caaaaaaatg gcattattct aagtaagtta aatatccgta    960
atctttaaac actatgtagt taggtctccc tcacaatcag tccatttggg tagctctaga   1020
tatcggatcc cgacgagctg caccgcggtg gcggccgtat cttttaccca tacgatgttc   1080
ctgactatgc gggctatccc tatgacgtcc cggactatgc aggatcctat ccatatgacg   1140
ttccagatta cgctgctcag tgcggccgcc tgagagtgca ccataccaca gcttttcaat   1200
tcaattcatc attttttttt tattctttt tttgatttcg gtttctttga aattttttg    1260
attcggtaat ctccgaacag aaggaagaac gaaggaagga gcacagactt agattggtat   1320
atatacgcat atgtagtgtt gaagaaacat gaaattgccc agtattctta acccaactgc   1380
acagaacaaa aacctgcagg aaacgaagat aaatcatgtc gaaagctaca tataaggaac   1440
gtgctgctac tcatcctagt cctgttgctg ccaagctatt taatatcatg cacgaaaagc   1500
aaacaaactt gtgtgcttca ttggatgttc gtaccaccaa ggaattactg gagttagttg   1560
aagcattagg tcccaaaatt tgtttactaa aaacacatgt ggatatcttg actgattttt   1620
ccatggaggg cacagttaag ccgctaaagg cattatccgc caagtacaat tttttactct   1680
tcgaagacag aaaatttgct gacattggta atacagtcaa attgcagtac tctgcgggtg   1740
tatacagaat agcagaatgg gcagacatta cgaatgcaca cggtgtggtg ggcccaggta   1800
ttgttagcgg tttgaagcag gcggcagaag aagtaacaaa ggaacctaga ggccttttga   1860
tgttagcaga attgtcatgc aagggctccc tatctactgg agaatatact aagggtactg   1920
ttgacattgc gaagagcgac aaagattttg ttatcggctt tattgctcaa agagacatgg   1980
gtggaagaga tgaaggttac gattggttga ttatgacacc cggtgtgggt ttagatgaca   2040
agggagacgc attgggtcaa cagtatagaa ccgtggatga tgtggtctct acaggatctg   2100
acattattat tgttggaaga ggactatttg caaagggaag ggatgctaag gtagagggtg   2160
aacgttacag aaaagcaggc tgggaagcat atttgagaag atgcggccag caaaactaaa   2220
aaactgtatt ataagtaaat gcatgtatac taaactcaca aattagagct tcaatttaat   2280
tatatcagtt attaccctat gcggtgtgaa ataccgcaca gatgcgtaag gagaaaatac   2340
cgcatcagga aattgtagcg gccgcgaatt tgagcttatc ttttacccat acgatgttcc   2400
tgactatgcg ggctatccct atgacgtccc ggactatgca ggatcctatc catatgacgt   2460
tccagattac gctactagcg gggggccggg tgacgggccc gtcgactgca gaggcctgca   2520
tgcaagcttg gcgtaatcat ggtcatagct gtttcctgtg tgaaattgtt atccgctcac   2580
aattccacac aacatacgag ccggaagcat aaagtgtaaa gcctggggtg cctaatgagt   2640
gagctaactc acattaattg cgttgcgctc actgcccgct ttccagtcgg gaaacctgtc   2700
```

```
gtgccagctg cattaatgaa tcggccaacg cgcggggaga ggcggtttgc gtattgggcg    2760
ctcttccgct tcctcgctca ctgactcgct gcgctcggtc gttcggctgc ggcgagcggt    2820
atcagctcac tcaaaggcgg taatacggtt atccacagaa tcaggggata acgcaggaaa    2880
gaacatgtga gcaaaaggcc agcaaaaggc caggaaccgt aaaaaggccg cgttgctggc    2940
gttttttccat aggctccgcc cccctgacga gcatcacaaa aatcgacgct caagtcagag    3000
gtggcgaaac ccgacaggac tataaagata ccaggcgttt ccccctggaa gctccctcgt    3060
gcgctctcct gttccgaccc tgccgcttac cggatacctg tccgcctttc tcccttcggg    3120
aagcgtggcg ctttctcata gctcacgctg taggtatctc agttcggtgt aggtcgttcg    3180
ctccaagctg ggctgtgtgc acgaaccccc cgttcagccc gaccgctgcg ccttatccgg    3240
taactatcgt cttgagtcca acccggtaag acacgactta tcgccactgg cagcagccac    3300
tggtaacagg attagcagag cgaggtatgt aggcggtgct acagagttct tgaagtggtg    3360
gcctaactac ggctacacta agaacagt atttggtatc tgcgctctgc tgaagccagt    3420
taccttcgga aaaagagttg gtagctcttg atccggcaaa caaaccaccg ctggtagcgg    3480
tggtttttttt gtttgcaagc agcagattac gcgcagaaaa aaaggatctc aagaagatcc    3540
tttgatcttt tctacggggt ctgacgctca gtggaacgaa aactcacgtt aagggatttt    3600
ggtcatgaga ttatcaaaaa ggatcttcac ctagatcctt ttaaattaaa aatgaagttt    3660
taaatcaatc taaagtatat atgagtaaac ttggtctgac agttaccaat gcttaatcag    3720
tgaggcacct atctcagcga tctgtctatt tcgttcatcc atagttgcct gactccccgt    3780
cgtgtagata actacgatac gggagggctt accatctggc cccagtgctg caatgatacc    3840
gcgagaccca cgctcaccgg ctccagattt atcagcaata aaccagccag ccggaagggc    3900
cgagcgcaga gtggtcctg caactttatc cgcctccatc cagtctatta attgttgccg    3960
ggaagctaga gtaagtagtt cgccagttaa tagtttgcgc aacgttgttg ccattgctac    4020
aggcatcgtg gtgtcacgct cgtcgtttgg tatggcttca ttcagctccg gttcccaacg    4080
atcaaggcga gttacatgat cccccatgtt gtgcaaaaaa gcggttagct ccttcggtcc    4140
tccgatcgtt gtcagaagta agttggccgc agtgttatca ctcatggtta tggcagcact    4200
gcataattct cttactgtca tgccatccgt aagatgcttt tctgtgactg gtgagtactc    4260
aaccaagtca ttctgagaat agtgtatgcg cgaccgagt tgctcttgcc cggcgtcaat    4320
acgggataat accgcgccac atagcagaac tttaaaagtg ctcatcattg gaaaacgttc    4380
ttcggggcga aaactctcaa ggatcttacc gctgttgaga tccagttcga tgtaacccac    4440
tcgtgcaccc aactgatctt cagcatcttt tactttcacc agcgtttctg ggtgagcaaa    4500
aacaggaagg caaaatgccg caaaaaaggg aataagggcg acacggaaat gttgaatact    4560
catactcttc ctttttcaat attattgaag catttatcag ggttattgtc tcatgagcgg    4620
atacatattt gaatgtattt agaaaaataa acaaataggg gttccgcgca catttccccg    4680
aaaagtgcca cctgacgtct aagaaaccat tattatcatg acattaacct ataaaaatag    4740
gcgtatcacg aggccctttc gtctcgcgcg tttcggt                             4777
```

<210> SEQ ID NO 105
<211> LENGTH: 70
<212> TYPE: DNA
<213> ORGANISM: Artificial Sequence
<220> FEATURE:
<223> OTHER INFORMATION: primer

<400> SEQUENCE: 105

```
attgcatctt ggcttctagt tttttatat tcaaaagggt tcttaagtgt agctatgacc      60
atgattacgc                                                            70

<210> SEQ ID NO 106
<211> LENGTH: 73
<212> TYPE: DNA
<213> ORGANISM: Artificial Sequence
<220> FEATURE:
<223> OTHER INFORMATION: primer

<400> SEQUENCE: 106 tttttctct atgatgactt attttatatg atatgtagcc tctgtgcttg tttttagttt      60
atgtatgtgt ttt                                                        73

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
gatatcaagc ttatgtcagt aaacccag                                        28

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
catgactcga gttaccagaa gaatatcttg                                      30

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
tggtggaaga ttacccgttc                                                 20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
cgcagccaat actccacata                                                 20
```